US012565474B2

(12) United States Patent　　　　(10) Patent No.:　US 12,565,474 B2
Luesch et al.　　　　　　　　　　　 (45) Date of Patent:　　Mar. 3, 2026

(54) DISCOVERY, TOTAL SYNTHESIS, AND BIOACTIVITY OF DOSCADENAMIDES

(71) Applicants: University of Florida Research Foundation, Incorporated, Gainesville, FL (US); Smithsonian Institution, Washington, DC (US)

(72) Inventors: Hendrik Luesch, Gainesville, FL (US); Xiao Liang, Gainesville, FL (US); Susan Matthew, Houston, TX (US); Jason C. Kwan, Gainesville, FL (US); Qi-Yin Chen, Gainesville, FL (US); Valerie J. Paul, Fort Pierce, FL (US)

(73) Assignees: University of Florida Research Foundation, Incorporated, Gainesville, FL (US); Smithsonian Institution, Washington, DC (US)

( * ) Notice: Subject to any disclaimer, the term of this patent is extended or adjusted under 35 U.S.C. 154(b) by 1075 days.

(21) Appl. No.: 17/630,138

(22) PCT Filed: Jul. 24, 2020

(86) PCT No.: PCT/US2020/043495
§ 371 (c)(1),
(2) Date: Jan. 25, 2022

(87) PCT Pub. No.: WO2021/021629
PCT Pub. Date: Feb. 4, 2021

(65) Prior Publication Data
US 2022/0281816 A1　　Sep. 8, 2022
US 2023/0242482 A9　　Aug. 3, 2023

Related U.S. Application Data

(60) Provisional application No. 62/879,246, filed on Jul. 26, 2019.

(51) Int. Cl.
C07D 207/38　　　(2006.01)

(52) U.S. Cl.
CPC .................................. C07D 207/38 (2013.01)

(58) Field of Classification Search
CPC ................................................... C07D 207/38
See application file for complete search history.

(56) References Cited

U.S. PATENT DOCUMENTS

2016/0200678 A1　　7/2016　Ballser et al.

FOREIGN PATENT DOCUMENTS

WO　　WO 2015/184393 A1　　12/2015
WO　　WO-2018215799 A1 *　11/2018　........... A61K 31/401

OTHER PUBLICATIONS

Han, H., AAPS Pharmsci., 2000, 2, 1-11 (Year: 2000).*
Morissette et al., Advanced Drug Delivery Reviews, 2004, 56, 275-300 (Year: 2004).*
Chaudhari, S.P. & Patil, P.S., IJAPBC, 2012, 1(1), 21-34 (Year: 2012).*
Khan et al., PLOS One, 2015, 10(8), 1-11 (Year: 2015).*
PCT/US2020/043495, Dec. 14, 2020, International Search Report and Written Opinion.
PCT/US2020/043495, Feb. 10, 2022, International Preliminary Report on Patentability.

(Continued)

*Primary Examiner* — John S Kenyon
*Assistant Examiner* — Sara Elizabeth Bell
(74) *Attorney, Agent, or Firm* — Wolf, Greenfield & Sacks, P.C.

(57) ABSTRACT

The invention is directed towards compounds (e.g., Formulae (I)-(IX)), their mechanism of action, processes to prepare the compounds, methods of activating quorum sensing signaling activity, and methods of treating diseases and disorders using the compounds described herein (e.g., Formulae (I)-(IX)).

FIG. 1

Doscadenamide A (1a)

(Continued)

-continued

*Doscadenamide F (1f)

*Doscadenamide G (1g)

*Doscadenamide H (1h)

*Doscadenamide I (1i)

*Doscadenamide J (1j)

Other structures

Doscadenamide S13 (1o)

Synthetic analogs

| | R¹ | R² |
|---|---|---|
| Doscadenamide S4 (1k) | | |
| Doscadenamide S5 (1l) | | |
| Doscadenamide S6 (1m) | | |
| Doscadenamide S7 (1n) | | |
| Doscadenamide S8 (2a) | | H |
| Doscadenamide S9 (2b) | | H |
| Doscadenamide S10 (3a) | Boc | |
| Doscadenamide S11 (3b) | Boc | |
| Doscadenamide S12 (3c) | Boc | |

Transposed functional groups

-continued

Doscadenamide S14 (1p)

Doscadenamide S15 (4a)

23 Claims, 22 Drawing Sheets

(56)                References Cited

OTHER PUBLICATIONS

PCT/US2020/043495, Oct. 14, 2020, Invitation to Pay Additional Fees.
International Search Report and Written Opinion for PCT/US2020/043495 mailed Dec. 14, 2020.
International Preliminary Report on Patentability for PCT/US2020/043495 mailed Feb. 10, 2022.
Invitation to Pay Additional Fees for PCT/US2020/043495 mailed Oct. 14, 2020.
Almohaywi et al., Dihydropyrrolones as bacterial quorum sensing inhibitors. Bioorg Med Chem Lett. May 1, 2019;29(9):1054-1059. doi: 10.1016/j.bmcl.2019.03.004. Epub Mar. 4, 2019. PMID: 30857746. PubChem CID 22225444. Dec. 5, 2007. 9 pages.
Zheng et al., (S)-5-Hexyl-1-[(S)-2-hydroxy-1-phenylethyl]-4-methoxy-1H-pyrrol-2(5H)-on e. Acta crystallographica. Section E, Structure reports online. 2009;65.o1094.10.1107/S1600536809014160.
Amarante-Mendes et al., Therapeutic applications of TRAIL receptor agonists in cancer and beyond. Pharmacol Ther. Nov. 2015;155:117-31. doi: 10.1016/j.pharmthera.2015.09.001. Epub Sep. 5, 2015. Author Manuscript, 38 pages.
Anandakrishnan et al., H++ 3.0: automating pK prediction and the preparation of biomolecular structures for atomistic molecular modeling and simulations. Nucleic Acids Res. Jul. 2012;40(Web Server issue):W537-41. doi: 10.1093/nar/gks375. Epub May 8, 2012.
Cai et al., Apratyramide, a Marine-Derived Peptidic Stimulator of VEGF-A and Other Growth Factors with Potential Application in Wound Healing. ACS Chem Biol. Jan. 19, 2018;13(1):91-99. doi: 10.1021/acschembio.7b00827. Epub Dec. 5, 2017. Author Manuscript, 19 pages.
Engebrecht et al., Identification of genes and gene products necessary for bacterial bioluminescence. Proc Natl Acad Sci U S A. Jul. 1984;81(13):4154-8. doi: 10.1073/pnas.81.13.4154.

(56) References Cited

OTHER PUBLICATIONS

Evans et al., Asymmetric alkylation reactions of chiral imide enolates. A practical approach to the enantioselective synthesis of. alpha.-substituted carboxylic acid derivatives. J Am Chem Soc. Mar. 1982;104(6):1737-9.

French et al., The TRAIL to selective tumor death. Nat Med. Feb. 1999;5(2):146-7. doi: 10.1038/5505.

Geske et al., Small molecule inhibitors of bacterial quorum sensing and biofilm formation. J Am Chem Soc. Sep. 21, 2005;127(37):12762-3. doi: 10.1021/ja0530321.

Henke et al., Three parallel quorum-sensing systems regulate gene expression in Vibrio harveyi. J Bacteriol. Oct. 2004; 186(20):6902-14. doi: 10.1128/JB.186.20.6902-6914.2004.

Hodgkinson et al., Learning the language of bacteria. ACS Chem Biol. Nov. 20, 2007;2(11):715-7. doi: 10.1021/cb700227k.

Jiang et al., Quorum Sensing: A Prospective Therapeutic Target for Bacterial Diseases. Biomed Res Int. Apr. 4, 2019;2019:2015978. doi: 10.1155/2019/2015978.

Kaufmann et al., Revisiting quorum sensing: Discovery of additional chemical and biological functions for 3-oxo-N-acylhomoserine lactones. Proc Natl Acad Sci U S A. Jan. 11, 2005;102(2):309-14. doi: 10.1073/pnas.0408639102. Epub Dec. 27, 2004.

Kravchenko et al., Facilitating cytokine-mediated cancer cell death by proteobacterial N-acylhomoserine lactones. ACS Chem Biol. 2013;8(6):1117-20. doi: 10.1021/cb4000184. Epub Mar. 21, 2013.

Kravchenko et al., Modulation of gene expression via disruption of NF-kappaB signaling by a bacterial small molecule. Science. Jul. 11, 2008;321(5886):259-63. doi: 10.1126/science.1156499. Epub Jun. 19, 2008.

Kwan et al., Lyngbyoic acid, a "tagged" fatty acid from a marine cyanobacterium, disrupts quorum sensing in Pseudomonas aeruginosa. Mol Biosyst. Apr. 2011;7(4):1205-16. doi: 10.1039/c0mb00180e. Epub Jan. 24, 2011. Author Manuscript, 24 pages.

Legler et al., The novel TRAIL-receptor agonist APG350 exerts superior therapeutic activity in pancreatic cancer cells. Cell Death Dis. May 1, 2018;9(5):445. doi: 10.1038/s41419-018-0478-0.

Liang et al., Discovery and Total Synthesis of Doscadenamide A: A Quorum Sensing Signaling Molecule from a Marine Cyanobacterium. Org Lett. Sep. 20, 2019;21(18):7274-7278. doi: 10.1021/acs.orglett.9b02525. Epub Aug. 15, 2019. Author Manuscript, 14 pages.

Matthew et al., Cytotoxic halogenated macrolides and modified peptides from the apratoxin-producing marine cyanobacterium *Lyngbya bouillonii* from Guam. J Nat Prod. Sep. 24, 2010;73(9):1544-52. doi: 10.1021/np1004032. Author Manuscript, 24 pages.

Miller et al., Quorum sensing in bacteria. Annu Rev Microbiol. 2001;55:165-99. doi: 10.1146/annurev.micro.55.1.165.

Montaser et al., Modular strategies for structure and function employed by marine cyanobacteria: characterization and synthesis of pitinoic acids. Org Lett. Aug. 16, 2013;15(16):4050-3. doi: 10.1021/01401396u. Epub Aug. 5, 2013. Author Manuscript, 11 pages.

Montaser et al., Pitipeptolides C-F, antimycobacterial cyclodepsipeptides from the marine cyanobacterium *Lyngbya majuscula* from Guam. Phytochemistry. Nov. 2011;72(16):2068-74. doi: 10.1016/j.phytochem.2011.07.014. Epub Aug. 16, 2011. Author Manuscript, 17 pages.

MÜH et al., A structurally unrelated mimic of a Pseudomonas aeruginosa acyl-homoserine lactone quorum-sensing signal. Proc Natl Acad Sci U S A. Nov. 7, 2006;103(45):16948-52. doi: 10.1073/pnas.0608348103. Epub Oct. 30, 2006.

Naik et al., Quorum Sensing Disruption in *Vibrio harveyi* Bacteria by Clay Materials. J Agric Food Chem. Jan. 1, 20180;66(1):40-44. doi: 10.1021/acs.jafc.7b03918. Epub Dec. 26, 2017.

Rutherford et al., Bacterial quorum sensing: its role in virulence and possibilities for its control. Cold Spring Harb Perspect Med. Nov. 1, 2012;2(11):a012427. doi: 10.1101/cshperspect.a012427.

Sadikot et al., Pathogen-host interactions in Pseudomonas aeruginosa pneumonia. Am J Respir Crit Care Med. Jun. 1, 2005;171(11):1209-23. doi: 10.1164/rccm.200408-1044SO. Epub Feb. 1, 2005.

Salvador-Reyes et al., Biological targets and mechanisms of action of natural products from marine cyanobacteria. Nat Prod Rep. Mar. 2015;32(3):478-503. doi: 10.1039/c4np00104d. Author Manuscript, 52 pages.

Sharif et al., Quorum sensing in Cyanobacteria: N-octanoyl-homoserine lactone release and response, by the epilithic colonial cyanobacterium *Gloeothece* PCC6909. ISME J. Dec. 2008;2(12):1171-82. doi: 10.1038/ismej.2008.68. Epub Jul. 17, 2008.

Smith et al., The Pseudomonas aeruginosa quorum-sensing molecule N-(3-oxododecanoyl)homoserine lactone contributes to virulence and induces inflammation in vivo. J Bacteriol. Feb. 2002;184(4):1132-9. doi: 10.1128/jb.184.4.1132-1139.2002.

Srivastava, TRAIL/Apo-2L: mechanisms and clinical applications in cancer. Neoplasia. Nov.-Dec. 2001;3(6):535-46. doi: 10.1038/sj.neo.7900203.

Tang et al., Quorum quenching agents: resources for antivirulence therapy. Mar Drugs. May 30, 2014;12(6):3245-82. doi: 10.3390/md12063245.

Trivedi et al., Trailing TRAIL Resistance: Novel Targets for TRAIL Sensitization in Cancer Cells. Front Oncol. Apr. 2, 2015;5:69. doi: 10.3389/fonc.2015.00069.

Trott et al., AutoDock Vina: improving the speed and accuracy of docking with a new scoring function, efficient optimization, and multithreading. J Comput Chem. Jan. 30, 2010;31(2):455-61. doi: 10.1002/jcc.21334. Author Manuscript, 18 pages.

Waters et al., The Vibrio harveyi quorum-sensing system uses shared regulatory components to discriminate between multiple autoinducers. Genes Dev. Oct. 1, 2006;20(19):2754-67. doi: 10.1101/gad.1466506.

Zou et al., Molecular basis for the recognition of structurally distinct autoinducer mimics by the Pseudomonas aeruginosa LasR quorum-sensing signaling receptor. Chem Biol. Sep. 25, 2009;16(9):961-70. doi: 10.1016/j.chembiol.2009.09.001.

\* cited by examiner

Doscadenamide A (1a)

f1 (ppm)

f1 (ppm)

f2 (ppm)

FIG. 9

Doscadenamide S3

Doscadenamide S2

Doscadenamide S1

FIG. 18

MDA-MB-231

MDA-MB-231

MDA-MB-231

Δ Bliss independence

| | 50 μM | 25 μM |
|---|---|---|
| C12 | 0.05 | -0.07 |
| 1a | 0.08 | 0.01 |
| 1f | 0.31 | 0.08 |
| 1k | 0.31 | 0.23 |
| 2a | 0.02 | 0.00 |
| 3a | 0.18 | 0.05 |
| 3b | 0.06 | 0.02 |
| 3c | 0.26 | 0.14 |
| 1t | -0.01 | -0.06 |

DISCOVERY, TOTAL SYNTHESIS, AND BIOACTIVITY OF DOSCADENAMIDES

RELATED APPLICATIONS

The present application is a national stage filing under 35 U.S.C. 371 of International Patent Application Serial No. PCT/US2020/043495, filed Jul. 24, 2020, which claims priority under 35 U.S.C. § 119(e) to U.S. provisional application No. 62/879,246, filed Jul. 26, 2019, which are herein incorporated by reference in their entirety.

GOVERNMENT SUPPORT INFORMATION

This invention was made with government support under Grant Nos. CA172310 and GM086210 awarded by the National Institutes of Health. The government has certain rights in the invention.

BACKGROUND

Quorum sensing (QS) is an intercellular communication process adopted by a number of bacteria to regulate diverse physiological activities. This process involves the production and release of diffusible extracellular signaling molecules named autoinducers (AIs), which would accumulate with increasing bacterial population density [Miller, M. B.; Bassler, B. L., *Annu. Rev. Microbiol.* 2001, 55, 165-199; Rutherford, S. T.; Bassler, B. L., *Cold Spring Harb Perspect. Med.* 2012, 2 (11), a012427; Galloway, W.; Hodgkinson, J.; Bovvden, S.; Welch, M.; Spring, D., *Trends Microbiol.* 2012, 20 (9), 449-458]. QS plays a pivotal role in regulating bacterial pathogenesis. For example, QS modulates the production of virulence factors such as pyocyanin and elastase in *Pseudomonas aeruginosa* during bacterial growth and infection [Jiang, Q.; Chen, J.; Yang, C.; Yin, Y.; Yao, K., *BioMed. Res. Int.* 2019, 1-15]. Thus, QS signaling pathway is an attractive target for the development of antimicrobial therapeutic agents. *P. aeruginosa* is a Gram-negative opportunistic pathogen that can cause serious infections such as cystic fibrosis (CF) in lung and microbial keratitis (MK) during contact lens wear [Sadikot, R.; Blackwell, T.; Christman, J.; Prince, A., *Am. J. Respir. Crit. Care Med.* 2005, 171 (11), 1209-1223; Willcox, M. D., *Optom. Vis. Sci.* 2007, 84 (4), 273-278]. The AIs that control QS signaling pathway in *P. aeruginosa* include two acylhomoserine lactones (AHLs, C

O
C4-HSL (C4)

O O
3-oxo-C12-HSL (C12)
)

with varying alkyl chain lengths and oxidation states at C-3 and a group of quinolone compounds (*Pseudomonas* quinolone signal, PQS). They can diffuse freely across cell membranes and bind intracellularly with corresponding receptor proteins (R proteins) [Kwan, J. C.; Meickle, T.; Ladwa, D.; Teplitski, M.; Paul, V.; Luesch, H., *Mol. Biosyst.* 2011, 7 (4), 1205-1216]. These signaling systems form a complex hierarchical quorum sensing network, where the Las system is considered to be the apex of the hierarchy [Galloway, W. R.; Hodgkinson, J. T.; Bowden, S. D.; Welch, M.; Spring, D. R., *Chem. Rev.* 2011, 111 (1), 28-67]. Therefore, the LasR receptor has been usually considered to be the target for antagonist and agonist development in *P. aeruginosa* [Galloway, W. R.; Hodgkinson, J. T.; Bowden, S. D.; Welch, M.; Spring, D. R., *Chem. Rev.* 2011,111 (1), 28-67; Hodgkinson, J. T.; Welch, M.; Spring, D. R., *ACS Chem. Biol.* 2007, 2 (11), 715-717]. For example, a synthetic non-native AHL, QSI-1, was demonstrated to be a potent LasR antagonist [Geske, G. D.; Wezeman, R. J.; Siegel, A. P.; Blackwell, H. E., *J. Am. Chem. Soc.* 2005, 127 (37), 12762-12763]. The structurally unrelated mimic of AHL, TP-1, is a highly selective superagonist of the LasR quorum sensing system; while its derivative TP-5 turned into a moderate QS antagonist [Müh, U.; Hare, B. J.; Duerkop, B. A.; Schuster, M.; Hanzelka, B. L.; Heim, R.; Olson, E. R.; Greenberg, E. P., *Proc. Natl. Acad. Sci. U.S.A.* 2006, 103 (45), 16948-16952; Zou, Y.; Nair, S. K., *Chem. Biol.* 2009, 16 (9), 961-970]. Moreover, there is evidence showing that N-octanoyl homoserine lactone can be produced in the cyanobacterium culture of Gloeothece PCC6909 and its accumulation corresponds to a characteristic pattern of auto-induction [Sharif, D. I.; Gallon, J.; Smith, C. J.; Dudley, E., *ISME J* 2008, 2 (12), 1171-1182]. In addition to antimicrobial (e.g., antibacterial) applications, modulation of QS has also been shown to attenuate NFκB gene expression and activity [Kravchenko, V. et al., *Science* 2008, 321, 259-263]. Additionally, modulation of QS has been demonstrated to synergize with TRAIL to induce cancer cell death. TRAIL (tumor necrosis factor-related apoptosis-inducing ligand), also known as Apo-2L and TNFSF10, is a TNF family cytokine that can induce cell apoptosis and cause programmed cell death by binding to the death receptors DR4 (TRAIL-RI) and DR5 (TRAIL-RII) (von Karstedt, et al. *Nat Rev Cancer* 2017, 17 (6), 352-366; Srivastava, at al. *Neoplasia* 2001, 3 (6), 535-46). Moreover, there are studies showing that TRAIL can selectively cause cancer cell death without detrimental effects on normal cells (Srivastava, at al. *Neoplasia* 2001, 3 (6), 535-46; French, et al. The TRAIL to selective tumor death. *Nature Medicine* 1999, 5 (2), 146-147). This selectivity has made TRAIL a promising candidate for cancer therapy (Trivedi, et al. *Front Oncol* 2015, 5, 69) and stimulated intensive studies towards the development of therapeutic agents targeting the TRAIL signaling pathway (von Karstedt, et al. *Nat Rev Cancer* 2017, 17 (6), 352-366), including recombinant TRAIL proteins and monoclonal antibody agonists specific for DR4 (TRAIL-RI) and DR5 (TRAIL-RII) (Amarante-Mendes, et al. *Pharmacology & Therapeutics* 2015, 155, 117-131). However, these agents did not achieve satisfying anticancer activities in clinical investigations (Legler, et al. *Cell Death Dis* 2018, 9 (5), 445. because many cancer cells have developed resistance toward TRAIL, thus compromising the efficacy of TRAIL-therapy (Trivedi, et al. *Front Oncol* 2015, 5, 69; Kravchenko, et al. *ACS Chem Biol* 2013, 8 (6), 1117-20).

Thus, modulation of QS may be a useful approach to treat cancer and/or increasing the effectiveness of existing anticancer therapies.

Marine cyanobacteria have been a valuable source for the discovery of biologically active and structurally unique natural products including peptides, polyketides and hybrid of peptide-polyketides. It is noteworthy that marine cyano-bacterial also produce various AHL-dependent QS inhibitors [Tang, K.; Zhang, X. H., *Mar. Drugs.* 2014, 12 (6), 3245-3282]. For instance, lyngbyoic acid, Lyngbyoic acid small cyclopropane-containing fatty acid, was isolated from *Lyngbya* cf. *majuscula* and proved to strongly inhibit the activity of LasR [Kwan, J. C.; Meickle, T.; Ladwa, D.; Teplitski, M.; Paul, V.; Luesch, H., *Mol. Biosyst.* 2011, 7 (4), 1205-1216]. Moreover, pitinoic acid A, Pitinoic acid A was also reported to be a *P. aeruginosa* quorum sensing inhibitor [Montaser, R.; Paul, V. J.; Luesch, H., *Org. Lett.* 2013, 15 (16), 4050-4053]. In addition to these QS inhibitors, herein is reported the isolation, total synthesis, and QS modulation activity of a series of novel compounds.

BRIEF SUMMARY OF THE INVENTION

The invention is directed towards compounds (e.g., Formulae (I)-(IX)), their mechanism of action, and methods of modulating quorum sensing signaling, and methods of treating diseases and disorders using the compounds described herein (e.g., Formulae (I)-(IX)). In another aspect, the disease or disorder is cancer. In another aspect, the disease or disorder is a bacterial infection.

In another aspect, the invention is directed to a compound of Formula (IX):

(IX)

or a pharmaceutically acceptable salt, solvate, hydrate, or prodrug thereof;

-continued wherein $R_{13}$ is H, Boc, acetyl, Fmoc, each $R_{14}$ is independently H or $C_1$-$C_6$ alkyl;

$R_{15}$ is H or $C_1$-$C_6$ alkyl;

each $R_6$ is independently H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl.

In another aspect, the invention is directed to:

(doscadenamide A)

(doscadenamide I)

(doscadenamide H)

-continued (doscadenamide F)

(doscadenamide D)

(doscadenamide E)

(doscadenamide C)

(doscadenamide B)

65 or a pharmaceutically acceptable salt, solvate, hydrate, or prodrug thereof.

In another aspect, the invention is directed to:

(doscadenamide A)

(doscadenamide I)

(doscadenamide H)

(doscadenamide F)

(doscadenamide D)

-continued (doscadenamide E)

(doscadenamide C)

(doscadenamide B)

(doscadenamide G)

; or (doscadenamide J)

;

or a pharmaceutically acceptable salt, solvate, hydrate, or prodrug thereof.

In another aspect, the invention is directed to a compound of Formula (IX):

(IX)

or a pharmaceutically acceptable salt, solvate, hydrate, or prodrug thereof;

wherein $R_{13}$ is H, Boc, acetyl, Fmoc,

, or

;

each $R_{14}$ is independently H or $C_1$-$C_6$ alkyl;

$R_{15}$ is H or $C_1$-$C_6$ alkyl;

each $R_6$ is independently H, $C_1$-$C_6$ alkyl, $C_2$-$C_6$ alkenyl, or $C_2$-$C_6$ alkynyl;

$R_8$ is H, Boc, acetyl, Fmoc, or

;

$R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl;

wherein the compound is not:

(doscadenamide A)

;

-continued (doscadenamide I)

(doscadenamide H)

(doscadenamide F)

(doscadenamide D)

(doscadenamide E)

-continued (doscadenamide C)

(doscadenamide B)

or a pharmaceutically acceptable salt, solvate, hydrate, or prodrug thereof.

In another aspect, the invention is directed to a compound of Formula (IX):

(IX)

or a pharmaceutically acceptable salt, solvate, hydrate, or prodrug thereof;

wherein $R_{13}$ is H, Boc, acetyl, Fmoc, $R_6$, or $R_6$;

each $R_{14}$ is independently H or $C_1$-$C_6$ alkyl;

$R_{15}$ is H or $C_1$-$C_6$ alkyl;

each $R_6$ is independently H, $C_1$-$C_6$ alkyl, $C_2$-$C_6$ alkenyl, or $C_2$-$C_6$ alkynyl;

11

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl;

wherein the compound is not:

(doscadenamide A)

(doscadenamide I)

(doscadenamide H)

(doscadenamide F)

12

-continued (doscadenamide D)

(doscadenamide E)

(doscadenamide C)

(doscadenamide B)

(doscadenamide G)

; or

-continued (doscadenamide J)

or a pharmaceutically acceptable salt, solvate, hydrate, or prodrug thereof.

In another aspect, the invention provides a pharmaceutical composition comprising a compound described herein (e.g., Formulae (I)-(IX)), or a pharmaceutically acceptable salt, hydrate, solvate, or prodrug thereof, and a pharmaceutically acceptable carrier. In another aspect, the pharmaceutical composition described herein further comprises an additional agent. In another aspect, the additional agent is an anti-cancer agent. In another aspect, the additional agent is an anti-bacterial agent.

In another aspect, the invention provides a method of modulating quorum sensing signaling, the method comprising administering an effective amount of a compound described herein (e.g., Formulae (I)-(IX)), or a pharmaceutically acceptable salt, hydrate, solvate, or prodrug thereof. In another aspect, the modulation is activation. In another aspect, the modulation is inhibition. In another aspect, the compound is administered in vitro. In another aspect, the compound is administered in vivo. In another aspect, the method further comprises administering the compound to a subject.

In another aspect, the invention provides a method of inhibiting bacterial growth, the method comprising administering an effective amount of a compound described herein (e.g., Formulae (I)-(IX)), or a pharmaceutically acceptable salt, hydrate, solvate, or prodrug thereof. In another aspect, the compound is administered in vitro. In another aspect, the compound is administered in vivo. In another aspect, the method further comprises administering the compound to a subject.

In another aspect, the invention provides a method of treating a disease or disorder in a subject in need thereof, the method comprising administering an effective amount of a compound described herein (e.g., Formulae (I)-(IX)), or a pharmaceutically acceptable salt, hydrate, solvate, or prodrug thereof. In another aspect, the disease is cancer. In another aspect, the disease is a bacterial infection. In another aspect, the subject is a mammal. In another aspect, the subject is a human.

In another aspect, the invention provides a method of increasing the effectiveness of anti-cancer therapy in a subject currently being administered one or more anti-cancer therapies, the method comprising administering an effective amount of a compound described herein (e.g., Formulae (I)-(IX)), or a pharmaceutically acceptable salt, hydrate, solvate, or prodrug thereof. In certain embodiments, the anti-cancer therapy is TRAIL. In certain embodiments, the method increases the effectiveness of TRAIL. In another aspect, the subject is a mammal. In another aspect, the subject is a human.

In another aspect, the invention provides a method of increasing the effectiveness of anti-bacterial therapy in a subject currently being administered one or more anti-bacterial therapies, the method comprising administering an effective amount of a compound described herein (e.g., Formulae (I)-(IX)), or a pharmaceutically acceptable salt, hydrate, solvate, or prodrug thereof. In another aspect, the subject is a mammal. In another aspect, the subject is a human.

In another aspect, the invention provides a process to prepare a compound of Formula (X) and/or Formula (XI).

BRIEF DESCRIPTION OF THE DRAWINGS

The present invention is further described below with reference to the following non-limiting examples and with reference to the following figures, in which:

FIG. 9. depicts the Δδ calculation of the α-methyl in the side chain of 1a.

Data are presented as mean±SD, P<0.01, **P<0.0001, compared to solvent control using one-way ANOVA (n=3).

Figure 17:
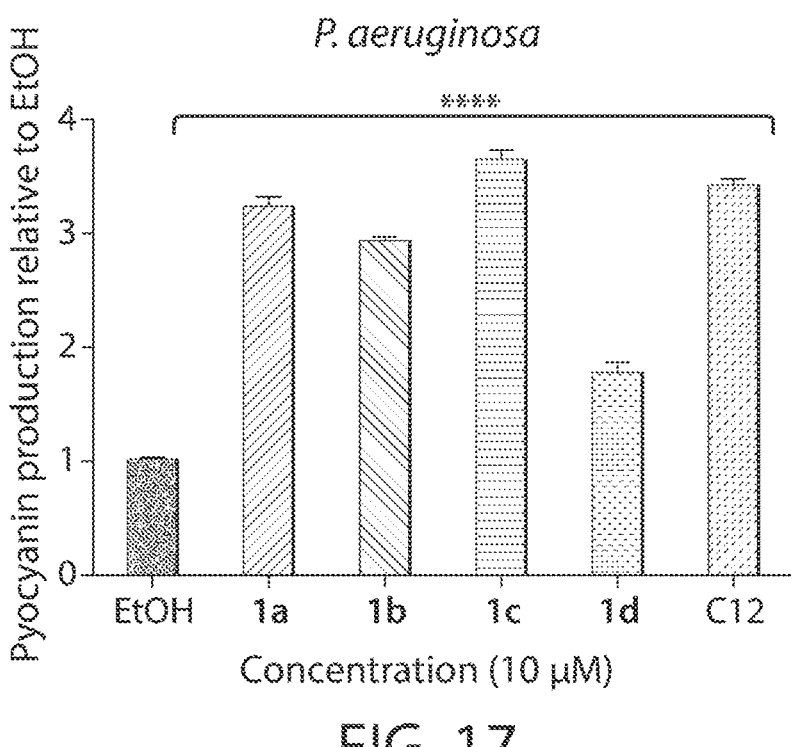

FIG. 17. depicts the effect of doscadenamide A (1a) and its related diastereomers 1b, 1c, 1d, as well as positive control 3-oxo-C12-HSL (C12) at 10 PM, on the production of pyocyanin in wild-type *P. aeruginosa* after 6 h shaking at 37° C. Data are presented as mean±SD, P<0.01, **P<0.0001, compared to solvent control using one-way ANOVA (n=3).

Figure 18:
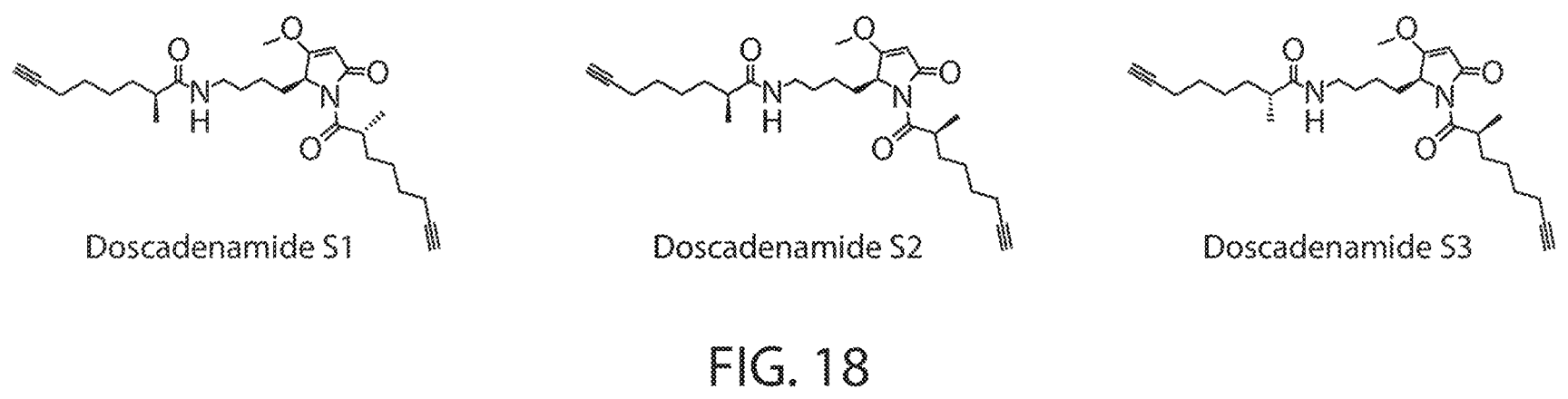

FIG. 18 depicts the structures of doscadenamides S1-S3.

Figure 19A:
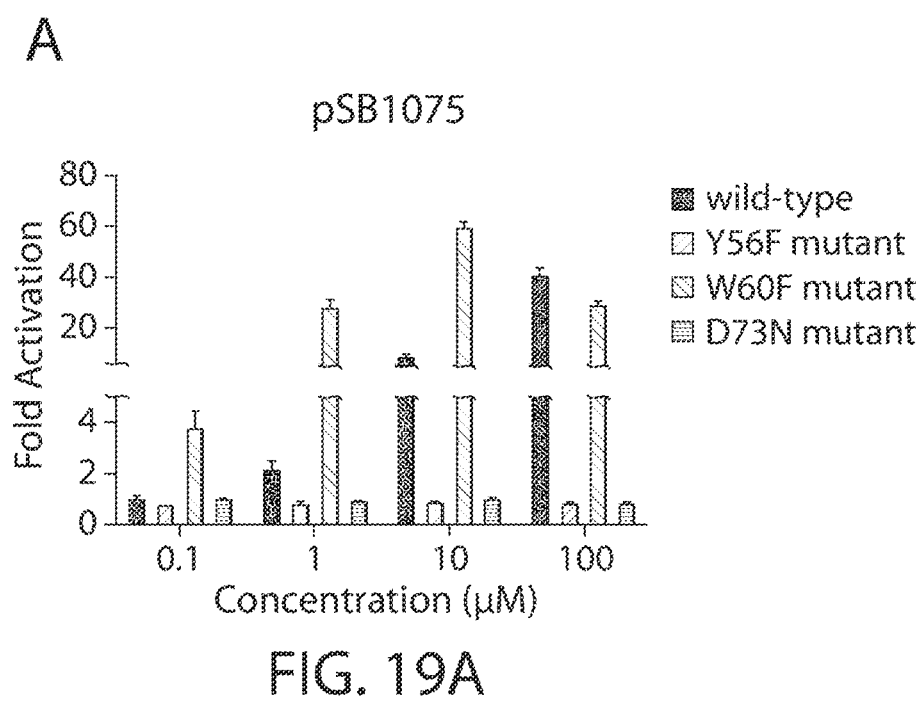
Figure 19B:
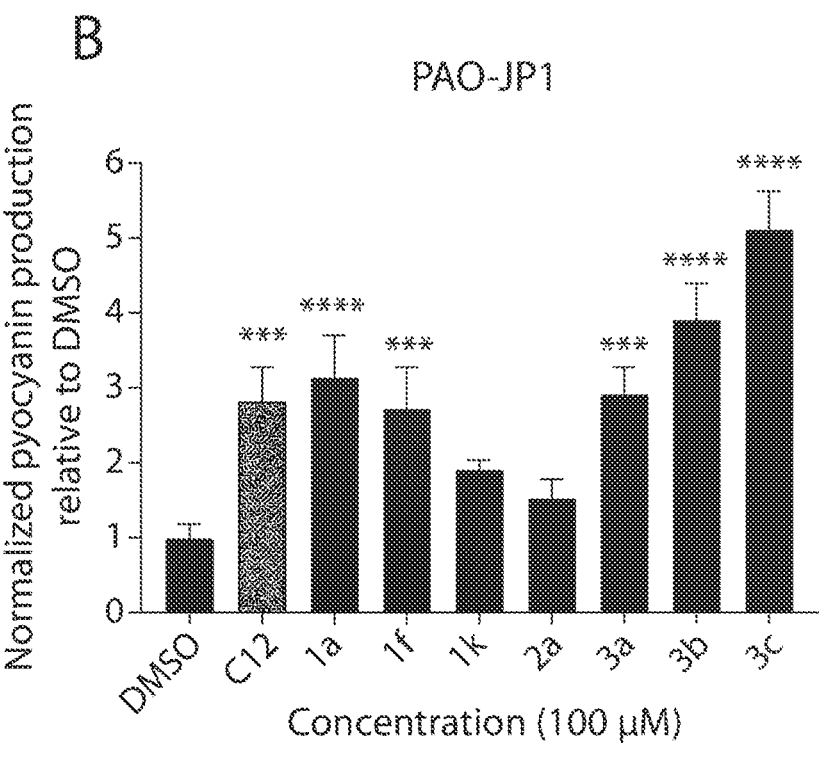
Figure 19C:
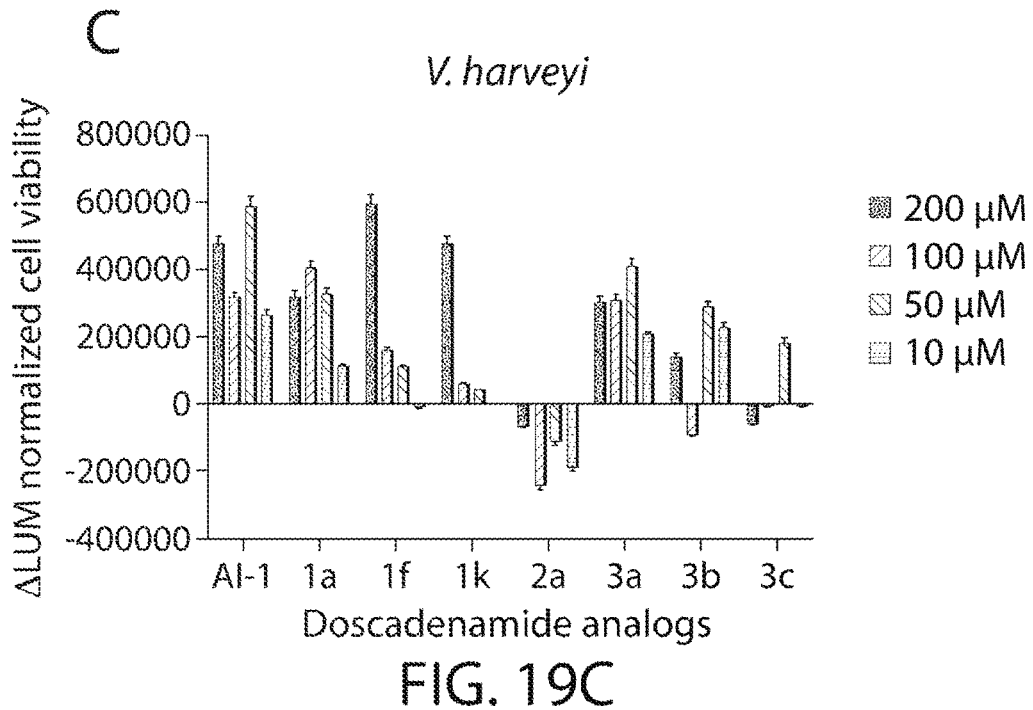

FIGS. 19A-C depict QS activity in different systems. FIG. 19A is a graph showing activity of doscadenamide A (1a) in *E. coli* reporter gene assay using pSB1075 (wild-type) and point mutants (Y56F, W60F and D73N). FIG. 19B is a graph showing normalized pyocyanin production in *P. aeruginosa* mutant PAO-JP1 after treatment with doscadenamide A (1a) and its structural analogs for 6 h at 10 μM. C12 was used as the positive control. FIG. 19C is a graph showing measurement of QS activating activity of doscadenamide A (1a) and its structural analogs in *V. harveyi* after 8 h treatment, presented by ΔLUM [ΔLUM=LUM (doscadenamide analog)–LUM (DMSO)] normalized by cell viability measured with OD600. AI-1 is a reported quorum sensing autoinducer and was used as the positive control.

Figure 20A:
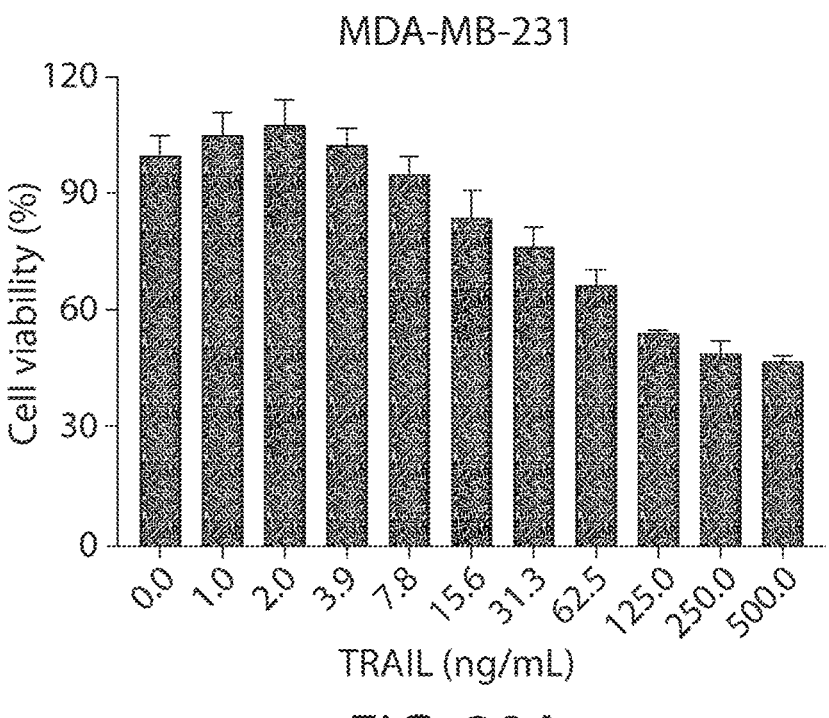
Figure 20B:
Figure 20B:
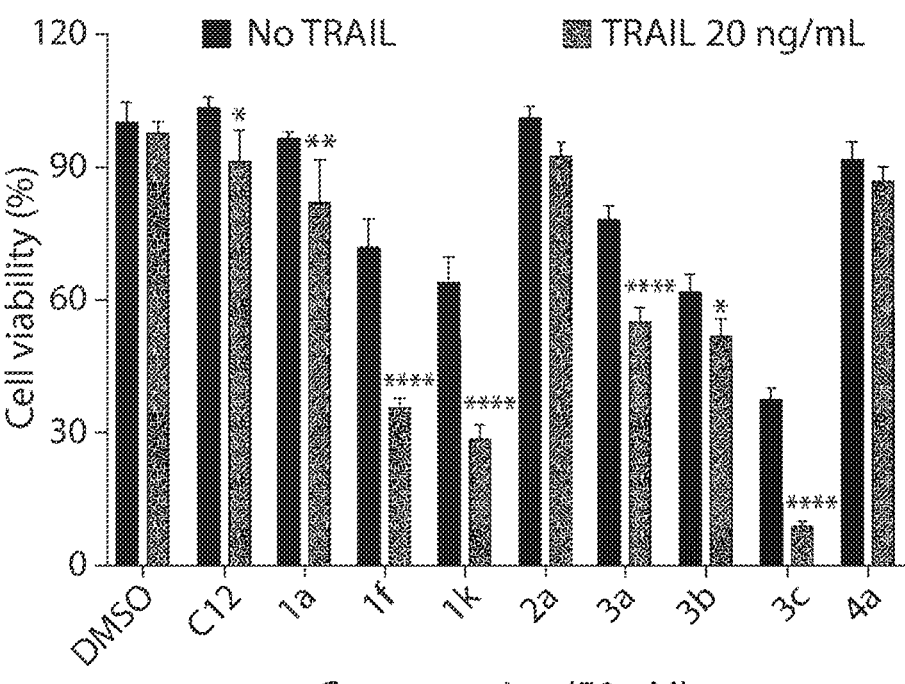
Figures 20C, 20D:
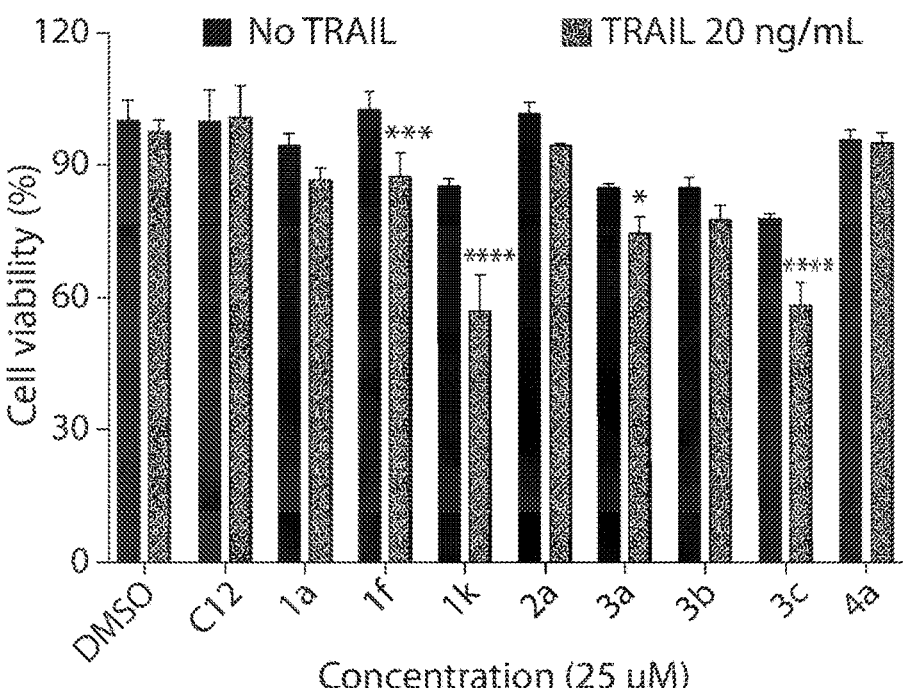
Figure 20E:
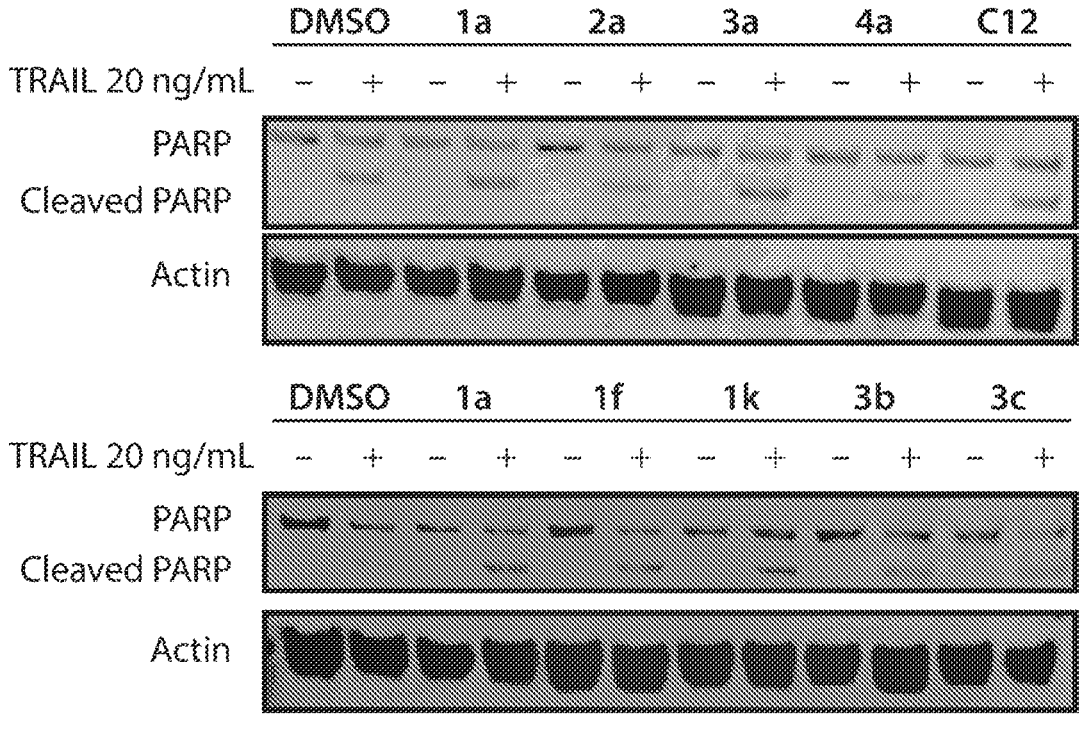

FIGS. 20A-E depict that doscadenamide A (1a) and its structural analogs sensitize breast cancer MDA-MB-231 cells in combination with TRAIL. FIGS. 20A-C are graphs showing dose-response analysis of TRAIL on MDA-MB-231 cells. MDA-MB-231 cell viability after 3 h pretreatment with DMSO (solvent control), C12 as well as doscadenamide A (1a) and its structural analogs, B) 5 μM and C) 2 μM followed by combined TRAIL (20 ng/mL) treatment for 24 h. FIG. 20D is a chart showing A Bliss independence calculations for MDA-MB-231 cells cotreated with TRAIL (20 ng/mL) and doscadenamide A (1a) and its structural analogs. MDA-MB-231 cells were treated with doscadenamide A (1a) and its structural analogs for 3 h, followed by treatment with TRAIL (20 ng/mL) for 24 h, C12 was included as positive control. "A Bliss independence" is the difference between observed growth inhibition and Bliss expectation. Values greater than zero represent a synergistic response, represented as red in the figure. Bliss expectation is C=(A+B)–(A×B), where A and B are the growth inhibition fractions of two compounds at a given dose. Cell viability was quantified using MTT assay. FIG. 20E is a western blot analysis of protein extracts from breast cancer MDA-MB-231 cells after treatment with TRAIL (20 ng/mL), doscadenamide A (1a) and its analogs (50 μM) and their combination as shown in the figure.

DETAILED DESCRIPTION

Definitions

In order that the invention may be more readily understood, certain terms are first defined here for convenience.

As used herein, the term "treating" a disorder encompasses ameliorating, mitigating and/or managing the disorder and/or conditions that may cause the disorder. The terms "treating" and "treatment" refer to a method of alleviating or abating a disease and/or its attendant symptoms. In accordance with the present invention, "treating" includes blocking, inhibiting, attenuating, modulating, reversing the effects of and reducing the occurrence of e.g., the harmful effects of a disorder.

As used herein, "inhibiting" encompasses reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide.

These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three-dimensional structure of a polypeptide monomer. "Quaternary structure" refers to the three-dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 g/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 pM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 g/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore, the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, hydrobromic, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions.

Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art.

Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Compounds delineated herein (e.g., Formulae (I)-(XI)) include salt, hydrate and solvates thereof. They include all compounds delineated in schemes herein, whether intermediate or final compounds in a process.

Compounds of the invention can be obtained from natural sources or made or modified made by means known in the art of organic synthesis. Methods for optimizing reaction conditions, if necessary, minimizing competing by-products, are known in the art. Reaction optimization and scale-up may advantageously utilize high-speed parallel synthesis equipment and computer-controlled microreactors (e.g., *Design And Optimization in Organic Synthesis, 2^{nd}* Edition, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artisan by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. All hydrate and solvate forms of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

In another aspect, the invention is directed to a compound of Formula (IX):

(IX)

or a pharmaceutically acceptable salt, solvate, hydrate, or prodrug thereof;

wherein $R_{13}$ is H, Boc, acetyl, Fmoc, $R_6$, or $R_6$;

each $R_{14}$ is independently H or $C_1$-$C_6$ alkyl;

$R_{15}$ is H or $C_1$-$C_6$ alkyl;

each $R_6$ is independently H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl.

In another aspect, the invention is directed to a compound of Formula (IX):

(IX)

or a pharmaceutically acceptable salt, solvate, hydrate, or prodrug thereof;

wherein $R_{13}$ is H, Boc, acetyl, Fmoc, $R_6$, or $R_6$;

each $R_{14}$ is independently H or $C_1$-$C_6$ alkyl;

$R_{15}$ is H or $C_1$-$C_6$ alkyl;

each $R_6$ is independently H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl;

23 wherein the compound is not:

(doscadenamide A)

(doscadenamide I)

(doscadenamide H)

(doscadenamide F)

(doscadenamide D)

24

-continued (doscadenamide E)

(doscadenamide C)

(doscadenamide B)

or a pharmaceutically acceptable salt, solvate, hydrate, or prodrug thereof.

In another aspect, the invention is directed to a compound of Formula (IX):

or a pharmaceutically acceptable salt, solvate, hydrate, or prodrug thereof;

wherein $R_{13}$ is H, Boc, acetyl, Fmoc,

-continued each $R_{14}$ is independently H or $C_1$-$C_6$ alkyl;

$R_{15}$ is H or $C_1$-$C_6$ alkyl;

each $R_6$ is independently H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl;

wherein the compound is not:

(doscadenamide A)

(doscadenamide I)

(doscadenamide H)

26

-continued (doscadenamide F)

(doscadenamide D)

(doscadenamide E)

(doscadenamide C)

(doscadenamide B)

27

-continued (doscadenamide G)

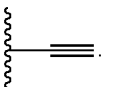

; or (doscadenamide J)

or a pharmaceutically acceptable salt, solvate, hydrate, or prodrug thereof.

In another aspect, $R_8$ is

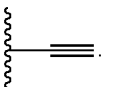

In another aspect, $R_9$ is H. In another aspect, $R_{10}$ is $C_1$-$C_6$ alkyl. In another aspect, $R_9$ is H and $R_{10}$ is $C_1$-$C_6$ alkyl. In another aspect, $R_{10}$ is Me. In another aspect, $R_{10}$ is H. In another aspect, $R_9$ is $C_1$-$C_6$ alkyl. In another aspect, $R_{10}$ is H and $R_9$ is $C_1$-$C_6$ alkyl. In another aspect, $R_9$ is Me. In another aspect, $R_7$ is $C_2$-$C_6$ alkynyl. In another aspect, $R_7$ is

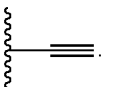

In another aspect, $R_7$ is $C_2$-$C_6$ alkenyl. In another aspect, $R_7$ is

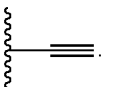

28

In another aspect, $R_7$ is $C_1$-$C_6$ alkyl. In another aspect, $R_7$ is

In another aspect, $R_{13}$ is

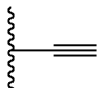

In another aspect $R_{14}$ is H. In another aspect, $R_{14}$ is $C_1$-$C_6$ alkyl. In another aspect, $R_{14}$ is Me. In another aspect, $R_6$ is $C_2$-$C_6$ alkynyl. In another aspect, $R_6$ is

In another aspect, $R_6$ is $C_2$-$C_6$ alkenyl. In another aspect, $R_6$ is

In another aspect, $R_6$ is $C_1$-$C_6$ alkyl. In another aspect $R_6$ is

In another aspect, $R_{13}$ is

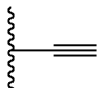

In another aspect $R_{14}$ is H. In another aspect, $R_{14}$ is H and $R_{15}$ is $C_1$-$C_6$ alkyl. In another aspect, $R_{14}$ is H and $R_{15}$ is Me. In another aspect, $R_{15}$ is H. In another aspect, $R_{15}$ is H and $R_{14}$ is $C_1$-$C_6$ alkyl. In another aspect, $R_{15}$ is H and $R_{14}$ is Me. In another aspect, $R_6$ is $C_2$-$C_6$ alkynyl. In another aspect, $R_6$ is

In another aspect, $R_6$ is $C_2$-$C_6$ alkenyl. In another aspect, $R_6$ is

In another aspect, $R_6$ is $C_1$-$C_6$ alkyl. In another aspect $R_6$ is

In another aspect, the invention is directed to a compound of Formula (I):

(I)

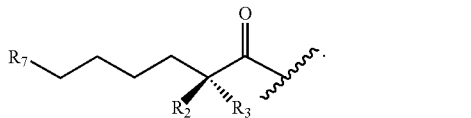

or a pharmaceutically acceptable salt, solvate, hydrate, or prodrug thereof;

wherein $R_1$ is H, Boc, acetyl, Fmoc, or

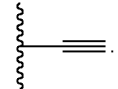

$R_2$ is H or $C_1$-$C_6$ alkyl;
$R_3$ is H;
$R_4$ is H or $C_1$-$C_6$ alkyl;
$R_5$ is H or $C_1$-$C_6$ alkyl;
$R_6$ is H, $C_1$-$C_6$ alkyl, $C_2$-$C_6$ alkenyl, or $C_2$-$C_6$ alkynyl; and
$R_7$ is H, $C_1$-$C_6$ alkyl, $C_2$-$C_6$ alkenyl, or $C_2$-$C_6$ alkynyl. In another aspect, $R_1$ is

In another aspect, $R_2$ is $C_1$-$C_6$ alkyl. In another aspect, $R_2$ is Me. In another aspect, $R_7$ is $C_2$-$C_6$ alkynyl. In another aspect, $R_7$ is

In another aspect, $R_7$ is $C_2$-$C_6$ alkenyl. In another aspect, $R_7$ is

In another aspect, $R_7$ is $C_1$-$C_6$ alkyl. In another aspect, $R_7$ is

In another aspect $R_4$ is H. In another aspect, $R_4$ is H and $R_5$ is $C_1$-$C_6$ alkyl. In another aspect, $R_4$ is H and $R_5$ is Me. In another aspect, $R_5$ is H. In another aspect, $R_5$ is H and $R_4$ is $C_1$-$C_6$ alkyl. In another aspect, $R_5$ is H and $R_4$ is Me. In another aspect, $R_6$ is $C_2$-$C_6$ alkynyl. In another aspect, $R_6$ is

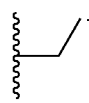

In another aspect, $R_6$ is $C_2$-$C_6$ alkenyl. In another aspect, $R_6$ is

In another aspect, $R_6$ is $C_1$-$C_6$ alkyl. In another aspect, $R_6$ is

In another aspect, the compound of Formula (I), or a pharmaceutically acceptable salt, solvate, hydrate, or prodrug thereof, is according to Formula (II):

(II)

(doscadenamide S1)

or a pharmaceutically acceptable salt, solvate, hydrate, or prodrug thereof.

In another aspect, the compound of Formula (I), or a pharmaceutically acceptable salt, solvate, hydrate, or prodrug thereof, is according to Formula (III):

(doscadenamide S2)

(III)

(doscadenamide S6)

or a pharmaceutically acceptable salt, solvate, hydrate, or prodrug thereof.

In another aspect, the compound of Formula (I), or a pharmaceutically acceptable salt, solvate, hydrate, or prodrug thereof, is according to Formula (IV):

(doscadenamide S5)

(IV)

(doscadenamide J)

or a pharmaceutically acceptable salt, solvate, hydrate, or prodrug thereof.

In another aspect, the compound of Formula (I), or a pharmaceutically acceptable salt, solvate, hydrate, or prodrug thereof, is

33

-continued (doscadenamide S7)

; or (doscadenamide S10)

;

or a pharmaceutically acceptable salt, solvate, hydrate, or prodrug thereof.

In another aspect, the compound of Formula (I), or a pharmaceutically acceptable salt, solvate, hydrate, or prodrug thereof, is (doscadenamide S1)

;

(doscadenamide S2)

;

34

-continued (doscadenamide S6)

;

(doscadenamide S5)

;

(doscadenamide J)

;

(doscadenamide S7)

;

(doscadenamide S10)

;

35

-continued (doscadenamide S11)

(doscadenamide S12)

(doscadenamide G)

or a pharmaceutically acceptable salt, solvate, hydrate, or prodrug thereof.

In another aspect, the compound of Formula (I), or a pharmaceutically acceptable salt, solvate, hydrate, or prodrug thereof, is (doscadenamide S1)

(doscadenamide S2)

36

-continued (doscadenamide S6)

(doscadenamide S5)

(doscadenamide J)

(doscadenamide S7)

(doscadenamide S10)

-continued (doscadenamide S11)

or a pharmaceutically acceptable salt, solvate, hydrate, or prodrug thereof;

wherein $R_4$ is H or $C_1$-$C_6$ alkyl;

$R_5$ is H or $C_1$-$C_6$ alkyl;

$R_6$ is H, $C_1$-$C_6$ alkyl, $C_2$-$C_6$ alkenyl, or $C_2$-$C_6$ alkynyl;

$R_8$ is H, Boc, acetyl, Fmoc, or (doscadenamide S12)

$R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl. In another aspect, $R_8$ is or a pharmaceutically acceptable salt, solvate, hydrate, or prodrug thereof.

In certain embodiments, the compound of Formula (I), or a pharmaceutically acceptable salt, solvate, hydrate, or prodrug thereof, is not In another aspect, $R_9$ is H. In another aspect, $R_{10}$ is $C_1$-$C_6$ alkyl. In another aspect, $R_9$ is H and $R_{10}$ is $C_1$-$C_6$ alkyl. In another aspect, wherein $R_{10}$ is Me. In another aspect, $R_{10}$ is H. In another aspect, $R_9$ is $C_1$-$C_6$ alkyl. In another aspect, $R_{10}$ is H and $R_9$ is $C_1$-$C_6$ alkyl. In another aspect, wherein $R_9$ is Me. In another aspect, $R_7$ is $C_2$-$C_6$ alkynyl. In another aspect, $R_7$ is (doscadenamide J)

In another aspect, $R_7$ is $C_2$-$C_6$ alkenyl. In another aspect, $R_7$ is

(doscadenamide G)

In another aspect, $R_7$ is $C_1$-$C_6$ alkyl. In another aspect, $R_7$ is

In another aspect, the invention is directed to a compound of Formula (V):

(V)

In another aspect, $R_4$ is H. In another aspect, $R_4$ is H and $R_5$ is $C_1$-$C_6$ alkyl. In another aspect, $R_4$ is H and $R_5$ is Me. In another aspect, $R_5$ is H. In another aspect, $R_5$ is H and $R_4$ is $C_1$-$C_6$ alkyl. In another aspect, $R_5$ is H and $R_4$ is Me. In another aspect, $R_6$ is $C_2$-$C_6$ alkynyl. In another aspect, $R_6$ is

In another aspect, $R_6$ is $C_2$-$C_6$ alkenyl. In another aspect, $R_6$ is

In another aspect, $R_6$ is $C_1$-$C_6$ alkyl. In another aspect, $R_6$ is

In another aspect the compound is (doscadenamide S13)

or a pharmaceutically acceptable salt, solvate, hydrate, or prodrug thereof.

In another aspect, the invention is directed to a compound of Formula (VI):

(VI)

or a pharmaceutically acceptable salt, solvate, hydrate, or prodrug thereof;

wherein $R_{12}$ is H, Boc, acetyl, Fmoc, or $R_{11}$ is $C_1$-$C_6$ alkyl;

$R_6$ is H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl. In another aspect, $R_{11}$ is $C_1$-$C_6$ alkyl. In another aspect, $R_{11}$ is Me. In another aspect, $R_8$ is In another aspect, $R_9$ is H. In another aspect, $R_{10}$ is $C_1$-$C_6$ alkyl. In another aspect, $R_9$ is H and $R_{10}$ is $C_1$-$C_6$ alkyl. In another aspect, $R_{10}$ is Me. In another aspect, $R_{10}$ is H. In another aspect, $R_9$ is $C_1$-$C_6$ alkyl. In another aspect, $R_{10}$ is H and $R_9$ is $C_1$-$C_6$ alkyl. In another aspect, $R_9$ is Me. In another aspect, $R_7$ is $C_2$-$C_6$ alkynyl. In another aspect, $R_7$ is

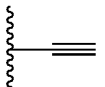

In another aspect, $R_7$ is $C_2$-$C_6$ alkenyl. In another aspect, $R_7$ is

In another aspect, $R_7$ is $C_1$-$C_6$ alkyl. In another aspect, $R_7$ is

41

42

In another aspect, $R_6$ is $C_2$-$C_6$ alkynyl. In another aspect, $R_6$ is

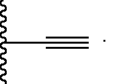

In another aspect, $R_6$ is $C_2$-$C_6$ alkenyl. In another aspect, $R_6$ is

In another aspect, $R_6$ is $C_1$-$C_6$ alkyl. In another aspect, $R_6$ is

In another aspect, the compound is:

(doscadenamide S2)

(doscadenamide S3)

(doscadenamide S8)

or a pharmaceutically acceptable salt, solvate, hydrate, or prodrug thereof.

In another aspect, the compound is:

(doscadenamide S2)

(doscadenamide S3)

(doscadenamide S8)

or a pharmaceutically acceptable salt, solvate, hydrate, or prodrug thereof.

In another aspect, the compound is:

(doscadenamide S2)

(doscadenamide S3)

(doscadenamide S8)

(doscadenamdie S9)

or a pharmaceutically acceptable salt, solvate, hydrate, or prodrug thereof.

In another aspect, the invention is directed to a compound of Formula (VII):

(VII)

or a pharmaceutically acceptable salt, solvate, hydrate, or prodrug thereof;

<table>
<tr><td>43</td><td>44</td></tr>
</table> wherein $R_{13}$ is H, Boc, acetyl, Fmoc,

In another aspect, $R_7$ is $C_1$-$C_6$ alkyl. In another aspect, $R_7$ is

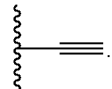

In another aspect, $R_{13}$ is

In another aspect $R_{14}$ is H. In another aspect, $R_{14}$ is $C_1$-$C_6$ alkyl. In another aspect, $R_{14}$ is Me. In another aspect, $R_6$ is $C_2$-$C_6$ alkynyl. In another aspect, $R_6$ is $R_{14}$ is H or $C_1$-$C_6$ alkyl;

$R_{15}$ is H or $C_1$-$C_6$ alkyl;

$R_6$ is H, $C_1$-$C_6$ alkyl, $C_2$-$C_6$ alkenyl, or $C_2$-$C_6$ alkynyl;

$R_8$ is H, Boc, acetyl, Fmoc, or

In another aspect, $R_6$ is $C_2$-$C_6$ alkenyl. In another aspect, $R_6$ is $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl. In another aspect, $R_8$ is In another aspect, $R_6$ is $C_1$-$C_6$ alkyl. In another aspect $R_6$ is In another aspect, $R_9$ is H. In another aspect, $R_{10}$ is $C_1$-$C_6$ alkyl. In another aspect, $R_9$ is H and $R_{10}$ is $C_1$-$C_6$ alkyl. In another aspect, $R_{10}$ is Me. In another aspect, $R_{10}$ is H. In another aspect, $R_9$ is $C_1$-$C_6$ alkyl. In another aspect, $R_{10}$ is H and $R_9$ is $C_1$-$C_6$ alkyl. In another aspect, $R_9$ is Me. In another aspect, $R_7$ is $C_2$-$C_6$ alkynyl. In another aspect, $R_7$ is In another aspect, $R_{13}$ is

In another aspect $R_{14}$ is H. In another aspect, $R_{14}$ is H and $R_{15}$ is $C_1$-$C_6$ alkyl. In another aspect, $R_{14}$ is H and $R_{15}$ is Me. In another aspect, $R_{15}$ is H. In another aspect, $R_{15}$ is H and $R_{14}$ is $C_1$-$C_6$ alkyl. In another aspect, $R_{15}$ is H and $R_{14}$ is Me. In another aspect, $R_6$ is $C_2$-$C_6$ alkynyl. In another aspect, $R_6$ is

In another aspect, $R_7$ is $C_2$-$C_6$ alkenyl. In another aspect, $R_7$ is

In another aspect, $R_6$ is $C_2$-$C_6$ alkenyl. In another aspect, $R_6$ is

In another aspect, $R_6$ is $C_1$-$C_6$ alkyl. In another aspect $R_6$ is

In another aspect, the compound of Formula (VII), or a pharmaceutically acceptable salt, solvate, hydrate, or prodrug thereof, is (doscadenamide S14), or a pharmaceutically acceptable salt, solvate, hydrate, or prodrug thereof.

In another aspect, the invention is directed to a compound of Formula (VIII):

(VIII)

or a pharmaceutically acceptable salt, solvate, hydrate, or prodrug thereof;

wherein $R_{16}$ is H, $C_1$-$C_6$ alkyl, $C_2$-$C_6$ alkenyl, or $C_2$-$C_6$ alkynyl; and $R_{17}$ is H or $C_1$-$C_6$ alkyl; or $R_{16}$ is H or $C_1$-$C_6$ alkyl; and $R_{17}$ is H, $C_1$-$C_6$ alkyl, $C_2$-$C_6$ alkenyl, or $C_2$-$C_6$ alkynyl. In another aspect, the compound is (doscadenamide S4)

or a pharmaceutically acceptable salt, solvate, hydrate, or prodrug thereof.

In another aspect, the invention is directed to a process to prepare a compound of Formula (X), 1f the process comprises:

a. alkylating a compound of formula, in the presence of a base and an alkylating agent; and b. hydrolyzing the product from step a. to afford the compound of Formula (X);

wherein $R_7$ is H, $C_1$-$C_6$ alkyl, $C_2$-$C_6$ alkenyl, or $C_2$-$C_6$ alkynyl; and

$R_{18}$ is $C_1$-$C_6$ alkyl. In another aspect, the compound in step a. is

In another aspect, the base in step a. is an alkyllithum, a lithium bis(trialkylsilyl)amide, a sodium bis(trialkylsilyl) amide, a potassium bis(trialkylsilyl)amide, a lithium dialkylamide, a lithium alkoxide, a sodium alkoxide, or a potassium alkoxide. In another aspect, the base in step a. is n-butyllithium, lithium amide, potassium amide, sodium amide, lithium bis(trimethylsilyl)amide, lithium diisopropylamide, potassium bis(trimethylsilyl)amide, sodium bis(t-rimethylsilyl)amide, potassium tert-butoxide, or sodium tert-butoxide. In another aspect, the base in step a. is lithium bis(trimethylsilyl)amide, lithium diisopropylamide, potassium bis(trimethylsilyl)amide, sodium bis(trimethylsilyl) amide. In another aspect, the base in step a. is sodium bis(trimethylsilyl)amide. In another aspect, the alkylating agent in step a. is an alkyl halide, a dialkyl sulfate, a dialkyl carbonate, or an alkyl triflate. In another aspect, the alkylating agent in step a. is methyl iodide, dimethyl sulfate, dimethyl carbonate, or methyl triflate. In another aspect, the alkylating agent in step a. is methyl iodide. In another aspect, the hydrolysis in step b. is conducted under basic conditions. In another aspect, the basic conditions include sodium hydroxide, lithium hydroxide, potassium hydroxide, sodium hydroperoxide, lithium hydroperoxide, or potassium hydroperoxide. In another aspect, the basic conditions include lithium hydroperoxide.

In another aspect, the invention is directed to a process to prepare a compound of Formula (XI), the process comprises:
  a. alkylating a compound of formula, in the presence of a base and an alkylating agent; and
b. hydrolyzing the product from step a. to afford the compound of Formula (XI);

wherein $R_7$ is H, $C_1$-$C_6$ alkyl, $C_2$-$C_6$ alkenyl, or $C_2$-$C_6$ alkynyl; and
$R_{18}$ is $C_1$-$C_6$ alkyl. In another aspect, the compound in step a. is In another aspect, the base in step a. is an alkyllithum, a lithium bis(trialkylsilyl)amide, a sodium bis(trialkylsilyl) amide, a potassium bis(trialkylsilyl)amide, a lithium dialkylamide, a lithium alkoxide, a sodium alkoxide, or a potassium alkoxide. In another aspect, the base in step a. is n-butyllithium, lithium amide, potassium amide, sodium amide, lithium bis(trimethylsilyl)amide, lithium diisopropylamide, potassium bis(trimethylsilyl)amide, sodium bis(t-rimethylsilyl)amide, potassium tert-butoxide, or sodium tert-butoxide. In another aspect, the base in step a. is lithium bis(trimethylsilyl)amide, lithium diisopropylamide, potassium bis(trimethylsilyl)amide, sodium bis(trimethylsilyl) amide. In another aspect, the base in step a. is sodium bis(trimethylsilyl)amide. In another aspect, the alkylating agent in step a. is an alkyl halide, a dialkyl sulfate, a dialkyl carbonate, or an alkyl triflate. In another aspect, the alkylating agent in step a. is methyl iodide, dimethyl sulfate, dimethyl carbonate, or methyl triflate. In another aspect, the alkylating agent in step a. is methyl iodide. In another aspect, the hydrolysis in step b. is conducted under basic conditions. In another aspect, the basic conditions include sodium hydroxide, lithium hydroxide, potassium hydroxide, sodium hydroperoxide, lithium hydroperoxide, or potassium hydroperoxide. In another aspect, the basic conditions include lithium hydroperoxide.

Methods of Treatment

In another aspect, the invention provides a method of modulating quorum sensing signaling, the method comprising administering an effective amount of a compound of Formula (IX):

(IX)

or a pharmaceutically acceptable salt, solvate, hydrate, or prodrug thereof;
  wherein $R_{13}$ is H, Boc, acetyl, Fmoc, R -continued each $R_{14}$ is independently H or $C_1$-$C_6$ alkyl;
$R_{15}$ is H or $C_1$-$C_6$ alkyl;
each $R_6$ is independently H, $C_1$-$C_6$ alkyl, $C_2$-$C_6$ alkenyl, or $C_2$-$C_6$ alkynyl;
$R_8$ is H, Boc, acetyl, Fmoc, or $R_7$ is H, $C_1$-$C_6$ alkyl, $C_2$-$C_6$ alkenyl, or $C_2$-$C_6$ alkynyl;
$R_9$ is H or $C_1$-$C_6$ alkyl; and
$R_{10}$ is H or $C_1$-$C_6$ alkyl. In another aspect, the modulation is activation. In another aspect, the modulation is inhibition. In another aspect, the compound is administered in vitro. In another aspect, the compound is administered in vivo. In another aspect, the method further comprises administering the compound to a subject.

In another aspect, the invention provides a method of modulating quorum sensing signaling, the method comprising administering an effective amount of a compound of Formula (VII):

(VII)

or a pharmaceutically acceptable salt, solvate, hydrate, or prodrug thereof;
wherein $R_{13}$ is H, Boc, acetyl, Fmoc, $R_{14}$ is H or $C_1$-$C_6$ alkyl;
$R_{15}$ is H or $C_1$-$C_6$ alkyl;
$R_6$ is H, $C_1$-$C_6$ alkyl, $C_2$-$C_6$ alkenyl, or $C_2$-$C_6$ alkynyl;
$R_8$ is H, Boc, acetyl, Fmoc, or $R_7$ is H, $C_1$-$C_6$ alkyl, $C_2$-$C_6$ alkenyl, or $C_2$-$C_6$ alkynyl;
$R_9$ is H or $C_1$-$C_6$ alkyl; and
$R_{10}$ is H or $C_1$-$C_6$ alkyl. In another aspect, the modulation is activation. In another aspect, the modulation is inhibition. In another aspect, the compound is administered in vitro. In another aspect, the compound is administered in vivo. In another aspect, the method further comprises administering the compound to a subject.

In another aspect, the invention provides a method of inhibiting bacterial growth, the method comprising administering an effective amount of a compound of Formula (IX):

(IX)

or a pharmaceutically acceptable salt, solvate, hydrate, or prodrug thereof;
wherein $R_{13}$ is H, Boc, acetyl, Fmoc, each $R_{14}$ is independently H or $C_1$-$C_6$ alkyl;
$R_{15}$ is H or $C_1$-$C_6$ alkyl;
each $R_6$ is independently H, $C_1$-$C_6$ alkyl, $C_2$-$C_6$ alkenyl, or $C_2$-$C_6$ alkynyl;
$R_8$ is H, Boc, acetyl, Fmoc, or $R_7$ is H, $C_1$-$C_6$ alkyl, $C_2$-$C_6$ alkenyl, or $C_2$-$C_6$ alkynyl;
$R_9$ is H or $C_1$-$C_6$ alkyl; and
$R_{10}$ is H or $C_1$-$C_6$ alkyl. In another aspect, the compound is administered in vitro. In another aspect, the compound is administered in vivo. In another aspect, the method further comprises administering the compound to a subject.

In another aspect, the invention provides a method of inhibiting bacterial growth, the method comprising administering an effective amount of a compound of Formula (VII):

(VII)

or a pharmaceutically acceptable salt, solvate, hydrate, or prodrug thereof;

wherein $R_{13}$ is H, Boc, acetyl, Fmoc, $R_{14}$ is H or $C_1$-$C_6$ alkyl;

$R_{15}$ is H or $C_1$-$C_6$ alkyl;

$R_6$ is H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl. In another aspect, the compound is administered in vitro. In another aspect, the compound is administered in vivo. In another aspect, the method further comprises administering the compound to a subject.

In another aspect, the invention provides a method of treating a bacterial infection in a subject, the method comprising administering an effective amount of a compound of Formula (IX):

(IX)

or a pharmaceutically acceptable salt, solvate, hydrate, or prodrug thereof;

wherein $R_{13}$ is H, Boc, acetyl, Fmoc, each $R_{14}$ is independently H or $C_1$-$C_6$ alkyl;

$R_{15}$ is H or $C_1$-$C_6$ alkyl;

each $R_6$ is independently H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl. In another aspect, the subject is a mammal. In another aspect, the subject is a human.

In another aspect, the invention provides a method of treating a bacterial infection in a subject in need thereof, the method comprising administering an effective amount of a compound of Formula (IX):

(IX)

or a pharmaceutically acceptable salt, solvate, hydrate, or prodrug thereof;

wherein $R_{13}$ is H, Boc, acetyl, Fmoc, each $R_{14}$ is independently H or $C_1$-$C_6$ alkyl;
$R_{15}$ is H or $C_1$-$C_6$ alkyl;
each $R_6$ is independently H, $C_1$-$C_6$ alkyl, $C_2$-$C_6$ alkenyl, or $C_2$-$C_6$ alkynyl;
$R_8$ is H, Boc, acetyl, Fmoc, or $R_7$ is H, $C_1$-$C_6$ alkyl, $C_2$-$C_6$ alkenyl, or $C_2$-$C_6$ alkynyl;
$R_9$ is H or $C_1$-$C_6$ alkyl; and
$R_{10}$ is H or $C_1$-$C_6$ alkyl. In another aspect, the subject is a mammal. In another aspect, the subject is a human.

In another aspect, the invention provides a method of treating a bacterial infection in a subject, the method comprising administering an effective amount of a compound of Formula (VII):

(VII)

or a pharmaceutically acceptable salt, solvate, hydrate, or prodrug thereof;
wherein $R_{13}$ is H, Boc, acetyl, Fmoc, $R_{14}$ is H or $C_1$-$C_6$ alkyl;
$R_{15}$ is H or $C_1$-$C_6$ alkyl;

54

$R_6$ is H, $C_1$-$C_6$ alkyl, $C_2$-$C_6$ alkenyl, or $C_2$-$C_6$ alkynyl;
$R_8$ is H, Boc, acetyl, Fmoc, or $R_7$ is H, $C_1$-$C_6$ alkyl, $C_2$-$C_6$ alkenyl, or $C_2$-$C_6$ alkynyl;
$R_9$ is H or $C_1$-$C_6$ alkyl; and
$R_{10}$ is H or $C_1$-$C_6$ alkyl. In another aspect, the subject is a mammal. In another aspect, the subject is a human.

In another aspect, the invention provides a method of treating a bacterial infection in a subject in need thereof, the method comprising administering an effective amount of a compound of Formula (VII):

(VII)

or a pharmaceutically acceptable salt, solvate, hydrate, or prodrug thereof;
wherein $R_{13}$ is H, Boc, acetyl, Fmoc, $R_{14}$ is H or $C_1$-$C_6$ alkyl;
$R_{15}$ is H or $C_1$-$C_6$ alkyl;
$R_6$ is H, $C_1$-$C_6$ alkyl, $C_2$-$C_6$ alkenyl, or $C_2$-$C_6$ alkynyl;
$R_8$ is H, Boc, acetyl, Fmoc, or $R_7$ is H, $C_1$-$C_6$ alkyl, $C_2$-$C_6$ alkenyl, or $C_2$-$C_6$ alkynyl;
$R_9$ is H or $C_1$-$C_6$ alkyl; and
$R_{10}$ is H or $C_1$-$C_6$ alkyl. In another aspect, the subject is a mammal. In another aspect, the subject is a human.

In certain embodiments, the bacterial infection is an infection caused by Gram-positive bacteria. In certain embodiments, the bacterial infection is an infection caused by Gram-negative bacteria. In certain embodiments, the bacterial infection is a *Staphylococcus* infection, a *Bacillus* infection, or an *Escherichia* infection. In some embodiments, the bacterial infection is caused by a member of Mycobacteriacae. In certain embodiments, the bacterial infection is an infection caused by *Mycobacterium tuberculosis*. In some embodiments, the infectious disease is tuberculosis. In certain embodiments, the bacterial infection is a mycobacterial infection. In some embodiments the bacterial infection is an atypical mycobacterial infection. In some embodiments, the infectious disease is tuberculosis. In some embodiments, the infectious disease is multi-drug resistant tuberculosis (MDR-TB). In some embodiments, the infectious disease is extensively drug-resistant tuberculosis (XDR-TB). In some embodiments, the bacterial infection is caused by a member of Staphylococcaceae. In certain embodiments, the bacterial infection is a *Staphylococcus* infection. In some embodiments, the bacterial infection is a *Staphylococcus aureus* infection. In some embodiments, the bacterial infection is a methicillin-resistant *Staphylococcus aureus* (MRSA) infection. In some embodiments, the bacterial infection is healthcare-associated MRSA (HA-MRSA). In some embodiments, the bacterial infection is community-associated MRSA (CA-MRSA). In some embodiments, the bacterial infection is a vancomycin-intermediate *Staphylococcus aureus* (VISA) infection or a vancomycin-resistant *Staphylococcus aureus* (VRSA) infection. In some embodiments, the bacterial infection is *B. anthracis*. In certain embodiments, the bacterial infection is *E. coli*.

Exemplary bacterial infections include, but are not limited to, infections with a Gram positive bacteria (e.g., of the phylum Actinobacteria, phylum Firmicutes, or phylum Tenericutes); Gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacteria is a member of the phylum Firmicutes and the genus *Enterococcus*, i.e., the bacterial infection is an *Enterococcus* infection. Exemplary Enterococci bacteria include, but are not limited to, *E. avium, E. durans, E. faecalis, E. faecium, E. gallinarum, E. solitarius, E. casseliflavus*, and *E. raffinosus*. In certain embodiments, the bacteria is a member of the phylum Firmicutes and the genus *Staphylococcus*, i.e., the bacterial infection is a *Staphylococcus* infection. Exemplary Staphylococci bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xylosus*. In certain embodiments, the *Staphylococcus* infection is a *S. aureus* infection. In certain embodiments, the *Staphylococcus* infection is a methicillin-resistant *Staphylococcus aureus* (MRSA) infection. In some embodiments, the *Staphylococ-*

*cus* infection is an vancomycin-intermediate *Staphylococcus aureus* (VISA) infection or a vancomycin-resistant *Staphylococcus aureus* (VRSA) infection.

In certain embodiments, the bacteria is a member of the phylum Firmicutes and the genus *Bacillus*, i.e., the bacterial infection is a *Bacillus* infection. Exemplary *Bacillus* bacteria include, but are not limited to, *B. alcalophilus, B. alvei, B. aminovorans, B. amyloliquefaciens, B. aneurinolyticus, B. anthracis, B. aquaemaris, B. atrophaeus, B. boroniphilus, B. brevis, B. caldolyticus, B. centrosporus, B. cereus, B. circulans, B. coagulans, B. firmus, B. flavothermus, B. fusiformis, B. globigii, B. infernus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis*, and *B. weihenstephanensis*. In certain embodiments, the *Bacillus* infection is a *B. subtilis* infection. In certain embodiments, the *B. subtilis* has an efflux (e.g., mef, msr) genotype. In certain embodiments, the *B. subtilis* has a methylase (e.g., erm) genotype. In certain embodiments, the *Bacillus* infection is a *B. anthracis* infection. In certain embodiments, the bacteria is a member of the phylum Firmicutes and the genus *Streptococcus*, i.e., the bacterial infection is a *Streptococcus* infection. Exemplary *Streptococcus* bacteria include, but are not limited to, *S. agalactiae, S. anginosus, S. bovis, S. canis, S. constellatus, S. dysgalactiae, S. equinus, S. iniae, S. intermedius, S. mitis, S. mutans, S. oralis, S. parasanguinis, S. peroris, S. pneumoniae, S. pyogenes, S. ratti, S. salivarius, S. thermophilus, S. sanguinis, S. sobrinus, S. suis, S. uberis, S. vestibularis, S. viridans*, and *S. zooepidemicus*. In certain embodiments, the *Streptococcus* infection is an *S. pyogenes* infection. In certain embodiments, the *Streptococcus* infection is an *S. pneumoniae* infection. In certain embodiments, the *S. pneumoniae* has an efflux (e.g., mef, msr) genotype. In certain embodiments, the *S. pneumoniae* has a methylase (e.g., erm) genotype. In certain embodiments, the bacteria is a member of the phylum Firmicutes and the genus *Clostridium*, i.e., the bacterial infection is a *Clostridium* infection. Exemplary Clostridia bacteria include, but are not limited to, *C. botulinum, C. difficile, C. perfringens, C. tetani*, and *C. sordellii*.

In certain embodiments, the Gram negative bacteria is a bacteria of the phylum Proteobacteria and the genus *Escherichia*. i.e., the bacterial infection is an *Escherichia* infection. Exemplary *Escherichia* bacteria include, but are not limited to, *E. albertii, E. blattae, E. coli, E. fergusonii, E. hermannii*, and *E. vulneris*. In certain embodiments, the *Escherichia* infection is an *E. coli* infection. In certain embodiments, the Gram negative bacteria is a bacteria of the phylum Proteobacteria and the genus *Haemophilus*. i.e., the bacterial infection is an *Haemophilus* infection. Exemplary *Haemophilus* bacteria include, but are not limited to, *H. aegyptius, H. aphrophilus, H. avium, H. ducreyi, H. felis, H. haemolyticus, H. influenzae, H. parainfluenzae, H. paracuniculus, H. parahaemolyticus, H. pittmaniae, Haemophilus segnis*, and *H. somnus*. In certain embodiments, the *Haemophilus* infection is an *H. influenzae* infection.

In certain embodiments, the Gram negative-bacteria is a bacteria of the phylum Proteobacteria and the genus *Acinetobacter*. i.e., the bacterial infection is an *Acinetobacter* infection. Exemplary *Acinetobacter* bacteria include, but are not limited to, *A. baumanii, A. haemolyticus*, and *A. lwoffii*. In certain embodiments, the *Acinetobacter* infection is an *A. baumanii* infection. In certain embodiments, the Gram-negative bacteria is a bacteria of the phylum Proteobacteria and the genus *Klebsiella*. i.e., the bacterial infection is a *Klebsiella* infection. Exemplary *Klebsiella* bacteria include, but are not limited to, *K. granulomatis, K. oxytoca, K. michiganensis, K. pneumoniae, K. quasipneumoniae*, and *K. variicola*. In certain embodiments, the *Klebsiella* infection is a *K. pneumoniae* infection. In certain embodiments, the Gram-negative bacteria is a bacteria of the phylum Proteobacteria and the genus *Pseudomonas*. i.e., the bacterial infection is a *Pseudomonas* infection. Exemplary *Pseudomonas* bacteria include, but are not limited to, *P. aeruginosa, P. oryzihabitans, P. plecoglissicida, P. syringae, P. putida*, and *P. fluoroscens*. In certain embodiments, the *Pseudomonas* infection is a *P. aeruginosa* infection. In certain embodiments, the Gram-negative bacteria is a bacteria of the phylum Bacteroidetes and the genus *Bacteroides*. i.e., the bacterial infection is a *Bacteroides* infection. Exemplary *Bacteroides* bacteria include, but are not limited to, *B. fragilis, B. distasonis, B. ovatus, B. thetaiotaomicron*, and *B. vulgatus*. In certain embodiments, the *Bacteroides* infection is a *B. fragilis* infection. In certain embodiments, the Gram negative-bacteria is a bacteria of the phylum Proteobacteria and the genus *Yersinia*. i.e., the bacterial infection is an *Yersinia* infection. Exemplary *Yersinia* bacteria include, but are not limited to, *Y. pestis, Y. entercolitica*. and *Y. pseudo-tuberculosis*. In certain embodiments, the *Acinetobacter* infection is an *Y. pestis* infection.

In certain embodiments, the bacterial infection is caused by a bacteria of the phylum Actinobacteria. Exemplary bacteria of the phylum include, but are not limited to bacteria within Acidimicrobiaceae family, Actinomycetaceae family, Corynebacteriaceae family, Gordoniaceae family, Mycobacteriaceae family, Nocardiaceae family, Tsukamurellaceae family, Williamsiaceae family, Acidothermaceae family, Frankiaceae family, Geodermatophilaceae, Kineosporiaceae, Microsphaeraceae family, Sporichthyaceae family, Glycomycetaceae family, Beutenbergiaceae family, Bogoriellaceae family, Brevibacteriaceae family, Cellulomonadaceae family, Dermabacteraceae family, Dermatophilaceae family, Dermacoccaceae family, Intrasporangiaceae family, Jonesiaceae family, Microbacteriaceae family, Micrococcaceae family, Promicromonosporaceae family, Rarobacteraceae family, Sanguibacteraceae family, Micromonosporaceae family, Nocardioidaceae family, Propionibacteriaceae family, Actinosynnemataceae family, Pseudonocardiaceae family, Streptomycetaceae family, Nocardiopsaceae family, Streptosporangiaceae family, Thermomonosporaceae family, Bifidobacteriaceae family, Coriobacteriaceae family, Rubrobacteraceae family, and Sphaerobacteraceae family.

In certain embodiments, the bacteria is a member of the phylum Actinobacteria and the *Mycobacterium*. In some embodiments the bacteria is a baceteria associated with an atypical mycobacterial infection. Exemplary bacteria from genus *Mycobacterium* include, but are not limited to: *M. abscessus, M. africanum, M. avium, M. bovis, M. caprae, M. canetti, M. chelonae, M. colombiense, M. flavescens, M. fortuitum, M. genavense, M. gordonae, M. haemophilum, M. intracellulare, M. kansasii, M. leprae, M. lepramatosis, M. malmoense, M. marinum, M. microti, M. parafortuitum, M. phlei, M. pinnipedii, M. scrofulaceum, M. simiae, M. smegmatis, M. szulgai, M. terrae, M. ulcerans, M. vaccae*, and *M. xenope*. In some embodiments, the bacteria is a bacteria that can cause tuberculosis (e.g., a member of the *Mycobacterium tuberculosis* complex (e.g., *M. tuberculosis, M. africanum, M. bovis, M bovis* BCG, *M. microti, M. canetti, M pinnipedii, M. suricattae, M. mungi*). In some embodiments, the bacteria is *M. tuberculosis*. In some embodiments, the bacteria is a member of the *Mycobacterium avium* complex (e.g., *M. avium, M. avium, M. avium* paratuberculosis, *M. avium silvaticum, M. avium hominissuis, M. colombiense, M. indicus pranii, M. intracellulare*). In some embodiments, the bacteria is *M. phlei*. In some embodiments, the bacteria is *M. smegmatis*. In certain embodiments, the *Mycobacterium* infection is a *M. tuberculosis* infection. In certain embodiments, the *Mycobacterium* infection is a multi-drug-resistant tuberculosis (MDR-TB) infection or extensively drug-resistant tuberculosis (XDR-TB) infection. In certain embodiments, the *M. tuberculosis* infection is a multi-drug-resistant tuberculosis (MDR-TB) infection or extensively drug-resistant tuberculosis (XDR-TB) infection.

In certain embodiments, the bacterial infection is a *Mycobacterium* infection, a *Staphylococcus* infection, *Pseudomonas* infection, a *Bacillus* infection, or an *Escherichia* infection. In certain, embodiments, the bacterial infection is tuberculosis. In some embodiments, the bacterial infection is a *Mycobacterium tuberculosis* infection. In certain embodiments, the bacterial infection is a *Pseudomonas* infection. In some embodiments, the bacterial infection is *Pseudomonas aeruginosa* infection. In some embodiments, the bacterial infection is *Yersinia* infection. In some embodiments the bacterial infection is *Yersinia pestis* infection. In some embodiments the bacterial infection is *E. coli* infection. In some embodiments the bacterial infection is *Bacillus anthracis* infection. In some embodiments the bacterial infection is *Bacillus anthracis* infection. In some embodiments the bacterial infection is *Vibrio cholera* infection. In some embodiments, the bacterial infection is infection of multiple species of bacterium. In some embodiments, the bacterial infection is infection of multiple species of bacterium, one of which is *P. aeruginosa*. In some embodiments, the bacterial infection is infection of multiple species of bacterium, one of which is *Mycobacterium tuberculosis*.

In another aspect, the invention provides a method of treating cancer in a subject, the method comprising administering an effective amount of a compound of Formula (IX):

(IX)

or a pharmaceutically acceptable salt, solvate, hydrate, or prodrug thereof;

wherein $R_{13}$ is H, Boc, acetyl, Fmoc, $R_6$, or

59

-continued each $R_{14}$ is independently H or $C_1$-$C_6$ alkyl;

$R_{15}$ is H or $C_1$-$C_6$ alkyl;

each $R_6$ is independently H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl. In another aspect, the subject is a mammal. In another aspect, the subject is a human.

In another aspect, the invention provides a method of treating cancer in a subject in need thereof, the method comprising administering an effective amount of a compound of Formula (IX):

(IX)

or a pharmaceutically acceptable salt, solvate, hydrate, or prodrug thereof;

wherein $R_{13}$ is H, Boc, acetyl, Fmoc, each $R_{14}$ is independently H or $C_1$-$C_6$ alkyl;

$R_{15}$ is H or $C_1$-$C_6$ alkyl;

each $R_6$ is independently H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl. In another aspect, the subject is a mammal. In another aspect, the subject is a human.

In another aspect, the invention provides a method of treating cancer in a subject, the method comprising administering an effective amount of a compound of Formula (VII):

(VII)

or a pharmaceutically acceptable salt, solvate, hydrate, or prodrug thereof;

wherein $R_{13}$ is H, Boc, acetyl, Fmoc, $R_{14}$ is H or $C_1$-$C_6$ alkyl; $R_{15}$ is H or $C_1$-$C_6$ alkyl;

$R_6$ is H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl. In another aspect, the subject is a mammal. In another aspect, the subject is a human.

In another aspect, the invention provides a method of treating cancer in a subject in need thereof, the method comprising administering an effective amount of a compound of Formula (VII):

61

(VII)

or a pharmaceutically acceptable salt, solvate, hydrate, or prodrug thereof;

wherein $R_{13}$ is H, Boc, acetyl, Fmoc, $R_{14}$ is H or $C_1$-$C_6$ alkyl;
$R_{15}$ is H or $C_1$-$C_6$ alkyl;
$R_6$ is H, $C_1$-$C_6$ alkyl, $C_2$-$C_6$ alkenyl, or $C_2$-$C_6$ alkynyl;
$R_8$ is H, Boc, acetyl, Fmoc, or $R_7$ is H, $C_1$-$C_6$ alkyl, $C_2$-$C_6$ alkenyl, or $C_2$-$C_6$ alkynyl;
$R_9$ is H or $C_1$-$C_6$ alkyl; and
$R_{10}$ is H or $C_1$-$C_6$ alkyl. In another aspect, the subject is a mammal. In another aspect, the subject is a human.

In another aspect, the cancer is cancer of the colon, breast, bone, brain and others (e.g., osteosarcoma, neuroblastoma, colon adenocarcinoma), chronic myelogenous leukemia (CML), acute myeloid leukemia (AML), acute promyelocytic leukemia (APL), comprising administering to said subject in need thereof, an effective amount of a compound delineated herein (e.g., any of the formulae herein), or a pharmaceutically acceptable salt thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

In another aspect, the invention provides a method of increasing the effectiveness of anti-cancer therapy in a subject currently being administered one or more anti-cancer therapies, the method comprising administering an effective amount of a compound of Formula (IX):

(IX)

or a pharmaceutically acceptable salt, solvate, hydrate, or prodrug thereof;

wherein $R_{13}$ is H, Boc, acetyl, Fmoc, $R_6$, each $R_{14}$ is independently H or $C_1$-$C_6$ alkyl;
$R_{15}$ is H or $C_1$-$C_6$ alkyl;
each $R_6$ is independently H, $C_1$-$C_6$ alkyl, $C_2$-$C_6$ alkenyl, or $C_2$-$C_6$ alkynyl;
$R_8$ is H, Boc, acetyl, Fmoc, or $R_7$ is H, $C_1$-$C_6$ alkyl, $C_2$-$C_6$ alkenyl, or $C_2$-$C_6$ alkynyl;
$R_9$ is H or $C_1$-$C_6$ alkyl; and
$R_{10}$ is H or $C_1$-$C_6$ alkyl. In another aspect, the subject is a mammal. In another aspect, the subject is a human.

In another aspect, the invention provides a method of increasing the effectiveness of anti-cancer therapy in a subject currently being administered one or more anti-cancer therapies, the method comprising administering an effective amount of a compound of Formula (VII):

(VII)

or a pharmaceutically acceptable salt, solvate, hydrate, or prodrug thereof;

wherein $R_{13}$ is H, Boc, acetyl, Fmoc, $R_6$, or $R_6$;

$R_{14}$ is H or $C_1$-$C_6$ alkyl;
$R_{15}$ is H or $C_1$-$C_6$ alkyl;
$R_6$ is H, $C_1$-$C_6$ alkyl, $C_2$-$C_6$ alkenyl, or $C_2$-$C_6$ alkynyl;
$R_8$ is H, Boc, acetyl, Fmoc, or

;

$R_7$ is H, $C_1$-$C_6$ alkyl, $C_2$-$C_6$ alkenyl, or $C_2$-$C_6$ alkynyl;
$R_9$ is H or $C_1$-$C_6$ alkyl; and
$R_{10}$ is H or $C_1$-$C_6$ alkyl. In another aspect, the subject is a mammal. In another aspect, the subject is a human.

In another aspect, the anti-cancer therapy is an anti-cancer agent, chemotherapeutic agent, an anti-angiogenesis agent, cytotoxic agent, or an anti-proliferation agent. Examples of such agents include but are not limited to TRAIL, TRAIL receptor agonists, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahway, N.J., 1987). In certain embodiments, the anti-cancer therapy is TRAIL or a TRAIL receptor agonist. In certain embodiments, the anti-cancer therapy is TRAIL. In certain embodiments, the anti-cancer therapy is a TRAIL receptor agonist.

In another aspect, the invention provides a method of increasing the effectiveness of anti-bacterial therapy in a subject currently being administered one or more anti-bacterial therapies, the method comprising administering an effective amount of a compound of Formula (IX):

(IX)

or a pharmaceutically acceptable salt, solvate, hydrate, or prodrug thereof;

wherein $R_{13}$ is H, Boc, acetyl, Fmoc, $R_6$, or $R_6$;

each $R_{14}$ is independently H or $C_1$-$C_6$ alkyl;
$R_{15}$ is H or $C_1$-$C_6$ alkyl;
each $R_6$ is independently H, $C_1$-$C_6$ alkyl, $C_2$-$C_6$ alkenyl, or $C_2$-$C_6$ alkynyl;
$R_8$ is H, Boc, acetyl, Fmoc, or

;

$R_7$ is H, $C_1$-$C_6$ alkyl, $C_2$-$C_6$ alkenyl, or $C_2$-$C_6$ alkynyl;
$R_9$ is H or $C_1$-$C_6$ alkyl; and
$R_{10}$ is H or $C_1$-$C_6$ alkyl. In another aspect, the disease is cancer. In another aspect, the subject is a mammal. In another aspect, the subject is a human.

In another aspect, the invention provides a method of increasing the effectiveness of anti-bacterial therapy in a subject currently being administered one or more antibacterial therapies, the method comprising administering an effective amount of a compound of Formula (VII):

$$\text{(VII)}$$

or a pharmaceutically acceptable salt, solvate, hydrate, or prodrug thereof;

wherein $R_{13}$ is H, Boc, acetyl, Fmoc, $R_{14}$ is H or $C_1$-$C_6$ alkyl;
$R_{15}$ is H or $C_1$-$C_6$ alkyl;
$R_6$ is H, $C_1$-$C_6$ alkyl, $C_2$-$C_6$ alkenyl, or $C_2$-$C_6$ alkynyl;
$R_8$ is H, Boc, acetyl, Fmoc, or $R_7$ is H, $C_1$-$C_6$ alkyl, $C_2$-$C_6$ alkenyl, or $C_2$-$C_6$ alkynyl;
$R_9$ is H or $C_1$-$C_6$ alkyl; and
$R_{10}$ is H or $C_1$-$C_6$ alkyl. In another aspect, the disease is cancer. In another aspect, the subject is a mammal. In another aspect, the subject is a human.

Exemplary anti-bacterial therapies include but are not limited to gentamicin, amikacin, tobramycin, ciprofloxacin, levofloxacin, ceftazidimine, cefepime, cefoperazone, cefpirome, ceftobiprole, carbenicllin, ticarcillin, mezlocillin, azlocillin, piperacillin, meropenem, imipenem, doripenem, polymyxin B, colistin, aztreonam, isoniazid, rifampicin (also called rifampin), pyrazinamide, ethambutol, strepto-mycin, moxifloxacin, gatifloxacin, amikacin, capremycin, kanamycin, ethionamide, prothionamide, cycloserine, teriz-idone, linezolide, clofazimine, pretomanid, bedaquiline, delamanid, or rifamycins. In certain embodiments, the addi-tional pharmaceutical agent is isoniazid, rifampicin (also called rifampin), pyrazinamide, ethambutol, or streptomy-cin. In some embodiments, the additional pharmaceutical agent is levofloxacin, moxifloxacin, gatifloxacin, amikacin, capremycin, kanamycin, ethionamide, prothionamide, cycloserine, terizidone, linezolide, or clofazimine.

In certain embodiments, the subject is a mammal, pref-erably a primate or human.

Methods delineated herein include those wherein the subject is identified as in need of a particular stated treat-ment. Identifying a subject in need of such treatment can be in the judgment of a subject or a health care professional and can be subjective (e.g. opinion) or objective (e.g. measurable by a test or diagnostic method).

In another embodiment, the invention provides a method as described above, wherein the effective amount of the compound of any of the formulae herein ranges from about 0.005 µg/kg to about 200 mg/kg. In certain embodiments, the effective amount of the compound of any of the formulae herein ranges from about 0.1 mg/kg to about 200 mg/kg. In a further embodiment, the effective amount of compound of any of the formulae herein ranges from about 10 mg/kg to 100 mg/kg.

In other embodiments, the invention provides a method as described above wherein the effective amount of the com-pound of any of the formulae herein ranges from about 1.0 pM to about 500 nM. In certain embodiments, the effective amount ranges from about 10.0 pM to about 1000 pM. In another embodiment, the effective amount ranges from about 1.0 nM to about 10 nM.

In another embodiment, the invention provides a method as described above, wherein the compound of any of the formulae herein is administered intravenously, intramuscu-larly, subcutaneously, intracerebroventricularly, orally or topically.

In other embodiments, the invention provides a method as described above, wherein the compound of any of the formulae herein is administered alone or in combination with one or more other therapeutics. In a further embodi-ment, the additional therapeutic agent is an anti-bacterial agent. Examples of such anti-bacterial agents include but are not limited to gentamicin, amikacin, tobramycin, ciprofloxa-cin, levofloxacin, ceftazidimine, cefepime, cefoperazone, cefpirome, ceftobiprole, carbenicllin, ticarcillin, mezlocillin, azlocillin, piperacillin, meropenem, imipenem, doripenem, polymyxin B, colistin, aztreonam, isoniazid, rifampicin (also called rifampin), pyrazinamide, ethambutol, strepto-mycin, moxifloxacin, gatifloxacin, amikacin, capremycin, kanamycin, ethionamide, prothionamide, cycloserine, teriz-idone, linezolide, clofazimine, pretomanid, bedaquiline, delamanid, or rifamycins. In certain embodiments, the addi-tional pharmaceutical agent is isoniazid, rifampicin (also called rifampin), pyrazinamide, ethambutol, or streptomy-cin. In some embodiments, the additional pharmaceutical agent is levofloxacin, moxifloxacin, gatifloxacin, amikacin, capremycin, kanamycin, ethionamide, prothionamide, cycloserine, terizidone, linezolide, or clofazimine.

In other embodiments, the invention provides a method as described above, wherein the compound of any of the formulae herein is administered alone or in combination with one or more other therapeutics. In a further embodi-ment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epi-rubicin, idarubicin, esorubicin, bleomycin, mafosfamide, ifosfamide, cytosine arabinoside, bis-chloroethylnitrosurea, busulfan, mitomycin C, actinomycin D, mithramycin, pred-nisone, hydroxyprogesterone, testosterone, tamoxifen, dac-arbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahway, N.J., 1987).

Another object of the present invention is the use of a compound as described herein (e.g., of any formulae herein) in the manufacture of a medicament for use in the treatment of a disorder or disease (e.g., cancer or bacterial infection). Another object of the present invention is the use of a compound as described herein (e.g., of any formulae herein) for use in the treatment of a disorder or disease (e.g., cancer or bacterial infection).

Pharmaceutical Compositions

In one aspect, the invention provides a pharmaceutical composition comprising the compound of any of the formulae herein (e.g., Formulae (I)-(IX)) or pharmaceutically acceptable salt thereof, and a pharmaceutically acceptable carrier. In another aspect, the composition further comprises an additional agent. In another aspect, the additional agent is an anti-bacterial agent. In another aspect, the additional agent is an anti-cancer agent.

In one aspect, the invention provides a kit comprising an effective amount of a compound of any of the formulae herein (e.g., Formulae (I)-(IX)), in unit dosage form, together with instructions for administering the compound to a subject suffering from or susceptible to a bacterial infection.

In one aspect, the invention provides a kit comprising an effective amount of a compound of any of the formulae herein (e.g., Formulae (I)-(IX)), in unit dosage form, together with instructions for administering the compound to a subject suffering from or susceptible to cancer.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific apratoxin compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch;

cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

General Experimental Procedures

All commercial reagents were used without further purification unless otherwise noted. Solvents were purified according to the guidelines in *Purification of Laboratory Chemicals* (5th edition, W. L. F. Armarego, Christina L. L. Chai, Butterworth-Heinemann: Oxford, 2003). Tetrahydrofuran (THF), $CH_2Cl_2$, DMF were purified by MS-PD5 solvent purification system (Innovation Inc.). All reactions were performed in heat-gun dried flasks (400° C. under reduced pressure) under an inert atmosphere of anhydrous Ar unless otherwise noted. Thin layer chromatography was performed on EMD silica gel 60 Å $F_{254}$ glass plates and preparative thin layer chromatography was performed on Whatman silica gel 60 Å $F_{254}$ glass plates (layer thick 1000 μm). Flash column chromatography was performed with Fisher 170-400 mesh silica gel. Nuclear magnetic resonance (NMR) spectra were recorded on a Bruker Avance III 500 spectromer, a Bruker Avance III 600 MHz spectrometer or a Bruker Avance Neo-600 spectrometer with a broadband Prodigy cryogenic probe. Chemical shifts for proton nuclear magnetic resonance ($^1$H NMR) spectra are reported in parts per million relative to the signal residual $CDCl_3$ at 7.26 ppm; Chemicals shifts for carbon nuclear magnetic resonance ($^{13}$C NMR) spectra are reported in parts per million relative to the center line of the $CDCl_3$ triplet at 77.16 ppm; The abbreviations s, d, dd, ddd, dddd, t, q, p, br, and m stand for the resonance multiplicity singlet, doublet, doublet of doublets, doublet of doublet of doublets, doublet of doublet of doublet of doublets, triplet, quartet, pentet, broad and multiplet, respectively. Optical rotation was measured on a Perkin-Elmer 341 polarimeter (Na D line) using a microcell of 1 dm path length. HRMS was conducted using a Thermo Fisher Q Exactive Focus mass spectrometer equipped with UltiMate™ 3000 RSLCnano System and electrospray probe on Universal Ion Max API source. Fluorescence and UV were measured on a SpectraMax M5 (Molecular Devices).

Isolation of Doscadenamide A

Figure 1:
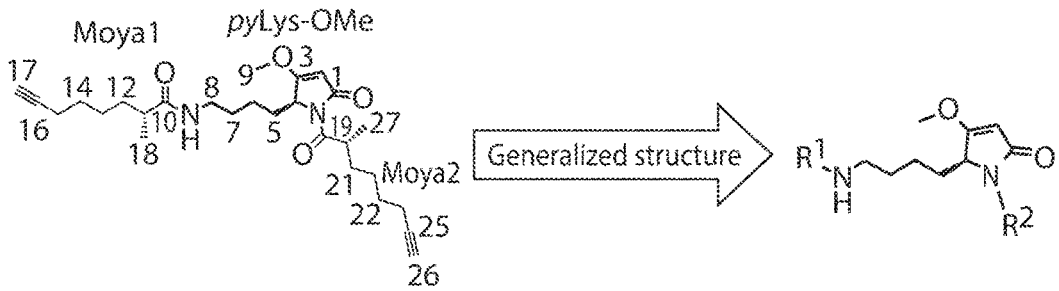
FIG. 1. depicts the structures of doscadenamides A-J and doscadenamides S4-S15.
Figure 1:
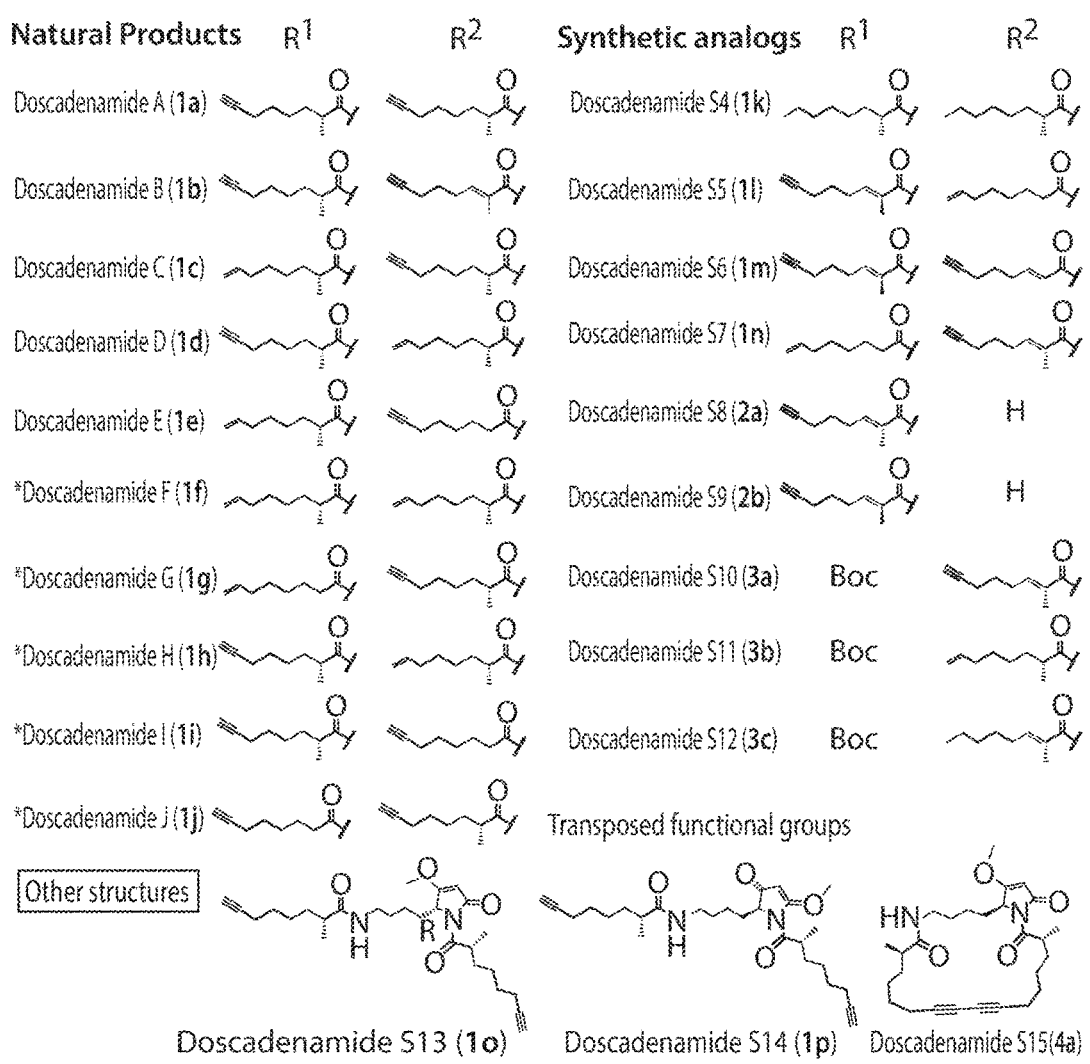

A cyanobacterium *Moorea bouillonii* sample was collected at Finger's Reef, Guam and previous investigation of this sample has led to the isolation of apratoxin A, lyngbyaloside, 2-epi-lyngbyaloside, 18E-lyngbyaloside C, 18Z-lyngbyaloside C, and apratyramide [Luesch, H.; Yoshida, W. Y.; Moore, R. E.; Paul, V. J.; Corbett, T. H. *J. Am. Chem. Soc.* 2001, 123, 5418-5423; Matthew, S.; Salvador, L. A.; Schupp, P. J.; Paul, V. J.; Luesch, H., *J. Nat. Prod.* 2010, 73 (9), 1544-1552; Cai, W.; Salvador-Reyes, L. A.; Zhang, W.; Chen, Q. Y.; Matthew, S.; Ratnayake, R.; Seo, S. J.; Dolles, S.; Gibson, D. J.; Paul, V. J.; Luesch, H., *ACS Chem. Biol.* 2018, 13 (1), 91-99]. The cyanobacterial sample was fractionated as described previously and the isolation was achieved by silica gel column chromatography and several rounds of reversed-phase HPLC to yield doscadenamide A (1a), as illustrated in FIG. 1 {white solid, $[\alpha]^{20}{}_D$ 40 (c 0.07, MeOH)} [Matthew, S.; Salvador, L. A.; Schupp, P. J.; Paul, V. J.; Luesch, H., *J. Nat. Prod.* 2010, 73 (9), 1544-1552]. Specifically, the sample of the *Moorea bouillonii* cyanobacterium was extracted with $CH_2Cl_2$ and MeOH (2:1) and the extract (10 g) was fractionated using column chromatography on silica gel, eluting with $CH_2Cl_2$ containing increasing concentrations of iPrOH to afford 16 fractions. Fractions 3, 4 and 5 (2% iPrOH in $CH_2Cl_2$; 400 mg, 1.54 g and 100 mg) and fractions 6 (5% iPrOH in $CH_2Cl_2$; 71 mg) were individually subjected to semipreparative HPLC (Phenomenex Phenyl-hexyl, 250×10 mm, 5μ, 2.0 mL/min; PDA detection) using a MeOH—$H_2O$ linear gradient (90-100% MeOH in 30 min and 100% MeOH for 10 min). Fractions were pooled based on retention times, ${}^1H$ NMR analysis, and low-resolution MS measurements to afford impure doscadenamide A (1a)-containing fractions. These fractions were further purified with HPLC (Ultracarb, 250×10 mm, 5, 2.0 mL/min; PDA detection) using a MeOH—$H_2O$ linear gradient (90-100% MeOH in 30 min and 100% MeOH for 10 min) to afford doscadenamide A (1a, $t_R$=10.0 min, 4.5 mg).

Structural Elucidation of Doscadenamide A

Figure 2:
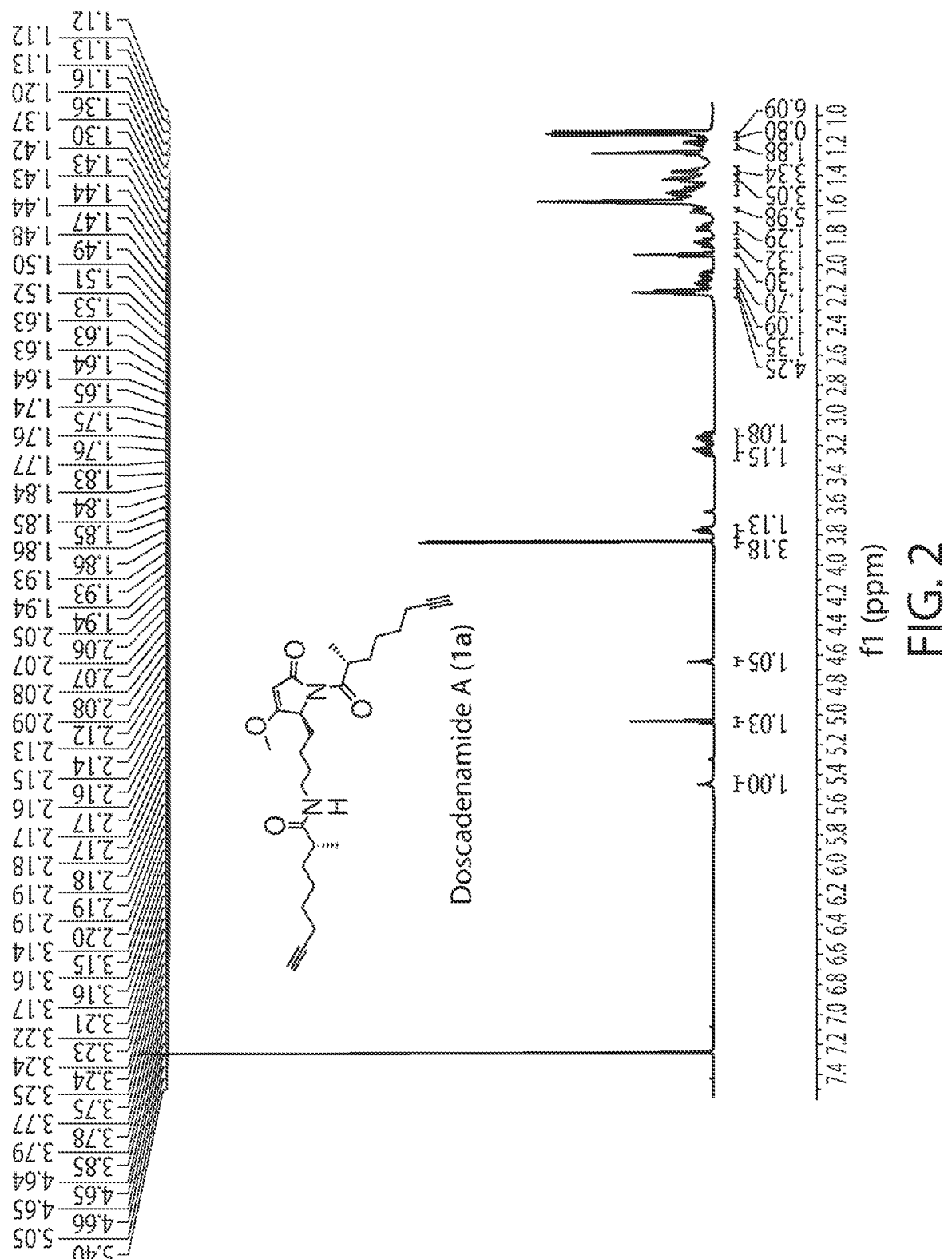
FIG. 2. depicts the $^1$H NMR spectrum of doscadenamide A (1a) in CDCl$_3$ (600 MHz) at 27° C.
Figure 3:
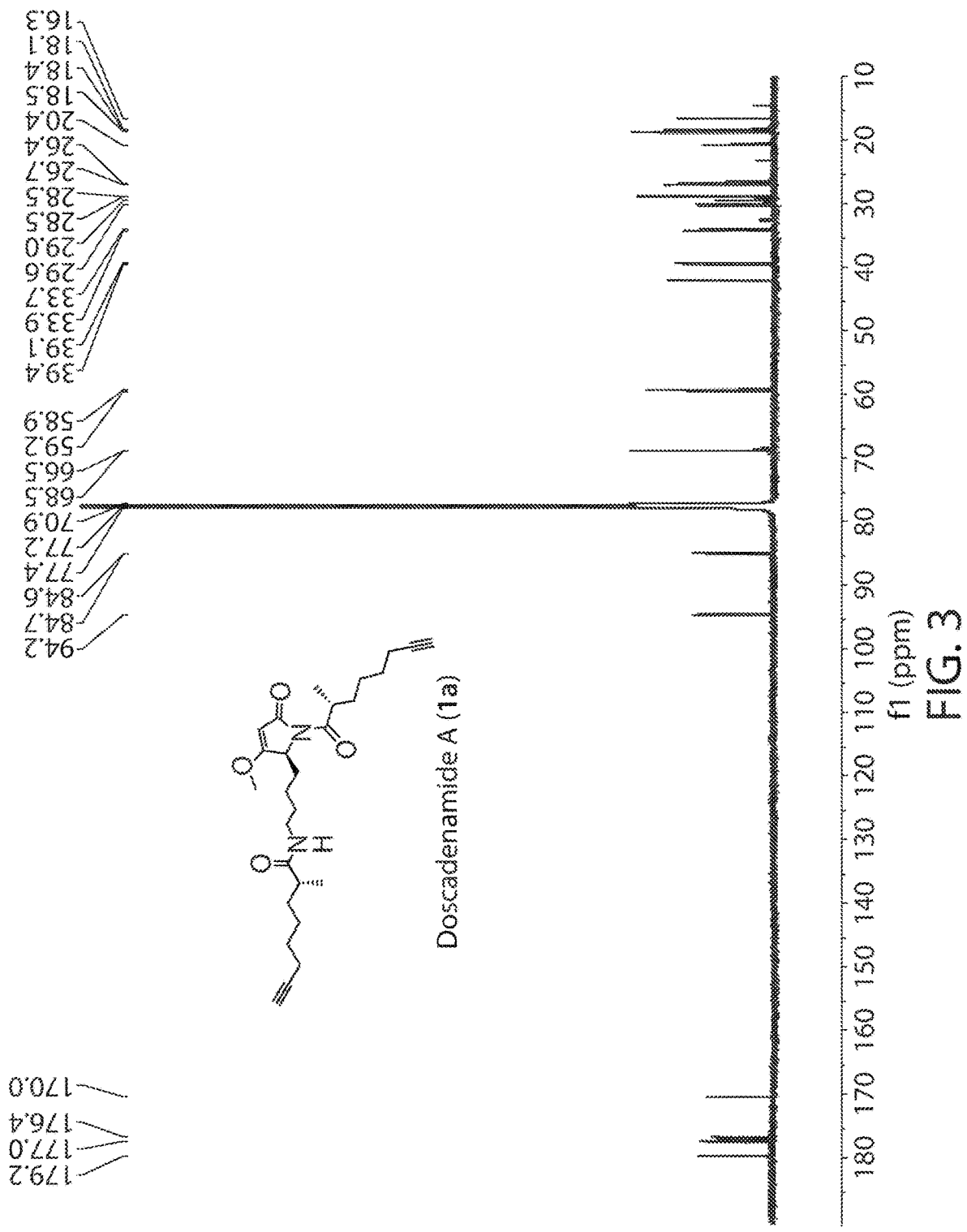
FIG. 3. depicts the $^{13}$C NMR spectrum of doscadenamide A (1a) in CDCl$_3$ (150 MHz) at 27° C.
Figure 4:
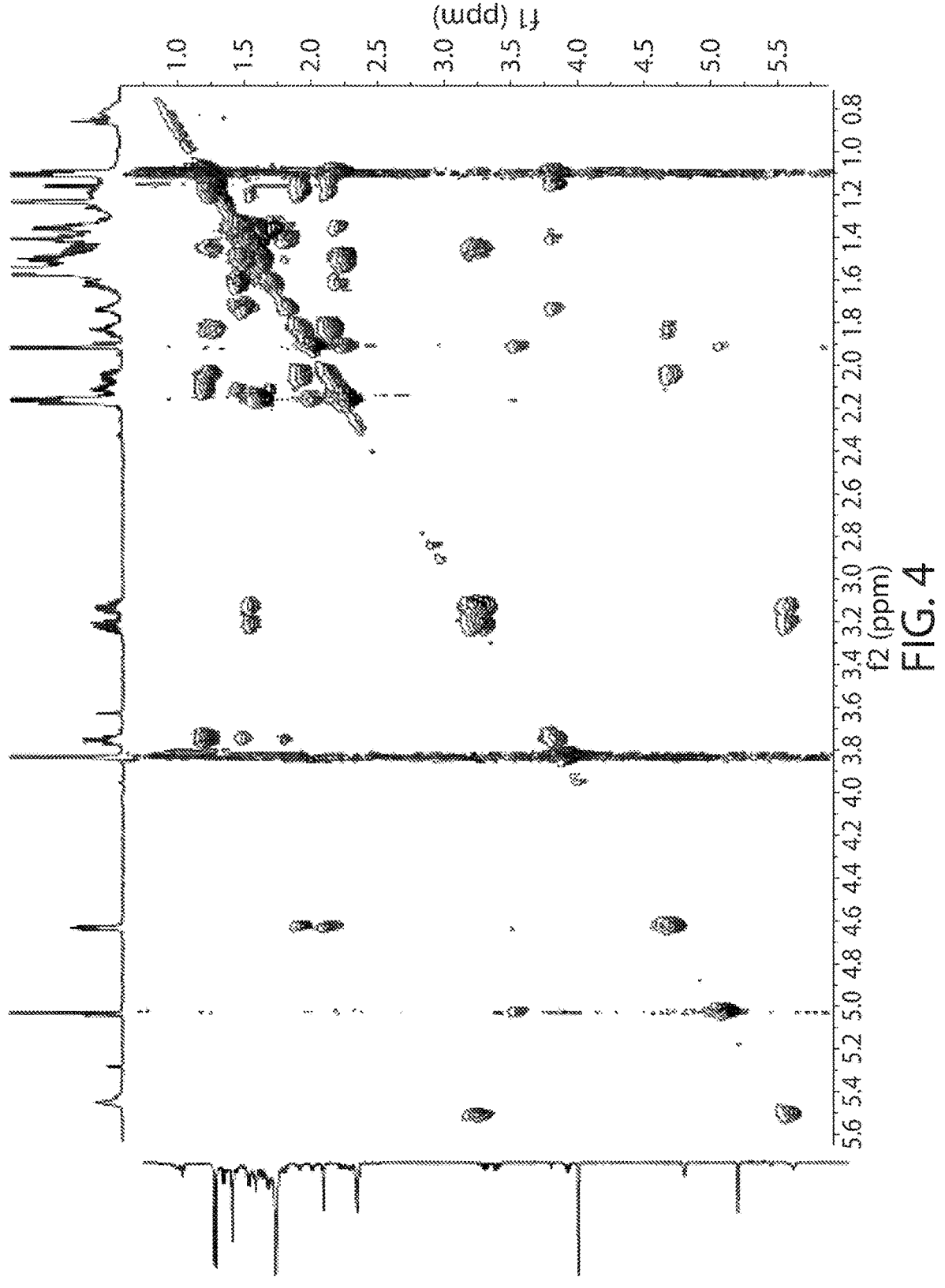
FIG. 4. depicts the COSY spectrum of doscadenamide A (1a) in CDCl$_3$ (600 MHz) at 27° C.
Figure 5:
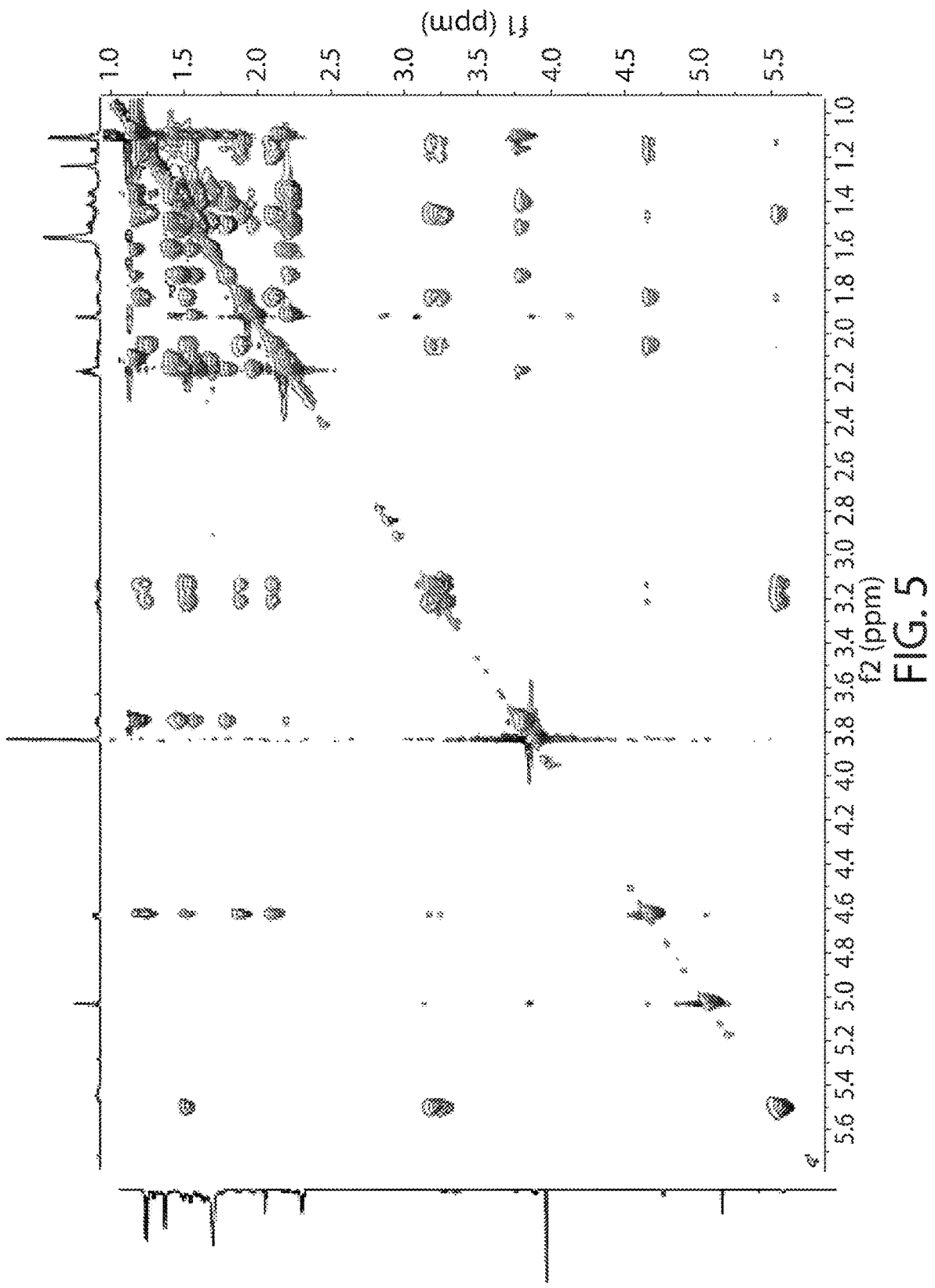
FIG. 5. depicts the TOCSY spectrum of doscadenamide A (1a) in CDCl$_3$ (600 MHz) at 27° C.
Figure 6:
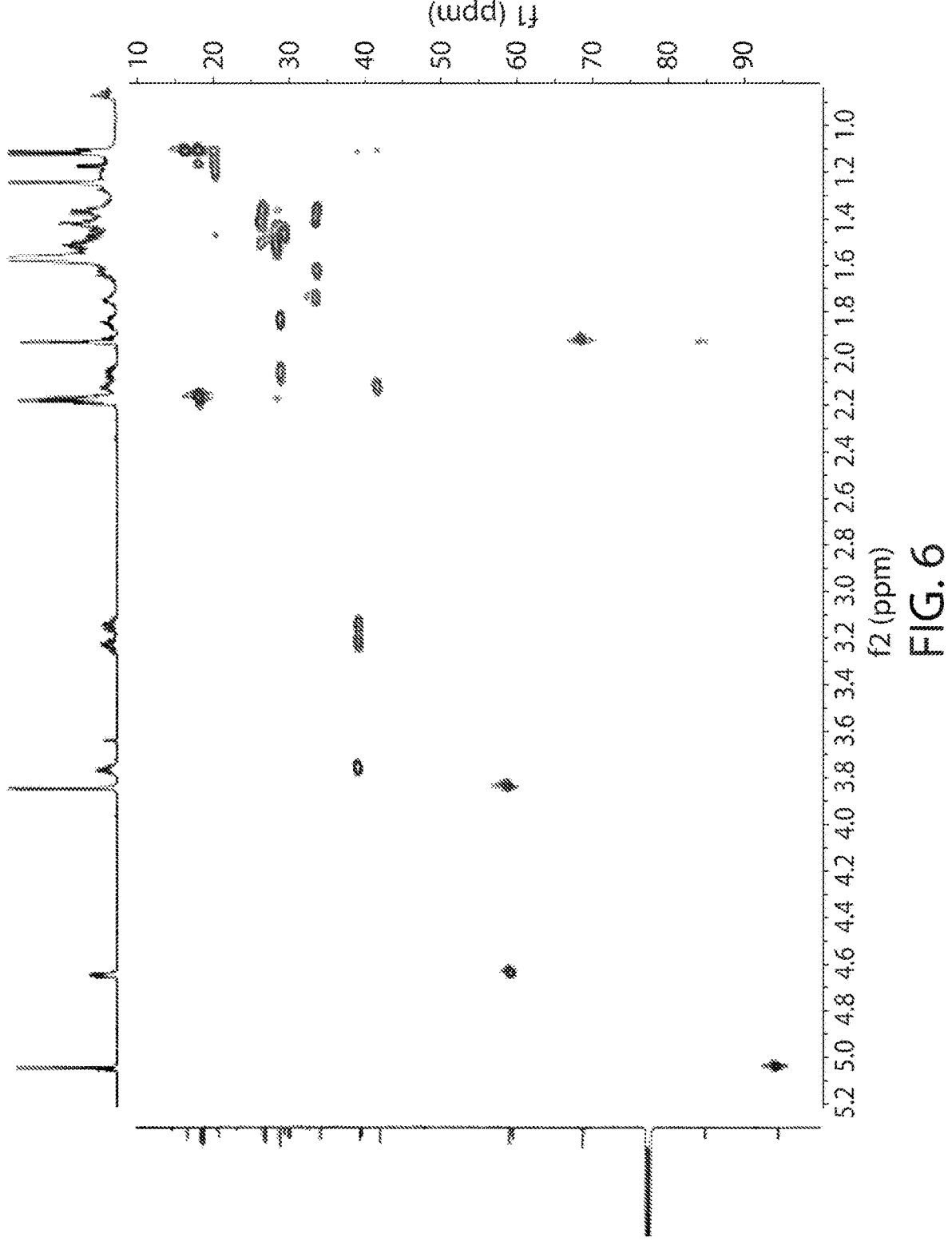
FIG. 6. depicts the HSQC spectrum of doscadenamide A (1a) in CDCl$_3$ (600 MHz) at 27° C.
Figure 7:
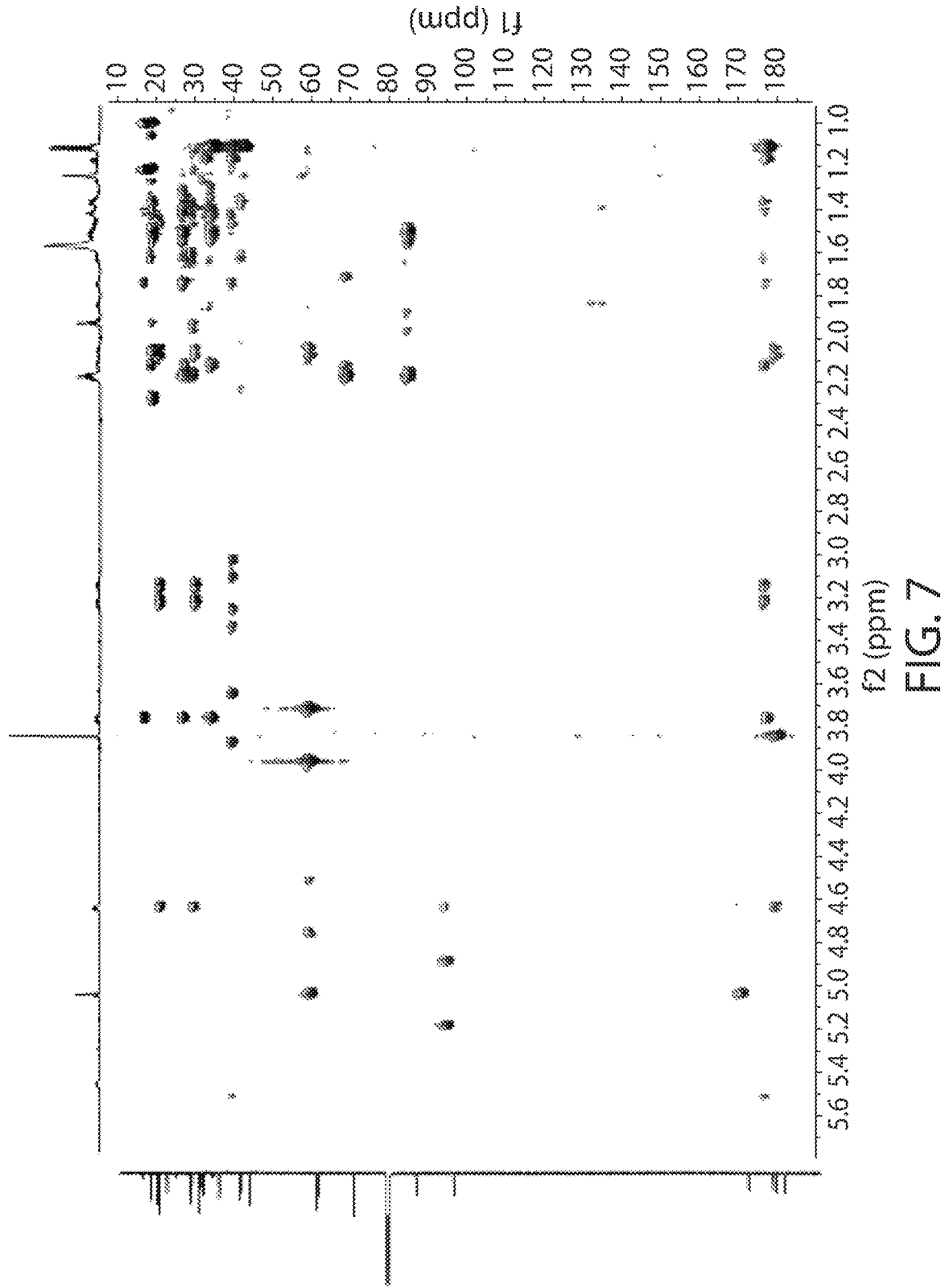
FIG. 7. depicts the HMBC spectrum of doscadenamide A (1a) in CDCl$_3$ (600 MHz) at 27° C.
Figure 8:
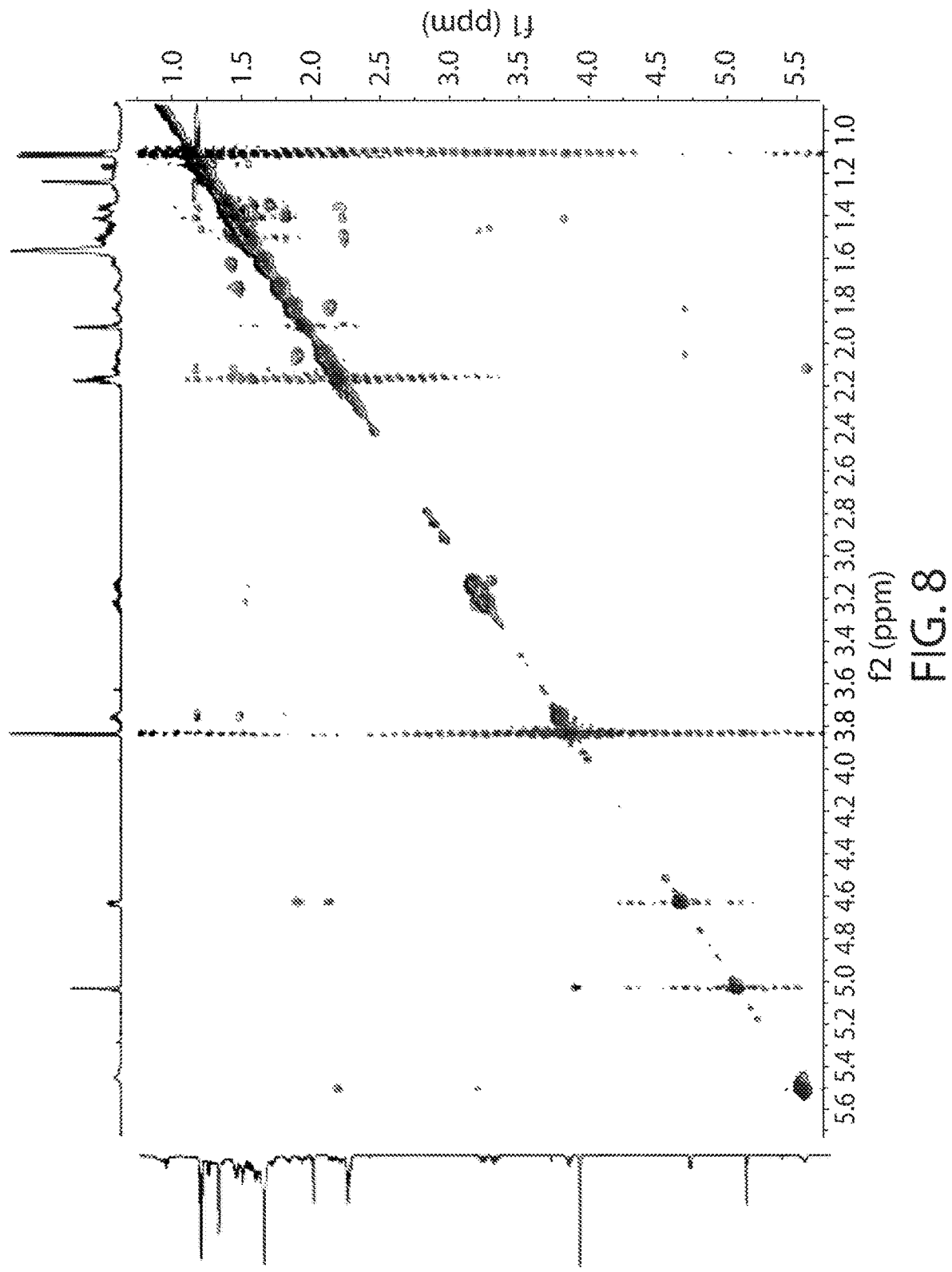
FIG. 8. depicts the NOESY spectrum of doscadenamide A (1a) in CDCl$_3$ (600 MHz) at 27° C.
Figure 10:
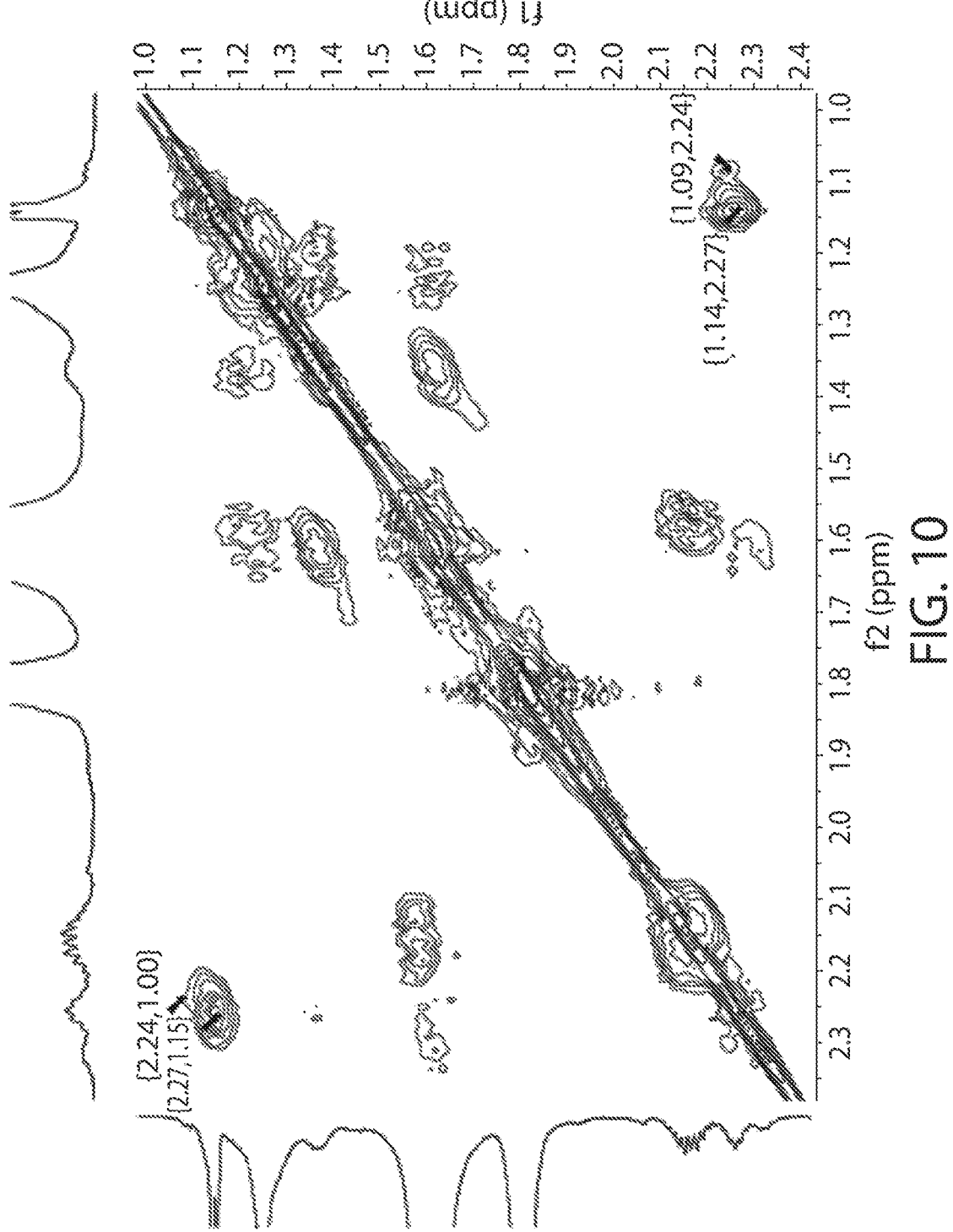
FIG. 10. depicts the COSY spectrum of the (S)-PGME derivative in CDCl$_3$ (600 MHz) at 27° C.
Figure 11:
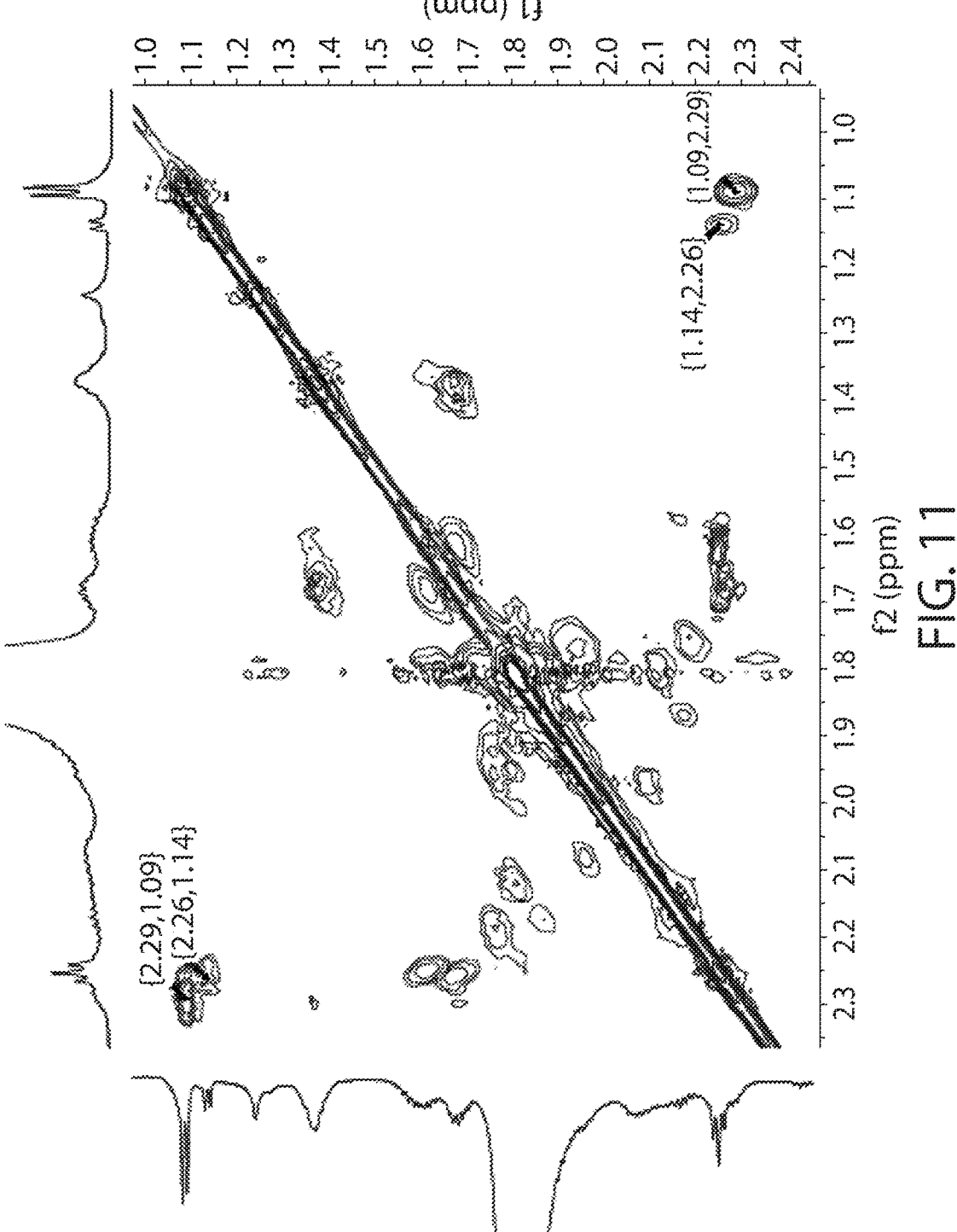
FIG. 11. depicts the COSY spectrum of the (R)-PGME derivative in CDCl$_3$ (600 MHz) at 27° C.

The HRESIMS of 1a in the positive mode exhibited a $[M+H]^+$ peak at m/z 457.3066, which suggested a molecular formula $C_{27}H_{40}N_2O_4$ with 9 degrees of unsaturation. The structure of 1a was elucidated using a combination of 1D and 2D NMR techniques. The ${}^1H$ and ${}^{13}C$ NMR spectra in $CDCl_3$ (FIGS. 2 and 3) indicated the presence of several characteristic signals corresponding to one O-methyl group ($\delta H$ 3.85 ppm, $\delta C$ 58.9 ppm), two alkyne groups ($\delta H$ 1.92-1.94 ppm, $\delta C$ 68.5, 68.5, 84.6, 84.7 ppm), one α-proton ($\delta H$ 4.64-4.66 ppm, $\delta C$ 59.2 ppm), two α-methyl groups ($\delta H$ 1.12-1.14 ppm, $\delta C$ 16.3-18.1 ppm) and several methylene groups ($\delta H$ 1.30-1.90, 2.06-2.18 ppm, $\delta C$ 18.4-39.4 ppm). Examination of the 2D NMR spectra (COSY, TOCSY, HSQC, HMBC and NOESY, FIGS. 4-8, and Table 1) in $CDCl_3$ revealed the structural skeleton of 1a.

TABLE 1

${}^1H$ and ${}^{13}C$ NMR spectral data of doscadenamide A (1a) at 600 MHz and 150 MHz in $CDCl_3$ at 27° C. ($\delta$ in ppm, J in Hz).

| Unit | C/H No. | δH (J) | δC | COSY | HMBC[a] |
|---|---|---|---|---|---|
| pyLys-OMe | 1 | | 170.0 | | |
| | 2 | 5.05, s | 94.2 | | 1, 9 |
| | 3 | | 179.2 | | |
| | 4 | 4.65, dd (5.4, 3.0) | 59.2 | 5 | 2, 3, 5, 6 |
| | 5a | 2.07, ddt (13.8, 11.4, 5.4) | 29.0 | 4, 5b, 6 | 3, 6, 7, 9 |
| | 5b | 1.85, dddd (13.8, 11.4, 5.4, 3.0) | | 4, 5a, 6 | 3, 6, 7, 9 |
| | 6a | 1.19, m | 20.4 | 5, 6b, 7 | 8, 10 |
| | 6b | 1.15, m | | 5, 6a, 7 | 8, 10 |
| | 7 | 1.47, m | 29.6 | 6, 8 | 5, 6, 8 |
| | 8a | 3.24, m | 39.4 | NH, 7 | |
| | 8b | 3.15, m | | NH, 7 | 5, 6, 10 |
| | 9 | 3.85, s | 58.9 | | 3 |
| | NH | 5.47, br s | | 8 | 8, 10 |
| Moya1 | 10 | | 177.0 | | |
| | 11 | 2.13, m | 41.8 | 12, 18 | 10, 12, 18 |
| | 12a | 1.63, m | 33.9 | 12b, 11 | 10, 11, 14, 18 |
| | 12b | 1.38, m | | 12a, 11 | 10, 11, 14, 18 |
| | 13a | 1.43, m | 28.5 | 12, 13b, 14 | 12, 14 |
| | 13b | 1.40, m | | 12, 13a, 14 | 12, 14 |
| | 14a | 1.51, m | 28.5 | 13, 14b, 15 | 12, 15, 17 |
| | 14b | 1.37, m | | 13, 14a, 15 | 12, 15, 17 |
| | 15 | 2.16, m | 18.4 | 14, 17 | 14, 16, 17 |
| | 16 | | 84.6 | | |
| | 17 | 1.93, t (2.6) | 68.5 | 15 | 14 |
| | 18 | 1.13, d (6.6) | 18.1 | 11 | 10, 11 |
| Moya2 | 19 | | 176.4 | | |
| | 20 | 3.77, sextet (6.6) | 39.1 | 21, 27 | 19, 21, 27 |
| | 21a | 1.75, m | 33.7 | 20, 21b, 22 | 20, 22, 27 |
| | 21b | 1.42, m | | 20, 21a, 22 | 20, 22, 27 |
| | 22a | 1.51, m | 26.7 | 21, 22b, 23 | 21, 23, 24, 25 |
| | 22b | 1.37, m | | 21, 22a, 23 | 21, 23, 24, 25 |
| | 23a | 1.51 | 26.4 | 22, 23b, 24 | 22, 24, 25 |
| | 23b | 1.49 | | 22, 23a, 24 | 22, 24, 25 |
| | 24 | 2.17, m | 18.5 | 23, 26 | 22, 23, 25, 26 |
| | 25 | | 84.7 | | |
| | 26 | 1.93, t (2.6) | 68.5 | 24 | 24 |
| | 27 | 1.12, d (6.6) | 16.3 | 20 | 19, 20, 21 |

[a]HMBC correlations are from proton stated to the indicated carbons.

To establish the absolute configuration, Doscadenamide A 1a (2 mg) was dissolved in 3 mL of $CH_2Cl_2$ and ozone was bubbled through the solution for 30 min at 25° C. The solvent was then evaporated and the residue was suspended in $H_2O_2$—HCOOH (1:2) and heated for 20 min at 70° C. (Scheme 1).

Scheme 1.
Determination of the absolute configuration of doscadenamide A (1a)
through ozonolysis followed by acid hydrolysis.

Doscadenamide A (1a)

Subsequently, the resulting mixture was concentrated to dryness and subjected to acid hydrolysis with 6N HCl. The hydrolysate was concentrated and partitioned between EtOAc and water. The aqueous layer was then subjected to chiral HPLC analysis (Phenomenex, Chirex 3126 N,S-dioctyl-(D)-penicillamine, 250 mm×4.60 mm, 5 μm; 1 mM $CuSO_4$ in MeCN; 1.0 mL/min; detection by UV at 254 nm). The absolute configuration of the lysine unit was established as L-Lys (6.5 min), while the authentic D-Lys standard eluted at 8.5 min. The EtOAc layer was coupled with R- or S-phenylglycine methyl ester (PGME) (Scheme 2) to afford the S-PGME derivative {HRMS (ESI) m/z calcd for $C_{26}H_{33}NO_3$ [M+H]$^+$ 469.2333, found 469.2331} or R-PGME derivative {HRMS (ESI) m/z calcd for $C_{26}H_{33}NO_3$ [M+H]$^+$ 469.2333, found 469.2332} of the resulting α-chiral carboxylic acid, respectively.

Scheme 2. Synthetic scheme of the R- and S- PGME derivatives of the carboxylic acid obtained from ozonolysis and follow-up acid hydrolysis.

(R)-2-methylheptanedioic acid

PyBOP, HOBt
N-Me-morpholine

-continued (S)-derivative (R)-derivative

Figure 9:
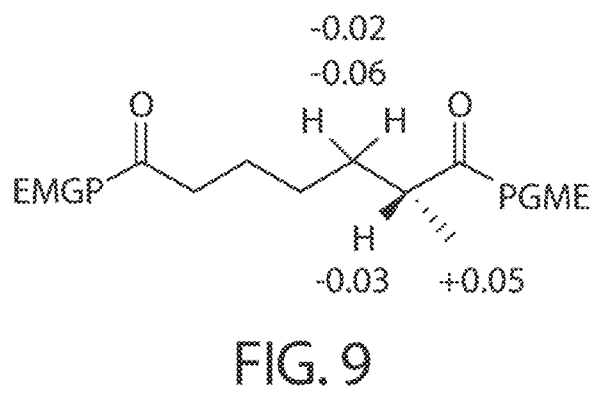

The Δδ values of the methyl protons (+0.05, $\Delta\delta=\delta_S-\delta_R$, FIG. 9), the α-methine proton (−0.03, $\Delta\delta=\delta_S-\delta_R$, FIG. 9) and the adjacent methylene protons (−0.02, −0.06, $\Delta\delta=\delta_S-\delta_R$, FIG. 9) in the resulting carboxylic acid indicated the configuration of the α-methine in the side chain of 1a is highly likely R—. However, during the investigation, a minor diastereomer signal was found in addition to the major NMR signal corresponding to the α-methyl group, which could be observed evidently from the COSY spectra of the two PGME derivatives (Figures S8 and S9). To further validate the configuration of 1a and provide sufficient material for thorough biological investigation, the total synthesis of 1a was accomplished.

Total Synthesis of Doscadenamide A

As depicted in Scheme 3, the retrosynthetic analysis of 1a relied on the disconnection at the two amide linkage between the pyrrolinone ring and two side chain carboxylic acids, which in the case of 1a are the same as (R)-2-methyloct-7-ynoic acid (Moya, 2a). The pyrrolinone ring can be obtained via the reaction between the double protected amino acid Fmoc-L-Lys (Boc)-OH (5) and Meldrum's acid (6).

Scheme 3. Retrosynthetic analysis of doscadenamide A (1a).

Doscadenamide A (1a)

(R)-2-methyloct-7-ynoic acid
(Moya, 2a)

+

3

Fmoc-L-Lys (Boc)—OH (5)

Meldrum's acid (6)

BocHN

4

As for the synthesis of 2a, the target compound can be achieved in 14 steps using a method reported in 2005 [Chen, H.; Feng, Y.; Xu, Z.; Ye, T., *Tetrahedron* 2005, 61 (47), 11132-11140]. To improve the efficiency and introduce more flexibility into the production of diverse carboxylic acids with α-substituted alkyl groups, an optimized synthetic method was developed (Scheme 4), where 2a can be obtained in 4 steps with 45% overall yield. The commercially available oct-7-ynoic acid (2c) was activated using pivaloyl chloride followed by addition of the lithium salt of the oxazolidinone chiral auxiliary at −78° C. The resulting 7a was methylated under conventional conditions to yield 8a as single diastereomer [Evans, D.; Ennis, M.; Mathre, D., *J. Am. Chem. Soc.* 1982, 104 (6), 1737-1739]. The target compound 2a was obtained following alkaline hydrolysis by lithium hydroperoxide [Evans, D.; Britton, T.; Ellman, J., *Tetrahedron Lett.* 1987, 28 (49), 6141-6144].

Scheme 4. Optimized synthesis of Moya (2a).

2c

1) PivCl, TEA THF

2)

LiN

Ph

76%

-continued

17a

MeI, NaHMDS
THF
53%

18a

LiOH, H₂O₂
THF—H₂O
94%

Moya (2a)

The total synthesis of 1a was accomplished using the synthetic carboxylic acid 2a (Scheme 5), including generation of the pyrrolinone core and two coupling processes to assemble the structure. The pyrrolidine-2,4-dione 9a was prepared through condensation of 5 with 6 in the presence of EDCI and DMAP, followed by thermolysis [Hosseini, M.; Kringelum, H.; Murray, A.; Tonder, J., *Org. Lett.* 2006, 8 (10), 2103-2106]. This intermediate was used in the next step without purification. Conversion of 9a into its O-methylated derivative 4 was achieved by treatment with trimethylsilyldiazomethane.

Subsequently, the N-Fmoc protecting group in 4 was removed using piperidine to yield the secondary amide of tetramic acid 3. The first coupling was accomplished by condensation of the anion derived from deprotonation of 3 and the active ester 10a derived from activation of 2a by pentafluorophenol to yield 11a [Jin, Y.; Liu, Y.; Wang, Z.; Kwong, S.; Xu, Z.; Ye, T., *Org. Lett.* 2010, 12 (5), 1100-1103]. After removal of the Boc-protecting group with TFA, the intermediate 12a was condensed with 2a using typical coupling conditions to afford the target compound 1a in 6 steps with 30% overall yield from 3.

Scheme 5. Total synthesis of doscadenamide A (1a).

Doscadenamide A (1a)

Figure 12:
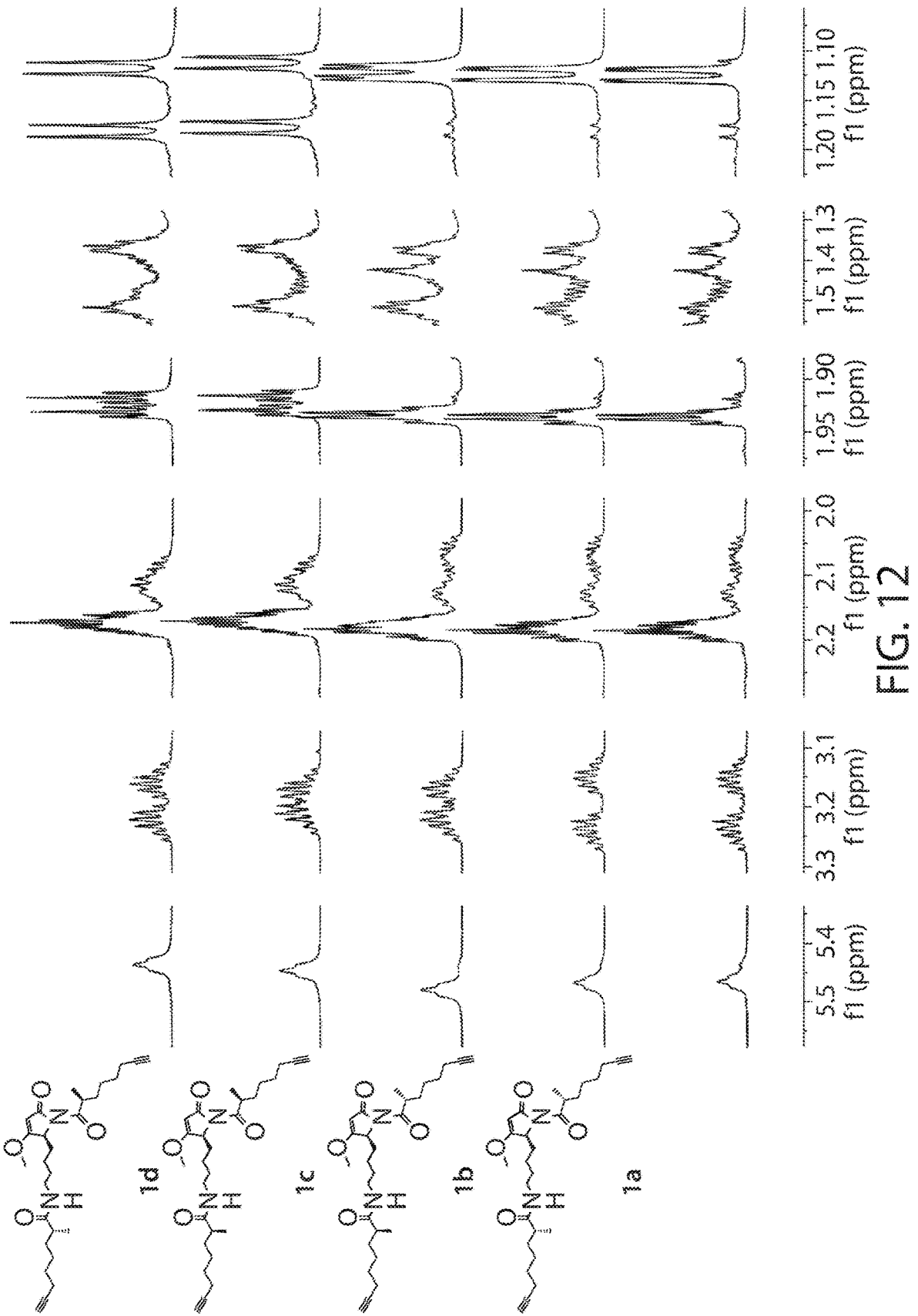
FIG. 12. depicts the regional $^1$H NMR spectra comparison of the isolated natural product doscadenamide A and synthetic diastereomers 1a, 1b, 1c and 1d (bottom to top, maroon, olive, green, navy and purple, respectively) in CDCl$_3$ (600 MHz) at 27° C., with structures of the synthetic diastereomers 1a, 1b, 1c and 1d shown on the left.
Figure 13:
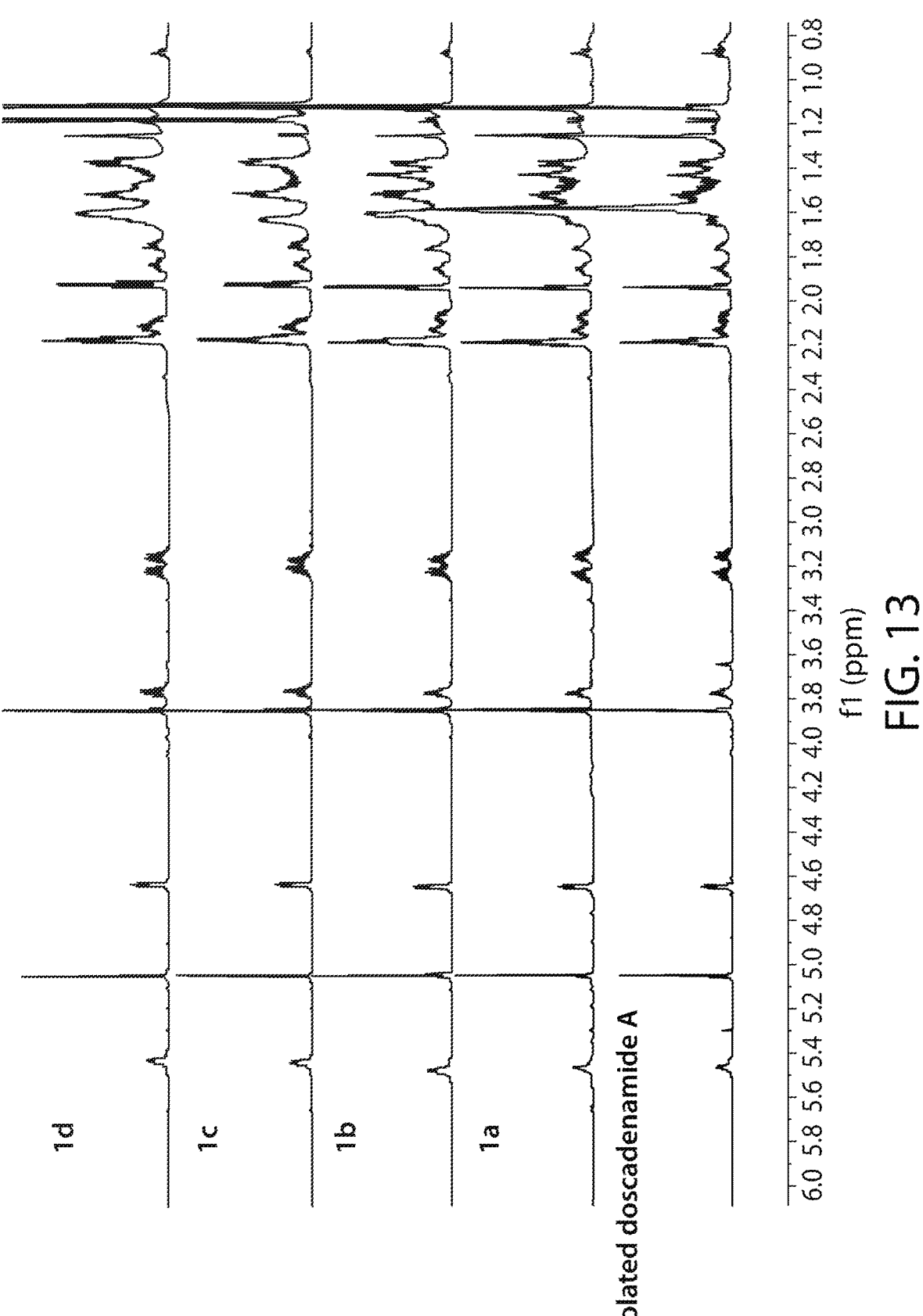
FIG. 13. depicts the $^1$H NMR spectra comparison of natural product doscadenamide A (1a, maroon) with the four synthetic diastereomers 1a (olive), 1b (green), 1c (navy) and 1d (purple) in CDCl$_3$ (600 MHz) at 27° C.
Figure 14:
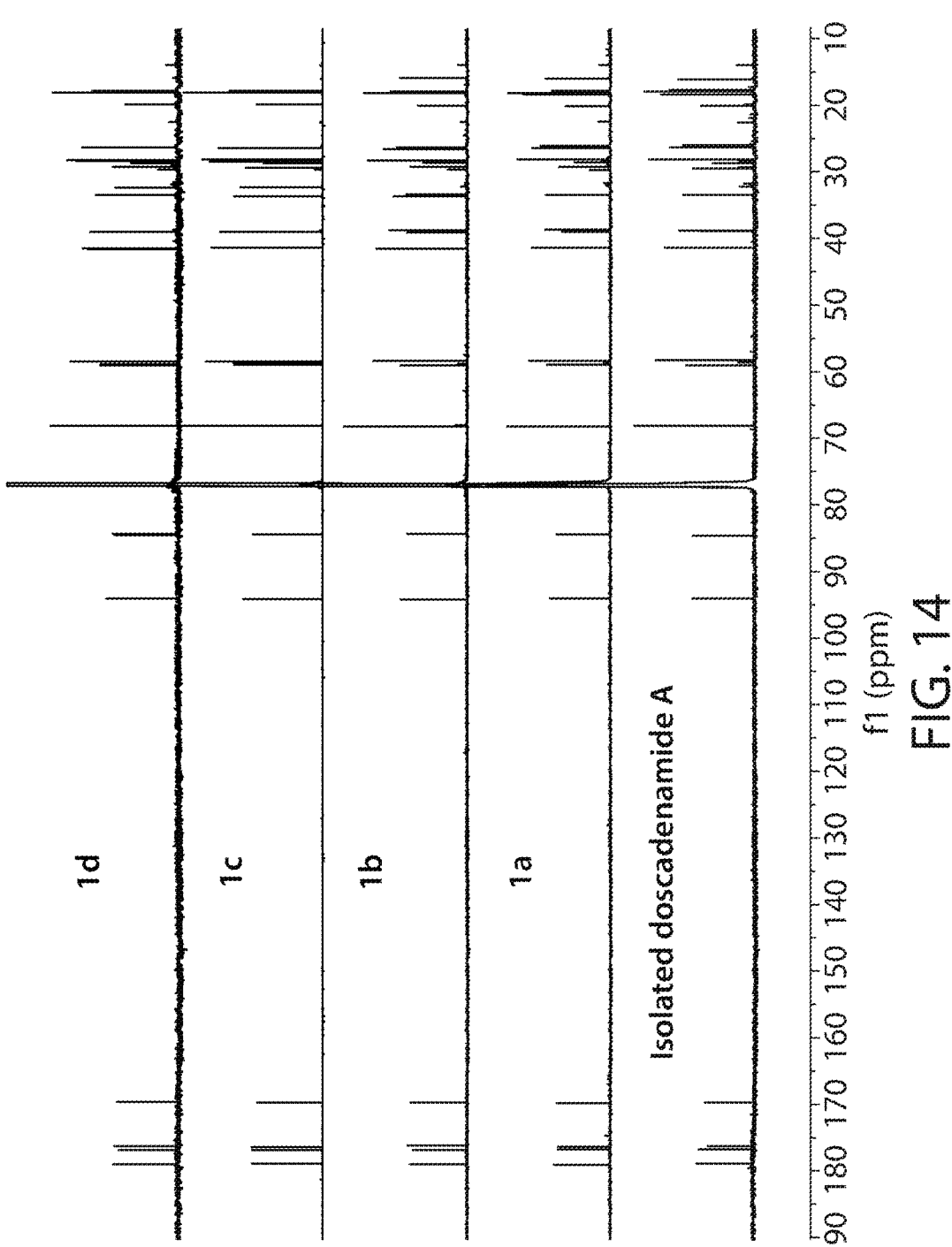
FIG. 14. depicts the $^{13}$C NMR spectra comparison of natural product doscadenamide A (1a, maroon) with the four synthetic diastereomers 1a (olive), 1b (green), 1c (navy) and 1d (purple) in CDCl$_3$ (150 MHz) at 27° C.

To further validate the configuration of the stereocenters in the side chain, the other three diastereomers (1b, 1c and 1d, FIG. 12) of 1a were also synthesized using the described synthetic method. From comparison of the NMR spectra of all the four diastereomers with those of the isolated natural product doscadenamide A (FIGS. 9, 13 and 14), the four diastereomers displayed different $^1$H NMR signals in δ 5.42-5.55 ppm, δ 3.11-3.28 ppm, δ 2.04-2.21 ppm, δ 1.90-1.95 ppm, δ 1.32-1.56 ppm and δ 1.09-1.22 ppm. Only the $^1$H and $^{13}$C NMR spectra of the synthetic 1a matched those of the natural product. Meanwhile, 1a and 1b exhibited virtually the same $^{13}$C NMR spectrum as well as the natural product, while 1c and 1d displayed different $^{13}$C NMR spectra from the isolated doscadenamide A. In addition, the optical rotation values of 1a {$[\alpha]^{20}_D$ 54.3 (c 0.07, MeOH)}, 1b {$[\alpha]^{20}_D$ 62.1 (c 0.07, MeOH)}, 1c {$[\alpha]^{20}_D$ 95.0 (c 0.07, MeOH)} and 1d {$[\alpha]^{20}_D$ 60.0 (c 0.07, MeOH)} further confirmed that the absolute configurations of synthetic diastereomers are consistent with the isolated doscadenamide A. Therefore, the proposed configuration of doscadenamide A was confirmed.

Preparation of Compounds 7a and 7b

2c

To a solution of 7-octynoic acid (2c) (492.6 mg, 3.51 mmol) and trimethylamine (TEA) (0.64 mL, 4.57 mmol) in THF (20 mL) at −20° C. was added neat pivaloyl chloride (0.48 mL, 3.87 mmol) dropwise over 20 min. The resulting mixture was stirred at −20° C. for 30 min and 0° C. for another 30 min, then it was cooled to −78° C. In another reaction flask, n-butyllithium (n-BuLi) (1.6 M in n-hexane) (2.2 ml, 3.51 mmol) was added dropwise to a solution of (R)-oxazolidione (622.6 mg, 3.51 mmol) in tetrahydrofuran at −78° C. The mixture was stirred at this temperature for 20 min and then transferred to the above solution of 2c in THF at −78° C. by cannula. The resulting mixture was stirred at this temperature for 30 min, then it was allowed to warm to room temperature and stirred for additional 1.5 h. The reaction was quenched with saturate NH$_4$Cl solution, followed by extraction with EtOAc (50 mL×3). The organic layer was then washed with 5% NaHCO$_3$ aqueous solution, dried over anhydrous MgSO$_4$ and concentrated in vacuo. The residue was purified by silica gel chromatography column (eluted by 15% ethyl acetate in hexane) to afford 7a (918.0 mg, 87%) as white solid. Intermediate 7b was obtained following the same synthetic procedures using auxiliary (S)-oxazolidione to construct the desired configuration.

(R)-4-benzyl-3-(oct-7-ynoyl)oxazolidin-2-one (7a): $[\alpha]^{20}_D$ −96.0 (c 0.1, MeOH); $^1$H NMR (500 MHz, CDCl3) δ ppm: 7.29 (t, J=7.5 Hz, 2H), 7.23 (t, J=7.5 Hz, 1H), 7.17 (d, J=7.5 Hz, 2H), 4.65-4.60 (m, 1H), 4.16-4.10 (m, 2H), 3.24 (dd, J=13.5, 3.0 Hz, 1H), 2.98-2.82 (m, 2H), 2.74 (dd, J=13.5, 9.5 Hz, 1H), 2.17 (td, J=7.0, 2.5 Hz, 2H), 1.92 (t, J=2.5 Hz, 1H), 1.71-1.64 (m, 2H), 1.55 (p, J=7.0, 2H), 1.47 (p, J=7.5, 2H); $^{13}$C NMR (125 MHz, CDCl3) δ ppm: 173.0, 153.3, 135.3, 129.3, 128.8, 127.2, 84.3, 68.4, 66.1, 55.0, 37.8, 35.3, 28.1, 28.1, 23.6, 18.2; HRMS (ESI) m/z calcd for C$_{18}$H$_{22}$NO$_3$ [M+H]$^+$ 300.1594, found 300.1590.

(S)-4-benzyl-3-(oct-7-ynoyl)oxazolidin-2-one (7b): (802.0 mg, 95%); $[\alpha]^{20}_D$ 91.0 (c 0.1, MeOH); $^1$H NMR (600 MHz, CDCl$_3$) δ ppm: 7.33 (t, J=7.2 Hz, 2H), 7.27 (t, J=7.2 Hz, 1H), 7.20 (d, J=6.6 Hz, 2H), 4.67 (ddt, J=8.7, 8.7, 3.0 Hz, 1H), 4.21-4.15 (m, 2H), 3.29 (dd, J=13.2, 3.6 Hz, 1H), 3.01-2.88 (m, 2H), 2.77 (dd, J=13.2, 9.6 Hz, 1H), 2.21 (td, J=7.2, 2.4 Hz, 2H), 1.94 (t, J=2.4 Hz, 1H), 1.76-1.68 (m, 2H), 1.63-1.56 (m, 2H), 1.53-1.49 (m, 2H); $^{13}$C NMR (150 MHz, CDCl$_3$) δ ppm: 173.3, 153.6, 135.4, 129.5, 129.1, 127.5, 84.5, 68.5, 66.3, 55.2, 38.0, 35.5, 28.3, 28.3, 23.8, 18.4; HRMS (ESI) m/z calcd for C$_{18}$H$_{22}$NO$_3$ [M+H]$^+$ 300.1594, found 300.1591.

Preparation of Compounds 8a and 8b

-continued

7b

8b

To a solution of sodium bis(trimethylsilyl)amide (NaHMDS) (2.0 M in THF) (1.69 ml, 3.37 mmol) in anhydrous THF (10 ml) at −78° C. was added compound 7a (918.0 mg, 3.07 mmol) in THF (5.0 ml) under argon atmosphere. After stirring at the same temperature for 30 min, neat MeI (0.96 ml, 15.35 mmol) was added dropwise over 10 min to the resulting reaction solution. The reaction was then quenched with saturate NH$_4$Cl (aq) (20 ml) after it was stirred at −78° C. for 20 h. Subsequently, the residue was extracted with ethyl acetate (30 ml×3), dried over anhydrous MgSO$_4$, and concentrated in vacuo. The residue was purified by silica gel chromatography column (eluted by κ% ethyl acetate in hexane) to afford products 8a (493.8 mg, 51%) as white solid. Intermediate 8b was obtained using 7b following the same synthetic procedures.

(R)-4-benzyl-3-((R)-2-methyloct-7-ynoyl)oxazolidin-2-one (8a): [α]$^{20}_D$ −268.5 (c 0.1, MeOH); $^1$H NMR (500 MHz, CDCl$_3$) δ ppm: 7.33 (t, J=7.5 Hz, 2H), 7.27 (t, J=7.5 Hz, 1H), 7.21 (d, J=7.5 Hz, 2H), 4.70-4.65 (m, 1H), 4.22-4.15 (m, 2H), 3.71 (sextet, J=6.5 Hz, 1H), 3.26 (dd, J=13.5, 3.5 Hz, 1H), 2.77 (dd, J=13.5, 10.0 Hz, 1H), 2.20-2.17 (m, 2H), 1.93 (br t, 1H), 1.79-1.71 (m, 1H), 1.56-1.50 (m, 2H), 1.48-1.38 (m, 3H), 1.23 (d, J=6.5 Hz, 3H); $^{13}$C NMR (125 MHz, CDCl$_3$) δ ppm: 177.3, 153.2, 135.4, 129.6, 129.1, 127.5, 84.5, 68.5, 66.2, 55.5, 38.1, 37.8, 32.9, 28.5, 26.5, 18.4, 17.5; HRMS (ESI) m/z calcd for C$_{19}$H$_{24}$NO$_3$ [M+H]$^+$ 314.1751, found 314.1748.

(S)-4-benzyl-3-((R)-2-methyloct-7-ynoyl)oxazolidin-2-one (8b): (378.3 mg, 45%); [α]$^{20}_D$ 18.0 (c 0.1, MeOH); $^1$H NMR (600 MHz, CDCl$_3$) δ ppm: 7.33-7.31 (m, 2H), 7.29-7.26 (m, 1H), 7.22-7.20 (m, 2H), 4.68 (ddt, J=9.6, 7.8, 3.0 MHz, 1H), 4.22-4.16 (m, 2H), 3.71 (h, J=7.2 Hz, 1H), 3.26 (dd, J=13.2, 3.6 Hz, 1H), 2.77 (dd, J=13.2, 9.0 Hz, 1H), 2.19 (td, J=6.6, 1.8 Hz, 2H), 1.93 (t, J=2.4 Hz, 1H), 1.80-1.72 (m, 1H), 1.58-1.50 (m, 2H), 1.49-1.39 (m, 3H), 1.23 (d, J=6.6 Hz, 3H); $^{13}$C NMR (150 MHz, CDCl$_3$) δ ppm: 177.2, 153.2, 135.4, 129.6, 129.1, 127.5, 84.5, 68.5, 66.2, 55.5, 38.0, 37.8, 32.9, 28.5, 26.5, 18.4, 17.5; HRMS (ESI) m/z calcd for C$_{19}$H$_{24}$NO$_3$ [M+H]$^+$ 314.1751, found 314.1749.

Preparation of Compounds 2a and 2b

8a

Moya (2a)

8b

2b

Hydrogen peroxide (30% in H$_2$O$_2$) (0.55 ml, 4.82 mmol) was added to the solution of 8a (378.8 mg, 1.20 mmol) in the mixture of THF-H$_2$O (8.0 ml-4.0 ml) at 0° C. After stirring at 0° C. for 10 min, LiOH·H$_2$O (101.1 mg, 2.41 mmol) was added to the above reaction solution. Then the resulting reaction mixture was stirred at 0° C. for 2 h and additional 1 h at room temperature before Na$_2$SO$_3$ (760 mg) was added. The quenched reaction mixture was diluted with water (20 ml) and EtOAc (20 ml). The organic ethyl acetate phase was separated and the aqueous phase was acidified with 1M HCl (aq) to pH 2 and extracted EtOAc (20 ml×3). The combined EtOAc phase was dried over anhydrous MgSO$_4$, concentrated in vacuo and purified by silica gel column chromatography (eluted by 17% ethyl acetate in hexane) to afford products 2a (175.0 mg, 94%) as clear oil. 2b was obtained from 8b following the same procedure.

(R)-2-methyloct-7-ynoic acid (Moya, 2a): [α]$^{20}_D$ −19.0 (c 0.1, MeOH); $^1$H NMR (500 MHz, CDCl$_3$) δ ppm: 2.47 (sextet, J=6.5 Hz, 1H), 2.19 (td, J=7.0, 2.5 Hz, 2H), 1.94 (br t, J=2.5 Hz, 1H), 1.73-1.67 (m, 1H), 1.54 (p, J=7.0, 2H), 1.49-1.41 (m, 3H), 1.19 (d, J=7.0 Hz, 3H); $^{13}$C NMR (125 MHz, CDCl$_3$) δ ppm: 183.1, 84.4, 68.5, 39.4, 33.0, 28.4, 26.4, 18.4, 17.0; HRMS (ESI) m/z calcd for C$_9$H$_{15}$O$_2$ [M+H]$^+$ 155.1067, found 155.1063.

(S)-2-methyloct-7-ynoic acid (2b): (169.5 mg, 93%); [α]$^{20}_D$ 14.0 (c 0.1, MeOH); $^1$H (600 MHz, CDCl$_3$) δ ppm: 2.50-2.45 (h, 1H), 2.20 (td, J=7.2, 3.0 Hz, 2H), 1.94 (t, J=3.0 Hz, 1H), 1.74-1.68 (m, 1H), 1.57-1.52 (m, 2H), 1.49-1.42 (m, 3H), 1.19 (d, J=7.0 Hz, 3H); $^{13}$C NMR (125 MHz, CDCl$_3$) δ ppm: 182.5, 84.4, 68.5, 39.3, 33.1, 28.4, 26.4, 18.4, 17.0; HRMS (ESI) m/z calcd for C$_9$H$_{15}$O$_2$ [M+H]$^+$ 155.1067, found 155.1064.

Preparation of Compounds 20a and 20b

20b

To the solution of N-Fmoc-L-Lys (Boc)-OH (5, 1.0 g, 2.13 mmol) and Meldrum's acid (6, 338.4 mg, 2.35 mmol) in anhydrous $CH_2Cl_2$ (20 ml) at 0° C. was added 4-dimethylaminopyridine (DMAP) (391 mg, 3.20 mmol) and EDCI·HCl (530 mg, 2.77 mmol). After being stirred overnight at room temperature, the reaction solution was diluted with EtOAc (60 ml), washed by 5% citric acid (aq) (20 ml×4) and brine (20 ml×2), and the combined organic phase was then dried over anhydrous $MgSO_4$. The filtered EtOAc phase was refluxed under heating for 30 min, then cooled down to room temperature and evaporated to give crude intermediate 9a, which was used in the next step without purification.

To a solution of the above crude 9a in the mixture of diethyl ether (160 ml) and methanol (40 ml) was added trimethylsilyldiazomethane ($TMSCHN_2$) (4.4 ml, 8.79 mmol). The resulting mixture was stirred overnight at room temperature, then concentrated under reduced pressure. The residue was dissolved in EtOAc (150 ml), washed with 5% citric acid (aq.) (30 ml×3), saturate $NaHCO_3$ (aq) (30 ml×2 and brine (30 ml), dried over anhydrous $MgSO_4$, and evaporated in vacuo. Product 20a was obtained (558.0 mg, 50%) and 20b (18%) were obtained as white solid after purification by silica gel column chromatography (eluted by 50-70% ethyl acetate in hexane).

(9H-fluoren-9-yl)methyl (S)-2-(4-((tert-butoxycarbonyl)amino)butyl)-3-methoxy-5-oxo-2,5-dihydro-1H-pyrrole-1-carboxylate (20a): $[\alpha]^{20}_D$ 68.5 (c 0.1, MeOH); $^1$H NMR (600 MHz, $CDCl_3$) δ ppm: 7.77-7.74 (m, 4H), 7.40 (t, J=7.2 Hz, 2H), 7.33 (tt, J=7.1, 1.2 Hz, 2H), 5.09 (s, 1H), 4.58 (m, 2H), 4.47 (br s, 1H), 4.36 (dd, J=5.4, 3.0 Hz, 1H), 4.32 (t, J=6.6 Hz, 1H), 3.83 (s, 3H), 3.07-2.98 (m, 2H), 1.85-1.79 (m, 1H), 1.73-1.67 (m, 1H), 1.43 (s, 9H), 1.36-1.31 (m, 2H), 1.19-1.11 (m, 1H), 1.02-0.96 (m, 1H); $^{13}$C NMR (150 MHz, $CDCl_3$) δ ppm: 178.1, 168.9, 155.1, 151.1, 143.8, 143.7, 141.5, 141.4, 128.0, 127.9, 127.4, 125.4, 125.3, 120.1, 120.0, 94.5, 79.3, 68.1, 59.9, 58.8, 46.9, 40.5, 29.8, 28.7, 28.6, 19.6; HRMS (ESI) m/z calcd for $C_{29}H_{35}N_2O_6$ [M+H]$^+$ 507.2490, found 507.2492.

Compound 20c,

20c was prepared from 3',

3' using the same procedure as used to prepare compounds 20a and 20b.

Preparation of Compound 3

4

3

Piperidine (2.0 ml) was added to the solution of 4 (366.3 mg, 0.723 mmol) in MeCN (10 mL) at room temperature. After stirred at the same temperature for 15 min, the reaction mixture was concentrated and co-evaporated with toluene for 3 times. The residue was purified by silica gel column chromatography (eluted by EtOAc/hexane 1:1, then by 3-3.5% MeOH in $CH_2Cl_2$) to afford 3 (180.0 mg, 88%) as white solid.

tert-butyl (S)-(4-(3-methoxy-5-oxo-2,5-dihydro-1H-pyrrol-2-yl)butyl)carbamate (3): $[\alpha]^{20}_D$ 10.0 (c 0.1, MeOH); $^1$H NMR (500 MHz, $CDCl_3$) δ ppm: 6.30 (br s, 1H), 5.01 (s, 1H), 4.74 (t, J=6.0 Hz, 1H), 4.04 (dd, J=7.5, 4.0 Hz, 1H), 3.78 (s, 3H), 3.17-3.05 (m, 2H), 1.84-1.77 (m, 1H), 1.56-1.48 (m, 3H), 1.47-1.41 (m, 10H), 1.39-1.30 (m, 1H); $^{13}$C NMR (125 MHz, $CDCl_3$) δ ppm: 178.5, 175.1, 156.2, 93.6, 78.9, 58.3, 57.5, 40.2, 31.4, 29.4, 28.5, 22.2; HRMS (ESI) m/z calcd for $C_{14}H_{25}N_2O_4$ [M+H]$^+$ 285.1809, found 285.1808.

21b and

-continued

21c were prepared using the same procedure used to prepare compound 3.

Preparation of Compounds 10a and 10b

2a

10a

2b

10b

To the solution of 2a (29.1 mg, 0.1 mmol) in anhydrous CH$_2$Cl$_2$ (3.0 ml) at 0° C. was added pentafluorophenol (40.1 mg, 0.22 mmol) in anhydrous CH$_2$Cl$_2$ (0.5 ml), DMAP (2.4 mg, 0.02 mmol) and DCC (49.5 mg, 0.24 mmol). The resulting reaction mixture was stirred at room temperature overnight and concentrated under reduced pressure. The residue was stirred in cooled EtOAc (3.0 ml), and the suspending solid was filtered off. The filtrate was evaporated in vacuo and purified with silica gel column chromatography (eluted by 7% EtOAc in hexane) to yield 10a (60.0 mg, 95%) as white solid. 10b was synthesized from 2b following the same procedure.

Perfluorophenyl (R)-2-methyloct-7-ynoate (10a): $[\alpha]^{20}_D$ −27.5 (c 0.1, MeOH); $^1$H NMR (600 MHz, CDCl$_3$) δ ppm: 2.82 (h, J=6.6 Hz, 1H), 2.19 (td, J=6.6, 3.0 Hz, 2H), 1.94 (br t, J=3.0 Hz, 1H), 1.87-1.81 (m, 1H), 1.65-1.51 (m, 5H), 1.34 (d, J=7.2 Hz, 3H); $^{13}$C NMR (150 MHz, CDCl$_3$) δ ppm: 172.7, 142.1 (m), 140.5 (m), 138.8 (m), 137.2 (m), 125.4 (m), 84.2, 68.7, 39.4, 33.1, 28.3, 26.2, 18.4, 17.1; HRMS (ESI) m/z calcd for C$_{15}$H$_{14}$O$_2$F$_5$ [M+H]$^+$ 321.0908, found 321.0912.

Perfluorophenyl (S)-2-methyloct-7-ynoate (10b): (84%); $[\alpha]^{20}_D$ 14.0 (c 0.1, MeOH); $^1$H NMR (600 MHz, CDCl$_3$) δ ppm: 2.82 (h, J=6.6 Hz, 1H), 2.23 (td, J=6.6, 2.4 Hz, 2H), 1.96 (t, J=2.4 Hz, 1H), 1.87-1.81 (m, 1H), 1.65-1.50 (m, 5H), 1.35 (d, J=7.2 Hz, 3H); $^{13}$C NMR (150 MHz, CDCl$_3$) δ ppm: 172.7, 142.1 (m), 140.5 (m), 138.8 (m), 137.2 (m), 125.4 (m), 84.2, 68.7, 39.4, 33.1, 28.3, 26.2, 18.4, 17.1; HRMS (ESI) m/z calcd for C$_{15}$H$_{14}$O$_2$F$_5$ [M+H]$^+$ 321.0908, found 321.0915.

22c

22d and

22e were prepared using the same procedure used to prepare compounds 10a and 10b.

Preparation of Compounds 11a and 11b

3

+

10a

11a

3

+

10b

-continued

11b

88

23c and

23d were prepared using the same procedure used to prepare compounds 11a and 11b.

Preparation of Compounds 1a-1d

To a solution of 3 (16.9 mg, 0.06 mmol) in anhydrous THF (1.0 ml) at −55° C. was added n-BuLi (1.6 M in n-hexane) (0.056 ml, 0.089 mmol), the solution was stirred the same temperature for 30 min. Subsequently, the activated carboxylic acid 10a (28.5 mg, 0.089 mmol) in anhydrous THF (0.5 ml) was added dropwise at −55° C. The resulting reaction mixture was stirred at the same temperature for 3 h and then room temperature overnight. The reaction was quenched on the next day with saturate NH₄Cl (aq, 3.0 ml) and then extracted with EtOAc (5 ml×3). The combined organic phase was washed with saturate NaHCO₃ (aq, 5 ml×2) and brine (5 ml), dried over anhydrous MgSO₄, and purified by preparative TLC plate of silica gel to yield corresponding product 11a (23.9 mg, 93%) as white solid. 11b was obtained following the same procedure using 10b.

tert-butyl (4-((S)-3-methoxy-1-((R)-2-methyloct-7-ynoyl)-5-oxo-2,5-dihydro-1H-pyrrol-2-yl)butyl)carbamate (11a): $[\alpha]^{20}_D$ 65.0 (c 0.1, MeOH); $^1$H NMR (600 MHz, CDCl₃) δ ppm: 5.04 (s, 1H), 4.65 (dd, J=5.4, 3.0 Hz, 1H), 4.51 (br s, 1H), 3.84 (s, 3H), 3.77 (sextet, J=6.6 Hz, 1H), 3.09-3.01 (m, 2H), 2.18 (td, J=6.6, 2.4 Hz, 2H), 2.08 (ddt, J=13.8, 11.4, 5.4 Hz, 1H), 1.93 (t, J=3.0 Hz, 1H), 1.83 (dddd, J=13.8, 11.4, 5.4, 3.0 Hz, 1H), 1.78-1.71 (m, 1H), 1.57-1.49 (m, 2H), 1.48-1.39 (m, 14H), 1.21-1.14 (m, 1H), 1.12-1.06 (m, 4H); $^{13}$C NMR (150 MHz, CDCl₃) δ ppm: 179.1, 177.0, 170.0, 156.1, 94.3, 84.6, 79.3, 68.5, 59.2, 58.8, 40.5, 39.1, 33.7, 30.0, 28.8, 28.6, 28.5, 26.4, 20.0, 18.5, 18.3; HRMS (ESI) m/z calcd for C₂₃H₃₇N₂O₅ [M+H]⁺ 421.2697, found 421.2692.

tert-butyl (4-((S)-3-methoxy-1-((S)-2-methyloct-7-ynoyl)-5-oxo-2,5-dihydro-1H-pyrrol-2-yl)butyl)carbamate (11b): (60%); $[\alpha]^{20}_D$ 68.0 (c 0.1, MeOH); $^1$H NMR (600 MHz, CDCl₃) δ ppm: 5.04 (s, 1H), 4.65 (dd, J=5.4, 3.0 Hz, 1H), 4.51 (br s, 1H), 3.84 (s, 3H), 3.77 (sextet, J=6.6 Hz, 1H), 3.07-3.04 (m, 2H), 2.17 (td, J=6.6, 2.4 Hz, 2H), 2.12 (ddt, J=13.8, 11.4, 5.4 Hz, 1H), 1.92 (t, J=3.0 Hz, 1H), 1.82 (dddd, J=13.8, 11.4, 5.4, 3.0 Hz, 1H), 1.78-1.72 (m, 1H), 1.55-1.50 (m, 2H), 1.48-1.35 (m, 14H), 1.20-1.15 (m, 4H), 1.13-1.06 (m, 1H); $^{13}$C NMR (150 MHz, CDCl₃) δ ppm: 179.1, 177.0, 170.0, 156.0, 94.3, 84.7, 79.3, 68.3, 59.2, 58.8, 40.4, 39.3, 32.4, 29.9, 28.7, 28.7, 28.6, 26.6, 19.8, 18.5, 18.2; HRMS (ESI) m/z calcd for C₂₃H₃₇N₂O₅ [M+H]⁺ 421.2697, found 421.2693.

TFA:DCM = 1:2
on ice

11a

2a, EDCl,
HOBt, DIEA
DMF

12a

89
-continued

Doscadenamide A (1a)

11a

TFA:DCM = 1:2
on ice

12a

2b, EDCl,
HOBt, DIEA
DMF

1b

11b

TFA:DCM = 1:2
on ice

90
-continued

12b

2b, EDCl,
HOBt, DIEA
DMF

1c

11b

TFA:DCM = 1:2
on ice

12b

2a, EDCl,
HOBt, DIEA
DMF

1d

To the solution of compound 11a (2.1 mg, 0.005 mmol) in CH$_2$Cl$_2$ (0.6 ml) was added TFA (0.3 ml) at 0° C. and the mixture was stirred the same temperature for 30 min. The reaction was diluted with toluene (1 ml) and evaporated in vacuo (3 times) to produce crude 12a, which was used in next step without purification. To the solution of crude 12a in anhydrous DMF (1.0 ml) was added 2a (0.8 mg, 0.005 mmol), EDCI·HCl (1.4 mg, 0.015 mmol), HOBt·H$_2$O (1.2 mg, 0.008 mmol) and DIEA (3.0 µL). The reaction mixture was stirred at room temperature for 20 h and then was evaporated in vacuo and purified by preparative TLC plate to yield product 1a (1.8 mg, 79%) as white solid. 1b, 1e and 1d were synthesized following the same procedure with corresponding starting materials.

(R)-N-(4-((S)-3-methoxy-1-((R)-2-methyloct-7-ynoyl)-5-oxo-2,5-dihydro-1H-pyrrol-2-yl)butyl)-2-methyloct-7-ynamide (Doscadenamide A, 1a): $[\alpha]^{20}_D$ 54.3 (c 0.07, MeOH); $^1$H NMR (600 MHz, CDCl$_3$) δ ppm: 5.47 (br t, J=6.0 Hz, 1H), 5.05 (s, 1H), 4.65 (dd, J=5.4, 3.0 Hz, 1H), 3.85 (s, 3H), 3.77 (sextet, J=6.6 Hz, 1H), 3.27-3.21 (m, 1H), 3.17-3.12 (m, 1H), 2.20-2.17 (m, 4H), 2.14-2.11 (m, 1H), 2.07 (ddt, J=13.8, 11.4, 5.4 Hz, 1H), 1.94 (t, J=2.4 Hz, 1H), 1.93 (t, J=2.4 Hz, 1H), 1.85 (dddd, J=13.8, 11.4, 5.4, 3.0 Hz, 1H), 1.79-1.71 (m, 1H), 1.65-1.62 (m, 1H), 1.54-1.46 (m, δH), 1.45-1.40 (m, 3H), 1.39-1.35 (m, 3H), 1.21-1.17 (m, 1H), 1.16-1.15 (m, 1H), 1.13-1.11 (m, δH); $^{13}$C NMR (150 MHz, CDCl$_3$) δ ppm: 179.2, 177.0, 176.4, 170.0, 94.2, 84.7, 84.6, 68.5, 68.5, 59.2, 58.9, 41.8, 39.4, 39.1, 33.9, 33.7, 29.9, 29.6, 29.0, 28.5, 28.5, 26.7, 26.4, 20.4, 18.5, 18.4, 18.1, 16.3; HRMS (ESI) m/z calcd for C$_{27}$H$_{41}$N$_2$O$_4$ [M+H]$^+$ 457.3061, found 457.3058.

(S)-N-(4-((S)-3-methoxy-1-((R)-2-methyloct-7-ynoyl)-5-oxo-2,5-dihydro-1H-pyrrol-2-yl)butyl)-2-methyloct-7-ynamide (1b): (67%); $[\alpha]^{20}_D$ 62.1 (c 0.07, MeOH); $^1$H NMR (600 MHz, CDCl$_3$) δ ppm: 5.48 (br t, J=6.0 Hz, 1H), 5.05 (s, 1H), 4.65 (dd, J=6.0, 3.6 Hz, 1H), 3.85 (s, 3H), 3.77 (sextet, J=6.6 Hz, 1H), 3.26-3.20 (m, 1H), 3.19-3.13 (m, 1H), 2.20-2.16 (m, 4H), 2.15-2.11 (m, 1H), 2.07 (ddt, J=13.8, 11.4, 5.4 Hz, 1H), 1.94 (t, J=2.4 Hz, 1H), 1.93 (t, J=2.4 Hz, 1H), 1.85 (dddd, J=13.8, 11.4, 5.4, 3.0 Hz, 1H), 1.78-1.72 (m, 1H), 1.65-1.63 (m, 1H), 1.54-1.47 (m, δH), 1.45-1.41 (m, 3H), 1.39-1.35 (m, 3H), 1.22-1.18 (m, 1H), 1.18-1.14 (m, 1H), 1.12 (d, J=6.6 Hz, 3H), 1.12 (d, J=7.2 Hz, 3H); $^{13}$C NMR (150 MHz, CDCl$_3$) δ ppm: 179.2, 177.0, 176.4, 170.0, 94.2, 84.7, 84.6, 68.5, 68.5, 59.2, 58.9, 41.7, 39.3, 39.1, 33.9, 33.7, 29.9, 29.6, 29.0, 28.5, 28.5, 26.8, 26.4, 20.4, 18.5, 18.4, 18.1, 16.3; HRMS (ESI) m/z calcd for C$_{27}$H$_{41}$N$_2$O$_4$ [M+H]$^+$ 457.3061, found 457.3057.

(S)-N-(4-((S)-3-methoxy-1-((S)-2-methyloct-7-ynoyl)-5-oxo-2,5-dihydro-1H-pyrrol-2-yl)butyl)-2-methyloct-7-ynamide (1c): (82%); $[\alpha]^{20}_D$ 95.0 (c 0.07, MeOH); $^1$H NMR (600 MHz, CDCl$_3$) δ ppm: 5.45 (br t, J=5.4 Hz, 1H), 5.05 (s, 1H), 4.64 (dd, J=6.0, 3.0 Hz, 1H), 3.85 (s, 3H), 3.76 (sextet, J=7.2 Hz, 1H), 3.24-3.19 (m, 1H), 3.19-3.14 (m, 1H), 2.20-2.16 (m, 4H), 2.14-2.07 (m, 2H), 1.93 (t, J=3.0 Hz, 1H), 1.92 (t, J=3.0 Hz, 1H), 1.83 (dddd, J=13.8, 11.4, 5.4, 3.0 Hz, 1H), 1.77-1.72 (m, 1H), 1.64-1.62 (m, 1H), 1.54-1.46 (m, δH), 1.45-1.33 (m, δH), 1.21-1.17 (m, 4H), 1.15-1.10 (m, 4H); $^{13}$C NMR (150 MHz, CDCl$_3$) δ ppm: 179.2, 177.0, 176.4, 170.0, 94.2, 84.7, 84.6, 68.5, 68.3, 59.2, 58.9, 41.7, 39.3, 39.2, 33.9, 32.5, 29.5, 28.9, 28.7, 28.5, 26.7, 26.6, 20.2, 18.5, 18.4, 18.1, 18.1; HRMS (ESI) m/z calcd for C$_{27}$H$_{41}$N$_2$O$_4$ [M+H]$^+$ 457.3061, found 457.3058.

(R)-N-(4-((S)-3-methoxy-1-((S)-2-methyloct-7-ynoyl)-5-oxo-2,5-dihydro-1H-pyrrol-2-yl)butyl)-2-methyloct-7-ynamide (1d): (62%); $[\alpha]^{20}_D$ 60.0 (c 0.07, MeOH); $^1$H NMR (600 MHz, CDCl$_3$) δ ppm: 5.44 (br t, J=6.0 Hz, 1H), 5.06 (s, 1H), 4.64 (dd, J=5.4, 3.0 Hz, 1H), 3.85 (s, 3H), 3.77 (sextet, J=6.6 Hz, 1H), 3.26-3.20 (m, 1H), 3.18-3.13 (m, 1H), 2.20-2.16 (m, 4H), 2.15-2.07 (m, 2H), 1.93 (t, J=3.0 Hz, 1H), 1.92 (t, J=3.0 Hz, 1H), 1.83 (dddd, J=13.8, 11.4, 6.0, 3.0 Hz, 1H), 1.77-1.72 (m, 1H), 1.64-1.62 (m, 1H), 1.54-1.46 (m, δH), 1.44-1.34 (m, δH), 1.21-1.16 (m, 4H), 1.16-1.10 (m, 4H); $^{13}$C NMR (150 MHz, CDCl$_3$) δ ppm: 179.2, 177.0, 176.4, 170.0, 94.3, 84.7, 84.6, 68.5, 68.3, 59.2, 58.9, 41.7, 39.3, 39.2, 33.9, 32.5, 29.9, 29.5, 29.0, 28.7, 28.5, 26.7, 26.6, 20.2, 18.5, 18.4, 18.1, 18.1; HRMS (ESI) m/z calcd for C$_{27}$H$_{41}$N$_2$O$_4$ [M+H]$^+$ 457.3061, found 457.3058.

The following compounds were prepared according to aforementioned procedures:

(doscadenamide S13)

(doscadenamide S14)

(doscadenamide S8)

(doscadenamide S10)

-continued (doscadenamide S6)

(dosadenamide S5)

(doscadenamide J)

(doscadenamide S7)

(doscadenamdie S4)

Isolation and Characterization of Doscadenamides B-I

Here we describe the identification of additional natural doscadenamides (B-I) from the same cyanobacterium and the synthesis of strategically diversified analogues to also probe the structure-activity relationship (SAR) with respect to QS modulation in several different gram-negative bacterial systems, and interrogated the tentatively causative molecular interactions with bacterial receptors. We then evaluated a subset of the focused doscadenamide library in in cancer cells and successfully established a synergistic activity with TRAIL in invasive triple negative breast cancer cells, Careful chemical investigation of the original extracts enabled to identification of several related compounds that differed in the degree of unsaturation and methylation pattern (FIG. 1). Rigorous 1D and 2D NMR analysis coupled with HRMS and synthesis of selected family members unambiguously established the structures of the additional doscadenamides. Five pure structural analogs were isolated, doscadenamides B-F (1b-1f, FIG. 1) as well as impure doscadenamides G-J (1g-j, FIG. 1).

Doscadenamide B [1b; $t_R$=10.1 min; 1.2 mg; white solid; HRESIMS [M+H]$^+$ peak at m/z 455.2904, which suggested a molecular formula $C_{27}H_{38}N_2O_4$.

Doscadenamide C [(1c, $t_R$=13.7 min, 0.8 mg): white solid; HRESIMS [M+H]$^+$ peak at m/z 459.3218, which suggested a molecular formula $C_{27}H_{42}N_2O_4$.

Doscadenamide D [(1d, $t_R$=14.7 min, 0.8 mg): white solid; HRESIMS [M+H]$^+$ peak at m/z 459.3226, which suggested a molecular formula $C_{27}H_{42}N_2O_4$.

Doscadenamide E [(1e, $t_R$=9.4 min, 0.1 mg): white solid; HRESIMS [M+H]$^+$ peak at m/z 445.3069, which suggested a molecular formula $C_{26}H_{40}N_2O_4$.

Doscadenamide F [(1f, $t_R$=12.4 min, 0.8 mg): white solid; HRESIMS [M+H]$^+$ peak at m/z 461.3362, which suggested a molecular formula $C_{27}H_{44}N_2O_4$.

Doscadenamide G [(1f, $t_R$=13.9 min, 0.3 mg): white solid; HRESIMS [M+H]$^+$ peak at m/z 445.3063, which suggested a molecular formula $C_{27}H_{42}N_2O_4$.

Doscadenamide I/J [(1i/1j, $t_R$=9.4 min, 0.5 mg, mixture), HRESIMS [M+H]$^+$ peak at m/z 442.2916, which suggested a molecular formula $C_{26}H_{38}N_2O_4$.

We were not able to obtain pure doscadenamide G (1g, FIG. 1); therefore, based on our established synthetic route, we synthesized the compound with the proposed structure (Scheme 1) and compared its $^1$H NMR spectrum with the isolated fraction, confirming the dominant presence of doscadenamide H (1h). The proposed doscadenamides H (1i) and J (1j) coeluted under various HPLC conditions and were present in roughly equal abundance (1:1 mixture). To confirm our hypothesis, we synthesized the two compounds, establishing the structures.

Scheme 1. Total synthesis of doscadenamide H (1h).

Doscadenamide H (1h)

Synthesis of a Strategic Focused Library to Probe the SAR

In addition to doscadenamides that are biosynthesized through natural diversification, we aimed to prepare a complementary compound set that possessed different degrees of methylation and/or unsaturation in the carboxylic acid chains (1j-1m), lacked one of the carboxylic acid chains (2a,b vs. 3a-3c), exhibited different pyrrolinone configuration (1n) or transposed pyrrolinone functionalization (10), as well as a cyclized version (4a) (FIG. 1). We termed these new synthetic analogues doscadenamides S4-S15 (FIG. 1). The diastereomers of 1a were denominated as doscadenamides S1-S3 (FIG. 18).

To explore the contribution of each structural characteristics in doscadenamide A (1a, FIG. 1) to the interaction with its target and its biological activity, we synthesized most of these structural analogs (doscadenamides F-J, 1f-1j) following similar approach as previously described for 1a and exemplified for the synthesis of doscadenamide H (1h, Scheme 1). Each target compound can be obtained in three main steps: pyrrolinone ring construction, carboxylic acid activation and amide/imide coupling. For certain analogs (1f, 1k, 1l, 1m, 2b, 3b and 3c), we synthesized additional carboxylic acids as specific building blocks to prepare the desired products.

Our preliminary study indicates that the diastereomeric doscadenamides S1-S3 behave similarly in modulating QS in *Pseudomonas aeruginosa*. To perform the SAR study of doscadenamides systematically, we selected several analogs to compose a focused library for primary studies (FIG. 1, highlighted). To explore the contribution of the unsaturated alkyne moiety to the bioactivity of doscadenamide A (1a, FIG. 1), we included structural analogs with two unsaturated alkene termini (if, FIG. 1) and two saturated carboxylic acid moieties (1k, FIG. 1). To further investigate the significance of each side chain in doscadenamides, we included structural analogs 2a and 3a-3c, possessing only one carboxylic acid chain and with different degrees of unsaturation (3a-3c). To confirm the importance of the linear structure of doscadenamide A (1a, FIG. 1), the cyclic compound 4a was also included in the library.

Total Synthesis of Doscadenamides

Scheme 1. Typical synthetic route for target molecules.

3a

-continued

1a

Scheme 1 is a useful synthetic route for 1a. This synthetic strategy was generalized to construct other analogs of (FIG. 1). The reaction conditions were adjusted for the minority of compounds. Various analogs of 5a as well as 6a (below) have been synthesized using general methods, and the combination of building blocks of 5a analogs with 6a analogs provided the series of target molecules (1a-p, 2a, b, 3a-c, and 4a).

5a

5b

6a

6b

6c

6d

-continued

6e

6f

6g

Scheme 2. Synthesis of building blocks 5b, 5c.

a) for 5b

8b

Meldrum's acid i) DCC, DMAP
ii) EtOAc, Δ

9b

TMSCHN₂

Et₂O:MeOH = 4:1

10b piperidine

MeCN

93%

5b

-continued b) for 5c

9a

TMSCHN₂
EtO:MeOH = 4:1
48%

10a (50%)

\+

10c (18%)

MeCN
88%  Piperidine

5c

Similar to the synthesis of 5a and corresponding intermediates, 5b, 5c and corresponding intermediates were synthesized.

Synthesis of compounds 10b. To the solution of N-Fmoc-D-Lys (Boc)-OH (1.0 g, 2.13 mmol) and meldrum acid (338.4 mg, 2.35 mmol) in anhydrous CH₂Cl₂ (20 ml) at 0° C. was added 4-Dimethylaminopyridine (DMAP) (391 mg, 3.20 mmol) and EDCI·HCl (530 mg, 2.77 mmol). After being stirred overnight at room temperature, the reaction solution was diluted with EtOAc (60 ml), washed by 5% citric acid (aq.) (20 ml×4) and brine (20 ml×2), dried over anhydrous MgSO₄. The filtered EtOAc phase was refluxed under heating for 30 min, then cooled down to room temperature and evaporated to give crude intermediate 9b, which was used in next step without purification.

To a solution of the above crude 9b in the mixture of diethyl ether (160 ml) and methanol (40 ml) was added trimethylsilyldiazomethane (TMSCHN₂) (4.4 ml, 8.79 mmol). The resulting mixture was stirred overnight at room temperature, then concentrated under reduced pressure. The residue was dissolved in EtOAc (150 ml), washed with 5% citric acid (aq.) (30 ml×3), sat. NaHCO₃ (30 ml×2 and brine (30 ml), dried over anhydrous MgSO₄, and evaporated in vacuo. Product 10b was obtained after the crude was purified by chromatography column on silica gel (eluted by 50-70% ethyl acetate in hexane).

Compound 10b (500.0 mg, 45.0% 2 steps). $[\alpha]^{20}_D$: −72.5 (c 0.1, MeOH). ¹H NMR (600 MHz, CDCl₃): δ 7.77-7.73 (m, 4H), 7.40 (t, J=7.2 Hz, 2H), 7.33 (t, J=7.2 Hz, 2H), 5.09 (s, 1H), 4.58 (m, 2H), 4.48 (br s, 1H), 4.36 (dd, J=5.4, 3.0 Hz, 1H), 4.33 (t, J=6.6 Hz, 1H), 3.83 (s, 3H), 3.08-2.98 (m, 2H), 1.85-1.79 (m, 1H), 1.71 (dddd, J=14.4, 11.4, 4.8, 3.0 Hz, 1H), 1.44 (s, 9H), 1.38-1.31 (m, 2H), 1.19-1.11 (m, 1H), 1.03-0.96 (m, 1H) ppm. ¹³C NMR (125 MHz, CDCl₃): δ 178.0, 168.8, 155.0, 151.1, 143.8, 143.7, 141.5, 141.4, 128.0, 127.9, 127.4, 125.4, 125.4, 120.1, 120.1, 94.5, 79.3, 68.1, 59.9, 58.8, 46.9, 40.5, 29.9, 28.7, 28.6, 19.6 ppm HRMS (ESI) m/z calcd for C₂₉H₃₄N₂O₆ [M+H]⁺ 507.2490, found 507.2492.

Compound 10c. In the methylation of pyrrolidine 9a previously[2], both 4- and 2-carbonyls were methylated to give corresponding products 10a (50%) and 10c (18%), which were separable with chromatography silica column. (18.2% from 9a). $[\alpha]^{20}_D$: −28.0 (c 0.1, MeOH). ¹H NMR (600 MHz, CDCl₃): δ 7.78-7.77 (m, 2H), 7.58-7.55 (m, 2H), 7.43-7.40 (m, 2H), 7.35-7.31 (m, 2H), 4.82 (s, 1H), 4.73 (m, 2H), 4.45 (br s, 1H), 4.25 (t, J=4.8 Hz, 1H), 3.92 (s, 3H), 3.85-3.83 (m, 1H), 3.00-2.98 (m, 2H), 1.68-1.64 (m, 1H), 1.54-1.47 (m, 1H), 1.44 (s, 9H), 1.28-1.22 (m, 2H), 1.10-1.03 (m, 1H), 1.02-0.95 (m, 1H) ppm. ¹³C NMR (150 MHz, CDCl₃): δ 195.9, 176.6, 156.0, 149.5, 143.5, 143.4, 141.7, 141.6, 128.1, 128.1, 127.4, 127.4, 124.6, 124.5, 120.3, 120.3, 86.6, 79.2, 67.7, 66.1, 59.7, 47.0, 40.4, 29.9, 29.4, 28.6, 19.7 ppm. HRMS (ESI) m/z calcd for C₂₉H₃₄N₂O₆ [M+H]⁺ 507.2490, found 507.2491.

Synthesis of compounds 5b and 5c. Piperidine (2.0 ml) was added to the solution of 10b or 10c (366.3 mg, 0.723 mmol) at room temperature. After stirred at the same temperature for 15 min, the reaction solution was concentrated and co-evaporated with toluene for 3 times. The residue was purified by chromatography column on silica gel (eluted by EtOAc/hexane 1:1, then by 3-3.5% MeOH in CH₂Cl₂) to provide product 5b or 5c.

Compound 5b (93%). $[\alpha]^{20}_D$: −21.5 (c 0.1, MeOH). ¹H NMR (600 MHz, CDCl₃): δ 6.23 (br s, 1H), 5.01 (s, 1H), 4.72 (t, J=6.0 Hz, 1H), 4.04 (dd, J=7.2, 3.6 Hz, 1H), 3.78 (s, 3H), 3.16-3.06 (m, 2H), 1.83-1.78 (m, 1H), 1.56-1.47 (m, 3H), 1.47-1.41 (m, 10H), 1.36-1.30 (m, 1H) ppm. ¹³C NMR (150 MHz, CDCl₃): δ 178.3, 174.5, 156.2, 93.7, 79.3, 58.5, 57.4, 40.3, 31.5, 29.9, 28.6, 22.1 ppm HRMS (ESI) m/z calcd for C₁₄H₂₄N₂O₄ [M+H]⁺ 285.1809, found 285.1806.

Compound 5c (88%). $[\alpha]^{20}_D$: −39.0 (c 0.1, MeOH). ¹H NMR (600 MHz, CDCl₃): δ 5.69 (br s, 1H), 4.66-4.64 (m, 2H), 3.89 (s, 3H), 3.75-3.73 (m, 1H), 3.13-3.07 (m, 2H), 1.91-1.85 (br m, 1H), 1.66-1.60 (m, 1H), 1.53-1.47 (m, 2H), 1.44-1.37 (m, 11H) ppm. 13C NMR (150 MHz, CDCl₃): δ 199.3, 181.6, 156.4, 80.4, 79.4, 63.5, 58.4, 40.1, 30.8, 30.0, 28.6, 22.2 ppm. HRMS (ESI) m/z calcd for C₁₄H₂₄N₂O₄ [M+H]⁺ 285.1809, found 285.1807.

Scheme 3. Synthesis of 6d/e/g.

Synthesis of 11a and 11b. To a solution of 7-Octenoic acid (Oea)(450 mg, 3.17 mmol) and trimethylamine (Et₃N) (0.56 mL, 4.13 mmol) in THF (18 mL) at –20° C. was added neat 2,2-trimethylacetyl chloride (0.43 mL, 3.49 mmol) dropwise over 20 min. The resulting mixture was stirred at –20° C. for 30 min and 0° C. for another 30 min, then it was cooled to –78° C. by dry ice-acetone. In another reaction flask, n-butyllithium (n-BuLi) (1.6 M in n-hexane) (2.0 ml, 3.17 mmol) was added dropwise to a solution of R- or S-oxazolidione (841 mg, 4.75 mmol) in tetrahydrofuran at –78° C. The mixture was stirred at this temperature for 20 min and then transferred to the above solution of Oya in THF at –78° C. by canula. The resulting mixture was stirred at this temperature for 30 min, then it was allowed to warm to room temperature and stirred for 1.5 h. The reaction was quenched with saturate NH₄C₁ (aq) solution, extracted with EtOAc (45 mL×3), washed by 5% NaHCO₃ solution, dried over anhydrous MgSO₄ and concentrated in vacuo. The residue was purified by silica gel chromatography column (eluted by 15% ethyl acetate in hexane) to give products 11a or 11b, corresponding to R- or S-oxazolidione, respectively.

Compound 11a (451 mg, 78%). [α]²⁰_D: –97.0 (c 0.1, MeOH). ¹H NMR (600 MHz, CDCl₃): δ 7.35-7.32 (t m, 2H), 7.29-7.26 (t m, 1H), 7.22-7.20 (d m, 2H), 5.81 (ddt, J=17.5, 10.2, 6.6 Hz, 1H), 5.02-4.93 (m, 2H), 4.67 (ddt, J=10.8, 7.8, 3.0 Hz, 1H), 4.21-4.15 (m, 2H), 3.30 (dd, J=13.2, 3.0 Hz, 1H), 3.00-2.87 (m, 2H), 2.77 (dd, J=13.2, 9.6 Hz, 1H), 2.09-2.05 (m, 2H), 1.75-1.65 (m, 2H), 147-1.38 (m, 4H) ppm. ¹³C NMR (125 MHz, CDCl₃): δ 173.5, 153.6, 139.0, 135.5, 129.6, 129.1, 127.5, 114.6, 66.3, 55.3, 38.1, 35.6, 33.7, 28.8, 28.7, 24.2 ppm. HRMS (ESI) m/z calcd for $C_{18}H_{23}NO_3$ [M+H]$^+$ 302.1751, found 302.1748.

Compound 11b (907 mg, 95%). [α]$^{20}{}_D$: 85.0 (c 0.1, MeOH). $^1$H NMR (600 MHz, CDCl$_3$): δ 7.35-7.32 (t m, 2H), 7.29-7.26 (t m, 1H), 7.22-7.20 (d m, 2H), 5.81 (ddt, J=17.4, 10.2, 6.6 Hz, 1H), 5.02-4.93 (m, 2H), 4.67 (ddt, J=10.8, 7.8, 3.0 Hz, 1H), 4.21-4.15 (m, 2H), 3.30 (dd, J=13.2, 3.0 Hz, 1H), 3.00-2.87 (m, 2H), 2.77 (dd, J=13.2, 9.6 Hz, 1H), 2.09-2.05 (m, 2H), 1.76-1.65 (m, 2H), 147-1.38 (m, 4H) ppm. $^{13}$C NMR (125 MHz, CDCl$_3$): δ 173.5, 153.6, 139.0, 135.5, 129.6, 129.1, 127.5, 114.6, 66.3, 55.3, 38.1, 35.6, 33.7, 28.8, 28.7, 24.2 ppm. HRMS (ESI) m/z calcd for $C_{18}H_{23}NO_3$ [M+H]$^+$ 302.1751, found 302.1746.

Synthesis of compounds 12a and 12b. To a solution of sodium bis(trimethylsilyl)amide (NaHMDS) (2.0 M in THF) (1.11 ml, 2.21 mmol) in anhydrous THF (9 ml) at −78° C. was added compound 11a or 11b (609 mg, 2.02 mmol) in THF (3.5 ml) under argon atmosphere. After the resulting reaction solution was stirred at the same temperature for 30 min, neat MeI (0.63 ml, 10.08 mmol) was added dropwise over 10 min. The reaction mixture was quenched with saturate NH$_4$Cl (aq.) (18 ml) after it was stirred at −78° C. for 20 h, then extracted with ethyl acetate (25 ml×3), dried over anhydrous MgSO$_4$, and concentrated in vacuo. The residue was purified by chromatography column of silica gel (eluted by 8% ethyl acetate in hexane) to give product 12a or 12b, corresponding to 11a, 11b, respectively.

Compound 12a (566 mg, 89%). [α]$^{20}{}_D$: −70.0 (c 0.1, MeOH). $^1$H NMR (600 MHz, CDCl$_3$): δ 7.34-7.31 (m, 2H), 7.29-7.26 (m, 1H), 7.22-7.21 (m, 2H), 5.79 (ddt, J=17.4, 10.2, 6.6 Hz, 1H), 5.01-4.92 (m, 2H), 4.68 (ddt, J=9.6, 7.8, 3.0 Hz, 1H), 4.21-4.16 (m, 2H), 3.70 (h, J=6.6 Hz, 1H), 3.27 (dd, J=13.2, 3.0 Hz, 1H), 2.77 (dd, J=13.2, 9.6 Hz, 1H), 2.05 (qt, J=7.0, 1.2 Hz, 2H), 1.78-1.72 (m, 1H), 1.46-1.36 (m, 3H), 1.36-1.29 (m, 2H), 1.22 (d, J=6.6 Hz, 3H) ppm. $^{13}$C NMR (150 MHz, CDCl$_3$): δ 177.4, 153.2, 139.0, 135.5, 129.6, 129.1, 127.5, 114.6, 66.2, 55.5, 38.1, 37.8, 33.7, 33.4, 29.0, 26.8, 17.5 ppm. HRMS (ESI) m/z calcd for $C_{19}H_{25}NO_3$ [M+H]$^+$ 316.1907, found 316.1901.

Compound 12b (608 mg, 69%). [α]$^{20}{}_D$: 99.0 (c 0.1, MeOH). $^1$H NMR (500 MHz, CDCl$_3$): δ 7.33 (t, J=7.5 Hz, 2H), 7.27 (t, J=7.0 Hz, 1H), 7.21 (d, J=7.0 Hz, 2H), 5.79 (ddt, J=17.0, 10.0, 7.0 Hz, 1H), 5.00-4.92 (m, 2H), 4.70-4.65 (m, 1H), 4.21-4.15 (m, 2H), 3.70 (sextet, J=6.5 Hz, 1H), 3.26 (dd, J=13.5, 3.5 Hz, 1H), 2.77 (dd, J=13.5, 9.5 Hz, 1H), 2.04 (q, J=7.0 Hz, 2H), 1.79-1.71 (m, 1H), 1.46-1.36 (m, 3H), 1.35-1.28 (m, 2H), 1.22 (d, J=7.0 Hz, 3H) ppm. $^{13}$C NMR (125 MHz, CDCl$_3$): δ 177.4, 153.2, 139.0, 135.5, 129.6, 129.0, 127.5, 114.5, 66.1, 55.5, 38.0, 37.8, 33.7, 33.3, 29.0, 26.8, 17.5 ppm HRMS (ESI) m/z calcd for $C_{19}H_{25}NO_3$ (M+X)+[M+H]$^+$ 316.1907, found 316.1902.

Synthesis of acid 6d, 6e. Hydrogen peroxide (30% in H$_2$O) (0.7 ml, 6.12 mmol) was added to the solution of 12a or 12b (480 mg, 1.52 mmol) in the mixture of THF·H$_2$O (10 ml-5 ml) at 0° C. LiOH·H$_2$O (128.4 mg, 3.06 mmol) was added to the above reaction solution after it was stirred at 0° C. for additional 10 min. Then the resulting reaction mixture was stirred at 0° C. for 2 h and additional 1 h at room temperature, then Na$_2$SO$_3$ (965.2 mg) was added. The quenched reaction was diluted with water (25 ml) and EtOAc (25 ml). Ethyl acetate phase was separated and the separated water phase was acidified with 1M aq. HCl (to pH 2) and extracted EtOAc (25 ml×3). The combined EtOAc phase was dried over anhydrous MgSO$_4$, concentrated in vacuo and purified by silica gel column chromatography (eluted by 17% ethyl acetate in hexane). to give product 6d or 6e, corresponding to 12a, 12b, respectively.

Acid 6d (246 mg, 92%). [α]$^{20}{}_D$: −23.0 (c 0.1, MeOH). $^1$H NMR (600 MHz, CDCl$_3$): 5.79 (ddt, J=16.8, 10.2, 6.6 Hz, 1H), 5.01-4.92 (m, 2H), δ 2.46 (sextet, J=7.2 Hz, 1H), 2.05 (qt, J=8.4, 1.2 Hz, 2H), 1.72-1.67 (m, 1H), 1.47-1.32 (m, 5H), 1.18 (d, J=6.6 Hz, 3H) ppm. $^{13}$C NMR (150 MHz, CDCl$_3$): δ 183.3, 138.9, 114.6, 39.5, 33.7, 33.5, 28.9, 26.7, 17.0 ppm. HRMS (ESI) m/z calcd for $C_9H_{16}O_2$ [M+H]$^+$ 157.1223, found 157.1222.

Acid 6e (148.3, 62%). [α]$^{20}{}_D$: 13.0 (c 0.1, MeOH). $^1$H NMR (600 MHz, CDCl$_3$): 5.79 (ddt, J=16.8, 10.2, 6.6 Hz, 1H), 5.01-4.92 (m, 2H), δ 2.46 (sextet, J=7.2 Hz, xz1H), 2.05 (qt, J=8.4, 1.8 Hz, 2H), 1.72-1.66 (m, 1H), 1.47-1.32 (m, 5H), 1.18 (d, J=7.2 Hz, 3H) ppm. $^{13}$C NMR (150 MHz, CDCl$_3$): δ 183.4, 138.9, 114.6, 39.5, 33.7, 33.5, 28.9, 26.7, 17.0 ppm. HRMS (ESI) m/z calcd for $C_9H_{16}O_2$ [M+H]$^+$ 157.1223, found 157.1219.

Synthesis of acid 6g. Though acid 6g is a known and commercially available compound, we prepared it conveniently from the available material in lab. Acid 6d (33 mg, 0.211 mmol) was stirred under hydrogen atmosphere in MeOH (2.0 mL) for 30 min, then the reaction mixture was filtered and evaporated to provide acid 6g (30 mg, 90%).

Acid 6g (30 mg, 90%); [α]$^{20}{}_D$: −22.0 (c 0.15, MeOH); $^1$H NMR (600 MHz, CDCl$_3$): δ 2.45 (ddq, J=6.7 Hz, 1H), 1.71-1.65 (m, 1H), 1.45-1.40 (m, 1H), 1.34-1.27 (m, 8H), 1.17 (d, J=7.0 Hz, 3H), 0.88 (t, J=6.8 Hz, 3H) ppm. $^{13}$C NMR (150 MHz, CDCl$_3$): δ 182.9, 39.6, 33.8, 31.8, 29.3, 27.3, 22.8, 17.0, 14.2 ppm. HRMS (ESI) m/z calcd for $C_9H_{16}O_2$(M−H)$^-$ 157.1229, found 157.1232.

Scheme 4. Synthesis of 3a-e and 1f, h-n.

a)

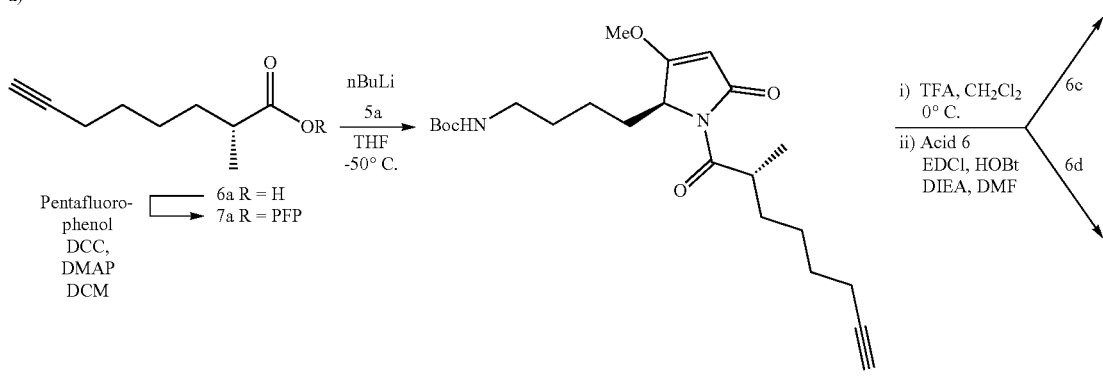

Doscadenamide S10 (3a)

-continued
Doscadenamide J (1j)
Doscadenamide S7 (1n)
b)
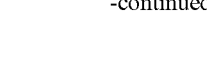
Pentafluoro-
phenol
DCC,
DMAP
DCM
6c R = H
7c R = PFP
nBuLi
5a
THF
-50° C.
BocHN
3d
i) TFA, CH₂Cl₂
0° C.
ii) Acid 6
EDCl, HOBt
DIEA, DMF
6a
6b -continued Doscadenamide I (1i)

Doscadenamide S6 (1m)

c)

Doscadenamide S11 (3b)

Doscadenamide F (1f)

-continued d)

3e

Doscadenamide H (1h)

Doscadenamide S5 (1l)

e)

Doscadenamide S12 (3c)

-continued

Doscadenamide S4 (1k)

Scheme 5. Synthesis of 1o and 1p.

a)

5b 7a
nBuLi
THF
-50° C.

3f i) TFA, CH₂Cl₂
0° C.

ii) Acid 6a
EDCl, HOBt
DIEA, DMF

-continued

3g i) TFA, CH₂Cl₂
0° C.

ii) Acid 6a
EDCl, HOBt
DIEA, DMF

DoscadenamideS14 (1p)

DoscadenamideS13 (1o)

b)

5c

7a
KHMDS
THF
-50° C.
27%

General procedure for the synthesis of PFP ester 7 (Scheme 4). To the solution of an acid 6 (0.1 mmol) in anhydrous CH₂Cl₂ (3.0 mL) at 0° C. was added pentafluorophenol (40.1 mg, 0.22 mmol) in anhydrous CH₂Cl₂ (0.5 mL), DMAP (2.4 mg, 0.02 mmol) and DCC (49.5 mg, 0.24 mmol). The resulting reaction mixture was stirred at room temperature overnight and concentrated under reduced pressure. The residue was stirred in cooled EtOAc (3.0 mL), and the suspending solid was filtered off. The filtrate was evaporated in vacuo and purified with silica gel column chromatography (eluted by 7% EtOAc in hexane) to yield the corresponding PFP ester 7 as white solid.

General procedure for the synthesis of 3a-e (Scheme 4). To a solution of 5a (6.2 mg, 0.02 mmol) in anhydrous THF (1.0 mL) at −55° C. was added nBuLi (1.6 M in n-hexane) (0.021 mL, 0.033 mmol), the solution was stirred the same temperature for 30 min. Subsequently, the activated carboxylic corresponding acid 7 (0.03 mmol) in anhydrous THF (0.5 mL) was added dropwise at −55° C. The resulting reaction mixture was stirred at the same temperature for 3 h and then room temperature overnight. The reaction was quenched on the next day with saturate NH₄Cl (aq, 3.0 mL) and then extracted with EtOAc (5 mL×3). The combined organic phase was washed with saturate NaHCO₃ (aq, 5 mL×2) and brine (5 mL), dried over anhydrous MgSO₄, and purified by preparative TLC plate of silica gel to yield corresponding product 3 as white solid. For the synthesis of 3f (Scheme 5a)), use 5b instead of 5a to couple with PFP ester 7a following the above general procedure; For the synthesis of 3g (Scheme 5b)), nBuLi was replaced by KHMDS (0.7 M in toluene) and use 5c instead of 5a to couple with PFP ester 7a following the above general procedure.

General procedure for the synthesis of 1a-g (Schemes 4 and 5). To the solution of corresponding 3 (0.010 mmol) in CH₂Cl₂ (1.5 mL) was added TFA (0.75 mL) at 0° C. and the mixture was stirred the same temperature for 30 min. The reaction was diluted with toluene (1 mL) and evaporated in vacuo (3 times) to produce an intermediate crude, which was used in next step without purification. To the intermediate crude in anhydrous DMF (1.0 mL) was added corresponding acid 6 (0.011 mmol), EDCI·HCl (3.4 mg, 0.017 mmol), HOBt-H₂O (2.8 mg, 0.018 mmol) and DIEA (6.0 μL). The reaction mixture was stirred at room temperature for 20 h and then was evaporated in vacuo and purified by preparative TLC plate to yield corresponding product doscadenamide 1 as white solid.

PFP ester 7c (91.5%). ¹H NMR (600 MHz, CDCl₃): δ 2.68 (t, J=7.2 Hz, 2H), 2.23 (td, J=6.6, 2.4 Hz, 2H), 1.96 (t, J=3.0 Hz, 1H), 1.80 (p, J=7.8 Hz, 2H), 1.62-1.52 (m, 4H) ppm. ¹³C NMR (150 MHz, CDCl₃): δ 169.5, 142.1 (m), 140.5 (m), 138.8 (m), 137.2 (m), 125.3 (m), 84.2, 68.7, 33.3, 28.1, 28.0, 24.4, 18.4 ppm. HRMS (ESI) m/z calcd for C₁₄H₁₁F₅O₂ [M+H]⁺ 307.0757, found 307.0760.

PFP ester 7d (85%). [α]²⁰_D: −96.0 (c 0.03, MeOH); ¹H NMR (600 MHz, CDCl₃): δ 5.81 (ddt, J=16.9, 10.2, 6.7 Hz, 1H), 5.03-4.94 (m, 2H), 2.81 (ddq, J=7.0 Hz, 1H), 2.10-2.06 (m, 2H), 1.86-1.80 (m, 1H), 1.63-1.56 (m, 1H) ppm, 1.48-1.40 (m, 4H), 1.33 (d, J=7.0 Hz). ¹³C NMR (150 MHz, CDCl₃): δ 172.8, 142.2 (m), 140.4 (m), 138.7 (m), 138.7, 137.2 (m), 125.4 (m), 114.7, 39.4, 33.7, 33.6, 28.8, 26.6, 17.1 ppm. HRMS (ESI) m/z calcd for C₁₅H₁₅F₅O₂ (M+H)⁺ 323.1070, found 323.1068.

PFP ester 7f (84%). ¹H NMR (600 MHz, CDCl₃): δ 5.81 (ddt, J=17.4, 10.8, 6.6 Hz, 1H), 5.03-4.95 (m, 2H), 2.67 (t, J=7.2 Hz, 2H), 2.10-2.06 (m, 2H), 1.81-1.76 (m, 2H), 1.48-1.42 (m, 4H) ppm. ¹³C NMR (150 MHz, CDCl₃): δ 169.7, 142.1 (m), 140.5 (m), 138.9 (m), 138.7, 137.2 (m), 125.3 (m), 114.8, 33.6, 33.4, 28.5, 28.4, 24.8 ppm. HRMS (ESI) m/z calcd for C₁₄H₁₃F₅O₂ [M+H]⁺ 309.0914, found 309.0918.

PFP ester 7g (90%). [α]²⁰_D: −25.0 (c 0.15, MeOH); ¹H NMR (600 MHz, CDCl₃): δ 2.80 (ddq, J=7.0 Hz, 1H), 1.81 (dq, J=13.6, 7.7, 1H), 1.62-1.57 (m, 1H), 1.42-1.36 (m, 2H), 1.36-1.28 (m, 9H), 0.89 (t, J=6.8 Hz, 3H) ppm. ¹³C NMR (150 MHz, CDCl₃): δ 172.9, 142.2 (m), 140.5 (m), 138.8 (m), 138.8, 137.2 (m), 125.5 (m), 114.7, 39.5, 33.7, 31.8, 29.2, 27.1, 22.7, 17.1, 14.2 ppm. HRMS (ESI) m/z calcd for C₁₅H₁₈F₅O₂ [M+H]⁺ 325.1227, found 325.1222.

Doscadenamide S10 (3a) [α]²⁰_D 65.0 (c 0.1, MeOH); ¹H NMR (600 MHz, CDCl₃) δ ppm: 5.04 (s, 1H), 4.65 (dd, J=5.4, 3.0 Hz, 1H), 4.51 (br s, 1H), 3.84 (s, 3H), 3.77 (sextet, J=6.6 Hz, 1H), 3.09-3.01 (m, 2H), 2.18 (td, J=6.6, 2.4 Hz, 2H), 2.08 (ddt, J=13.8, 11.4, 5.4 Hz, 1H), 1.93 (t, J=3.0 Hz, 1H), 1.83 (dddd, J=13.8, 11.4, 5.4, 3.0 Hz, 1H), 1.78-1.71 (m, 1H), 1.57-1.49 (m, 2H), 1.48-1.39 (m, 14H), 1.21-1.14 (m, 1H), 1.12-1.06 (m, 4H); ¹³C NMR (150 MHz, CDCl₃) δ ppm: 179.1, 177.0, 170.1, 156.1, 94.3, 84.6, 79.3, 68.5, 59.2, 58.8, 40.5, 39.1, 33.7, 30.0, 28.8, 28.6, 28.5, 26.4, 20.0, 18.5, 18.3; HRMS (ESI) m/z calcd for C₂₃H₃₇N₂O₅ [M+H]⁺ 421.2697, found 421.2692.

Doscadenamide S11 (3b) (67%). [α]²⁰_D: 24.0 (c 0.04, MeOH); ¹H NMR (600 MHz, CDCl₃): δ 5.78 (ddt, J=16.9, 10.2, 6.6 Hz, 1H), 5.04 (s, 1H), 5.00-4.90 (m, 2H), 4.65 (dd, J=5.7, 3.0 Hz, 1H), 4.48 (br s, 1H), 3.84 (s, 3H), 3.10-3.01 (m, 2H), 2.08 (ddt, J=18.3, 9.9, 4.7 Hz, 1H), 2.03 (dt, J=7.1, 7.1 Hz, 2H), 1.83 (dddd, J=14.2, 11.3, 5.4, 3.1 Hz, 1H), 1.74-1.72 (m, 1H), 1.67-1.63 (m, 1H), 1.45-1.37 (m, 14H), 1.36-1.29 (m, 2H), 1.20-1.14 (m, 1H), 1.13-1.08 (m, 4H) ppm. ¹³C NMR (150 MHz, CDCl₃): δ 179.1, 177.1, 170.0, 156.0, 139.0, 114.5, 94.3, 79.3, 59.2, 58.8, 40.5, 39.2, 34.1, 33.8, 29.9, 29.0, 28.8, 28.6, 26.7, 20.0, 16.3 ppm. HRMS (ESI) m/z calcd for C₂₃H₃₈N₂O₅ [M+Na]⁺445.2678, found 471.2670.

Doscadenamide S12 (3c) (56%). [α]²⁰_D: 48.0 (c 0.033, MeOH); ¹H NMR (600 MHz, CDCl₃): δ 5.04 (s, 1H), 5.00-4.90 (m, 2H), 4.66 (dd, J=5.6, 3.0 Hz, 1H), 4.48 (br s, 1H), 3.84 (s, 3H), 3.76 (ddq, J=6.7, 6.7, 6.7 Hz, 2H), 3.10-3.01 (m, 2H), 2.08 (ddt, J=13.9, 10.9, 5.3 Hz, 1H), 1.83 (dddd, J=14.1, 11.3, 5.5, 3.1 Hz, 1H), 1.75-1.70 (m, 1H), 1.48-1.37 (m, 13H), 1.30-1.25 (m, 7H), 1.19-1.15 (m, 1H), 1.14-1.06 (m, 4H) ppm. ¹³C NMR (150 MHz, CDCl₃): δ 179.0, 177.2, 170.0, 156.0, 94.3, 79.3, 59.2, 58.8, 40.5, 39.2, 34.4, 32.0, 29.5, 28.8, 28.6, 27.2, 22.8, 20.0, 16.3, 14.2 ppm. HRMS (ESI) m/z calcd for C₂₃H₄₀N₂O₅ [M+Na]⁺447.2835, found 447.2825.

Compound 3d (71%). [α]²⁰_D: 60.0 (c 0.1, MeOH). ¹H NMR (600 MHz, CDCl₃): δ 5.05 (s, 1H), 4.64 (dd, J=5.4, 3.0 Hz, 1H), 4.49 (br s, 1H), 3.85 (s, 3H), 3.08-3.03 (m, 2H), 2.99-2.88 (m, 2H), 2.20 (td, J=6.6, 2.4 Hz, 2H), 2.12 (ddt, J=13.8, 11.4, 5.4 Hz, 1.93 (t, J=3.0 Hz, 1H), 1.84 (dddd, J=13.8, 11.4, 5.4, 3.0 Hz, 1H), 1.67 (p, J=7.2 Hz, 2H), 1.59-1.55 (m, 2H), 1.50-1.45 (m, 4H), 1.43 (s, 9H), 1.25-1.14 (m, 1H), 1.13-1.05 (m, 1H) ppm. ¹³C NMR (150 MHz, CDCl₃): δ 179.1, 173.0, 170.3, 156.1, 94.2, 84.7, 79.3, 68.4, 59.2, 58.8, 40.5, 37.1, 30.0, 28.8, 28.6, 28.5, 28.4, 24.1, 20.0, 18.4 ppm. HRMS (ESI) m/z calcd for C₂₂H₃₄N₂O₅ [M+H]⁺ 407.2546, found 407.2549.

Compound 3e (62%). [α]²⁰_D: 65.0 (c 0.1, MeOH). ¹H NMR (600 MHz, CDCl₃): δ 5.80 (ddt, J=17.4, 10.8, 6.6 Hz, 1H), 5.05 (s, 1H), 5.01-4.91 (m, 2H), 4.64 (dd, J=5.4, 3.0 Hz, 1H), 4.48 (br s, 1H), 3.85 (s, 3H), 3.09-3.02 (m, 2H), 2.98-2.87 (m, 2H), 2.12 (ddt, J=13.8, 11.4, 5.4 Hz, 1H), 2.08-2.03 (m, 2H), 1.84 (dddd, J=13.8, 11.4, 5.4, 3.0 Hz, 1H), 1.66 (p, J=7.8 Hz, 2H), 1.46-1.36 (m, 15H), 1.20-1.14 (m, 1H), 1.12-1.05 (m, 1H) ppm. ¹³C NMR (150 MHz, CDCl₃): δ 179.1, 173.2, 170.3, 156.1, 130.1, 114.5, 94.2, 79.3, 59.2, 58.8, 37.2, 33.8, 29.9, 28.9, 28.9, 28.8, 28.6, 24.5, 20.0 ppm HRMS (ESI) m/z calcd for C₂₂H₃₆N₂O₅ [M+H]⁺ 409.2697, found 409.2692.

Compound 3f (63%). [α]²⁰_D: −13.3 (c 0.06, MeOH). ¹H NMR (600 MHz, CDCl₃): δ 5.06 (s, 1H), 4.65 (dd, J=5.4, 3.0 Hz, 1H), 4.48 (br s, 1H), 3.85 (s, 3H), 3.77 (sextet, J=6.6 Hz, 1H), 3.07-3.04 (m, 2H), 2.17 (td, J=7.2, 2.4 Hz, 2H), 2.12 (ddt, J=13.8, 11.4, 5.4 Hz, 1H), 1.92 (t, J=3.0 Hz, 1H), 1.82 (dddd, J=13.8, 11.4, 5.4, 3.0 Hz, 1H), 1.78-1.73 (m, 1H), 1.56-1.49 (m, 2H), 1.48-1.36 (m, 14H), 1.19 (d, J=6.6 Hz, 3H), 1.17-1.14 (m, 1H), 1.12-1.07 (m, 1H) ppm. ¹³C NMR (150 MHz, CDCl₃): δ 179.1, 177.0, 170.0, 156.0, 94.3, 84.7, 79.3, 68.5, 68.3, 59.2, 58.8, 39.3, 32.4, 29.9, 28.7, 28.6, 26.6, 19.8, 18.5, 18.2 ppm. HRMS (ESI) m/z calcd for C₂₃H₃₆N₂O₅ [M+H]⁺ 421.2697, found 421.2693.

Compound 3g (27%). [α]²⁰_D: −43.5 (c 0.1, MeOH). ¹H NMR (600 MHz, CDCl₃): δ 4.90 (s, 1H), 4.52 (br s, 1H), 4.40 (dd, J=6.0, 3.0 Hz, 1H), 4.04 (s, 3H), 3.20 (h, J=6.6 Hz, 1H), 3.07 (br s, 2H), 2.21 (td, J=7.2, 2.4 Hz, 2H), 2.06-2.00 (m, 1H), 1.99-1.92 (m, 2H), 1.66-1.62 (m, 1H), 1.55-1.50 (m, 3H), 1.48-1.39 (m, 14H), 1.31-1.25 (m, 3H), 1.14 (d, J=7.2 Hz, 3H) ppm. $^{13}$C NMR (150 MHz, CDCl$_3$): δ 179.1, 177.0, 170.0, 156.1, 94.3, 84.6, 79.3, 68.5, 59.2, 58.8, 40.5, 39.1, 33.7, 30.0, 28.8, 28.6, 28.5, 26.4, 20.0, 18.5, 18.3 ppm. Doscadenamide F (1f) (80%). [α]$^{20}$$_D$: 23.0 (c 0.21, MeOH); $^1$H NMR (600 MHz, CDCl$_3$): δ 5.78 (m, 2H), 5.43 (br t, J=5.8 Hz, 1H), 5.04 (s, 1H), 5.00-4.91 (m, 4H), 4.64 (dd, J=5.8, 3.0 Hz, 1H), 3.84 (s, 3H), 3.76 (ddq, J=6.8, 6.8, 6.8, 1H), 3.26-3.20 (m, 1H), 3.17-3.11 (m, 1H), 2.1 (ddq, J=7.2 Hz, 1H), 2.08-2.00 (m, 5H), 1.84 (dddd, J=14.2, 11.2, 5.5, 3.1 Hz, 1H), 1.77-1.71 (m, 1H), 1.64-1.59 (m, 1H), 1.51-1.43 (m, 2H), 1.43-1.30 (m, 8H), 1.29-1.24 (m, 2H), 1.23-1.13 (m, 2H), 1.11 (d, J=6.6 Hz, 3H), 1.11 (d, J=7.2 Hz, 3H) ppm. $^{13}$C NMR (150 MHz, CDCl$_3$): δ 179.2, 177.2, 176.6, 170.0, 139.0, 139.0, 114.5, 114.5, 94.2, 59.2, 58.8, 41.8, 39.3, 39.2, 34.3, 34.1, 33.8, 33.7, 29.6, 29.0, 29.0, 27.1, 26.8, 20.4, 18.1, 16.3 ppm. HRMS (ESI) m/z calcd for C$_{26}$H$_{44}$N$_2$O$_4$ [M+H]$^+$ 461.33379, found 461.3369.

Doscadenamide H (1h) (69%). [α]$^{20}$$_D$: 54.3 (c 0.07, MeOH). $^1$H NMR (600 MHz, CDCl$_3$): δ 5.80 (ddt, J=16.8, 10.2, 6.6 Hz, 1H), 5.44 (br t, J=6.0 Hz, 1H), 5.05 (s, 1H), 5.01-4.91 (m, 2H), 4.63 (dd, J=5.4, 3.0 Hz, 1H), 3.85 (s, 3H), 3.26-3.20 (m, 1H), 3.19-3.13 (m, 1H), 2.96-2.87 (m, 2H), 2.19-2.16 (m, 2H), 2.15-2.08 (m, 2H), 2.07-2.03 (m, 2H), 1.93 (t, J=2.4 Hz, 1H), 1.85 (dddd, J=13.8, 11.4, 5.4, 3.0 Hz, 1H), 1.68-1.63 (m, 3H), 1.54-1.45 (m, 4H), 1.44-1.34 (m, 7H), 1.23-1.17 (m, 1H), 1.15-1.09 (m, 4H) ppm. $^{13}$C NMR (150 MHz, CDCl$_3$): δ 179.2, 176.4, 173.2, 170.3, 139.1, 114.5, 94.2, 84.6, 68.5, 59.1, 58.9, 41.8, 39.3, 37.2, 33.9, 33.8, 29.5, 28.9, 28.9, 28.8, 28.5, 26.7, 24.5, 20.3, 18.4, 18.1 ppm. HRMS (ESI) m/z calcd for C$_{26}$H$_{40}$N$_2$O$_4$ [M+H]$^+$ 445.3061, found 445.3059.

Doscadenamide I (1i) (79%). [α]$^{20}$$_D$: 59.3 (c 0.07, MeOH). $^1$H NMR (600 MHz, CDCl$_3$): δ 5.44 (br t, J=6.0 Hz, 1H), 5.05 (s, 1H), 4.63 (dd, J=6.0, 3.0 Hz, 1H), 3.85 (s, 3H), 3.26-3.20 (m, 1H), 3.19-3.13 (m, 1H), 2.99-2.89 (m, 2H), 2.20-2.16 (m, 4H), 2.15-2.08 (m, 2H), 1.93 (t, J=3.0 Hz, 2H), 1.85 (dddd, J=13.8, 11.4, 5.4, 3.0 Hz, 1H), 1.70-1.62 (m, 3H), 1.59-1.54 (m, 2H), 1.53-1.45 (m, δH), 1.41-1.34 (m, 3H), 1.23-1.17 (m, 1H), 1.15-1.08 (m, 4H) ppm. $^{13}$C NMR (150 MHz, CDCl$_3$): δ 179.2, 176.4, 173.1, 170.3, 94.2, 84.7, 84.6, 68.5, 68.4, 59.1, 58.9, 41.8, 39.3, 37.1, 33.9, 29.9, 29.6, 28.9, 28.5, 28.5, 28.4, 26.8, 26.7, 24.1, 20.3, 18.5, 18.4, 18.1 ppm. ppm. HRMS (ESI) m/z calcd for C$_{26}$H$_{38}$N$_2$O$_4$ [M+H]$^+$ 443.2904, found 443.2900.

Doscadenamide J (1j) (100%). [α]$^{20}$$_D$: 52.9 (c 0.07, MeOH). $^1$H NMR (600 MHz, CDCl$_3$): δ 5.48 (br t, J=6.0 Hz, 1H), 5.04 (s, 1H), 4.65 (dd, J=6.0, 3.0 Hz, 1H), 3.85 (s, 3H), 3.78 (h, J=6.6 Hz, 1H), 3.26-3.21 (m, 1H), 3.18-3.12 (m, 1H), 2.20-2.17 (m, 4H), 2.15 (t, J=7.2 Hz, 2H), 2.07 (ddt, J=13.8, 11.4, 5.4 Hz, 1H), 1.93 (t, J=3.0 Hz, 1H), 1.84 (dddd, J=13.8, 11.4, 5.4, 3.0 Hz, 1H), 1.78-1.73 (m, 1H), 1.65-1.62 (m, 1H), 1.56-1.51 (m, 4H), 1.50-1.47 (m, 2H), 1.46-1.40 (m, δH), 1.23-1.14 (m, 2H), 1.12 (d, J=6.6 Hz, 3H) ppm. $^{13}$C NMR (150 MHz, CDCl$_3$): δ 179.2, 177.0, 172.9, 170.0, 94.2, 84.7, 84.6, 68.5, 68.5, 59.2, 58.9, 39.5, 39.1, 36.8, 33.7, 29.5, 29.0, 28.5, 28.5, 28.3, 26.4, 25.4, 20.4, 18.5, 18.4, 16.3 ppm. HRMS (ESI) m/z calcd for C$_{26}$H$_{38}$N$_2$O$_4$ [M+H]$^+$ 443.2904, found 443.2903.

Doscadenamide S4 (1k) (83%). [α]$^{20}$$_D$: 44.0 (c 0.12, MeOH); $^1$H NMR (600 MHz, CDCl$_3$): δ 5.78 (m, 2H), 5.43 (br t, J=5.8 Hz, 1H), 5.04 (s, 1H), 5.00-4.91 (m, 4H), 4.64 (dd, J=5.8, 3.0 Hz, 1H), 3.84 (s, 3H), 3.76 (ddq, J=6.8, 6.8, 6.8, 1H), 3.26-3.20 (m, 1H), 3.17-3.11 (m, 1H), 2.1 (ddq, J=7.2 Hz, 1H), 2.08-2.00 (m, 5H), 1.84 (dddd, J=14.2, 11.2, 5.5, 3.1 Hz, 1H), 1.77-1.71 (m, 1H), 1.64-1.59 (m, 1H), 1.51-1.43 (m, 2H), 1.43-1.30 (m, 8H), 1.29-1.24 (m, 2H), 1.23-1.13 (m, 2H), 1.11 (d, J=6.6 Hz, 3H), 1.11 (d, J=7.2 Hz, 3H) ppm. $^{13}$C NMR (150 MHz, CDCl$_3$): δ 179.2, 177.2, 176.6, 170.0, 139.0, 139.0, 114.5, 114.5, 94.2, 59.2, 58.8, 41.8, 39.3, 39.2, 34.3, 34.1, 33.8, 33.7, 29.6, 29.0, 29.0, 27.1, 26.8, 20.4, 18.1, 16.3 ppm. HRMS (ESI) m/z calcd for C$_{27}$H$_{48}$N$_2$O$_4$ (M+H)+465.3692, found 465.3685.

Doscadenamide S5 (1l) (77.5%). [α]$^{20}$$_D$: 102.1 (c 0.07, MeOH). $^1$H NMR (600 MHz, CDCl$_3$): δ 5.80 (ddt, J=16.8, 10.2, 6.6 Hz, 1H), 5.45 (br t, J=5.4 Hz, 1H), 5.05 (s, 1H), 5.01-4.91 (m, 2H), 4.63 (dd, J=5.4, 3.0 Hz, 1H), 3.85 (s, 3H), 3.25-3.15 (m, 2H), 2.96-2.87 (m, 2H), 2.19-2.16 (m, 2H), 2.14-2.08 (m, 2H), 2.07-2.03 (m, 2H), 1.93 (t, J=2.4 Hz, 1H), 1.85 (dddd, J=13.8, 11.4, 5.4, 3.0 Hz, 1H), 1.68-1.63 (m, 3H), 1.54-1.45 (m, 4H), 1.44-1.34 (m, 7H), 1.23-1.16 (m, 1H), 1.16-1.08 (m, 4H) ppm. $^{13}$C NMR (150 MHz, CDCl$_3$): δ 179.1, 176.4, 173.2, 170.2, 139.1, 114.5, 94.2, 84.6, 68.5, 59.1, 58.9, 41.7, 39.2, 37.2, 33.9, 33.8, 29.5, 28.9, 28.9, 28.8, 28.5, 26.7, 24.5, 20.3, 18.4, 18.1 ppm. HRMS (ESI) m/z calcd for C$_{26}$H$_{40}$N$_2$O$_4$ [M+H]$^+$ 445.3061, found 445.3058.

Doscadenamide S6 (1m) (60%). [α]$^{20}$$_D$: 82.9 (c 0.07, MeOH). $^1$H NMR (600 MHz, CDCl$_3$): δ 5.47 (br t, J=7.2 Hz, 1H), 5.05 (s, 1H), 4.63 (dd, J=5.4, 3.0 Hz, 1H), 3.85 (s, 3H), 3.25-3.15 (m, 2H), 2.99-2.89 (m, 2H), 2.21-2.16 (m, 4H), 2.14-2.08 (m, 2H), 1.94-1.93 (m, 2H), 1.85 (dddd, J=13.8, 11.4, 5.4, 3.0 Hz, 1H), 1.69-1.63 (m, 3H), 1.59-1.56 (m, 2H), 1.56-1.42 (m, δH), 1.41-1.35 (m, 3H), 1.22-1.14 (m, 1H), 1.13-1.09 (m, 4H) ppm. $^{13}$C NMR (150 MHz, CDCl$_3$): δ 179.2, 176.4, 173.1, 170.3, 94.1, 84.7, 84.6, 68.5, 68.4, 59.2, 58.9, 41.8, 39.3, 37.1, 33.9, 29.5, 28.9, 28.5, 28.5, 28.5, 28.4, 26.7, 24.1, 20.2, 18.4, 18.1 ppm. HRMS (ESI) m/z calcd for C$_{26}$H$_{38}$N$_2$O$_4$ [M+H]$^+$ 443.2904, found 443.2903.

Doscadenamide S7 (1n) (58.1%). [α]$^{20}$$_D$: 42.9 (c 0.07, MeOH). $^1$H NMR (600 MHz, CDCl$_3$): δ 5.79 (ddt, J=16.8, 10.2, 6.6 Hz, 1H), 5.46 (br t, J=5.4 Hz, 1H), 5.05 (s, 1H), 5.01-4.92 (m, 2H), 4.65 (dd, J=6.6, 3.0 Hz, 1H), 3.85 (s, 3H), 3.80-3.75 (m, 1H), 3.26-3.20 (m, 1H), 3.18-3.12 (m, 1H), 2.18 (td, J=7.2, 2.4 Hz, 2H), 2.14 (t, J=7.2 Hz, 2H), 2.10-2.02 (m, 3H), 1.93 (t, J=2.4 Hz, 1H), 1.85 (dddd, J=13.8, 11.4, 5.4, 3.0 Hz, 1H), 1.78-1.73 (m, 1H), 1.65-1.60 (m, 5H), 1.57-1.49 (m, 3H), 1.49-1.37 (m, 7H), 1.35-1.29 (m, 2H), 1.23-1.14 (m, 2H), 1.12 (d, J=6.6 Hz, 3H) ppm. $^{13}$C NMR (150 MHz, CDCl$_3$): δ 179.2, 177.0, 173.1, 170.0, 138.9, 114.6, 94.2, 84.7, 68.5, 59.2, 58.9, 39.5, 39.1, 36.9, 33.7, 29.5, 29.0, 28.9, 28.7, 28.5, 26.4, 25.8, 20.4, 18.5, 16.3 ppm. HRMS (ESI) m/z calcd for C$_{26}$H$_{40}$N$_2$O$_4$ [M+H]$^+$ 445.3061, found 445.3059.

Doscadenamide S13 (1o) (66%). [α]$^{20}$$_D$: −40.0 (c 0.09, MeOH). $^1$H NMR (600 MHz, CDCl$_3$): δ 5.42 (br t, J=6.0 Hz, 1H), 5.06 (s, 1H), 4.64 (dd, J=5.4, 3.0 Hz, 1H), 3.85 (s, 3H), 3.77 (sextet, J=6.6 Hz, 1H), 3.25-3.20 (m, 1H), 3.19-3.14 (m, 1H), 2.20-2.16 (m, 4H), 2.14-2.08 (m, 2H), 1.93 (t, J=2.4 Hz, 1H), 1.92 (t, J=2.4 Hz, 1H), 1.83 (dddd, J=13.8, 11.4, 5.4, 3.0 Hz, 1H), 1.77-1.72 (m, 1H), 1.65-1.61 (m, 1H), 1.53-1.46 (m, δH), 1.45-1.34 (m, 3H), 1.32-1.28 (m, 3H), 1.18 (d, J=7.2 Hz, 3H), 1.16-1.13 (m, 2H), 1.12 (d, J=6.6 Hz, 3H) ppm. $^{13}$C NMR (150 MHz, CDCl$_3$): δ 179.2, 177.0, 176.4, 170.0, 94.2, 84.7, 84.6, 68.5, 68.3, 59.2, 58.9, 41.7, 39.3, 39.3, 33.9, 32.5, 32.1, 29.5, 29.2, 29.0, 28.7, 28.5, 26.8, 26.6, 20.2, 18.5, 18.4, 18.1, 18.1 ppm. HRMS (ESI) m/z calcd for C$_{27}$H$_{40}$N$_2$O$_4$ [M+H]$^+$ 457.3061, found 457.3056.

Doscadenamide S14 (1p) (38%). [α]$^{20}$$_D$: −41.4 (c 0.07, MeOH). $^1$H NMR (600 MHz, CDCl$_3$): δ 5.59 (br t, 1H), 4.90 (s, 1H), 4.40 (dd, J=6.0, 3.6 Hz, 1H), 4.04 (s, 3H), 3.27-3.15 (m, 3H), 2.22-2.13 (m, 5H), 2.04-1.93 (m, 4H), 1.79-1.72 (m, 1H), 1.67-1.60 (m, 1H), 1.56-1.47 (m, δH), 1.46-1.40 (m, 3H), 1.39-1.35 (m, 3H), 1.33-1.28 (m, 2H), 1.14 (d, J=6.6 Hz, 3H), 1.11 (d, J=6.6 Hz, 3H) ppm. $^{13}$C NMR (150 MHz, CDCl$_3$): δ 196.9, 176.5, 175.2, 174.0, 86.6, 84.7, 84.4, 68.7, 68.5, 65.7, 59.9, 41.7, 40.3, 39.1, 33.9, 29.4, 29.2, 28.6, 28.4, 26.8, 26.5, 20.5, 19.3, 18.5, 18.4, 18.1, 16.9 ppm. HRMS (ESI) m/z calcd for C$_{27}$H$_{40}$N$_2$O$_4$ [M+H]$^+$ 457.3061, found 457.3055.

Scheme 6. Synthesis of 2a and 2b.

Doscadenamide S8 (2a)

Doscadenamide S9 (2b)

Synthesis 2a or 2b (Scheme 6). To the solution of compound 5a (4.5 mg, 0.016 mmol) in $CH_2Cl_2$ (0.8 mL) was added TFA (0.4 mL) at 0° C. and the mixture was stirred the same temperature for 30 min. The reaction residue was diluted with toluene (1 mL) and evaporated in vacuo (3 times) to produce an intermediate crude that was used in next step without purification. To the solution of this intermediate crude in anhydrous DMF (1.0 mL) was added corresponding acid 6 (2.5 mg, 0.016 mmol), EDCI·HCl (4.6 mg, 0.024 mmol), HOBt·$H_2O$ (3.9 mg, 0.025 mmol) and DIEA (8.4 μL). The reaction mixture was stirred at room temperature for 20 h and then was evaporated in vacuo and purified by preparative TLC plate to yield corresponding product 2 as white solid.

Doscadenamide S8 (2a) (33% 2 steps). $[\alpha]^{20}_D$: −5.0 (c 0.1, MeOH). $^1H$ NMR (600 MHz, $CDCl_3$): δ 5.93 (br s, 1H), 5.47 (br t, J=5.4 Hz, 1H), 5.00 (s, 1H), 4.05 (dd, J=7.2, 3.6 Hz, 1H), 3.79 (s, 3H), 3.32-3.27 (m, 1H), 3.24-3.18 (m, 1H), 2.20-2.13 (m, 3H), 1.93 (t, J=2.4 Hz, 1H), 1.86-1.80 (m, 1H), 1.67-1.64 (m, 1H), 1.58-1.49 (m, 5H), 1.44-1.36 (m, 4H), 1.36-1.28 (m, 1H), 1.14 (d, J=7.2 Hz, 3H) ppm. $^{13}C$ NMR (150 MHz, $CDCl_3$): δ 178.3, 176.7, 174.5, 93.7, 84.6, 68.5, 58.5, 57.4, 41.7, 39.0, 31.3, 29.6, 28.5, 26.8, 22.0, 18.5, 18.2 ppm. HRMS (ESI) m/z calcd for $C_{18}H_{28}N_2O_3$ [M+H]$^+$ 321.2173, found 321.2169.

Doscadenamide S9 (2b) (43% 2 steps). $[\alpha]^{20}_D$: 17.0 (c 0.1, MeOH). $^1H$ NMR (600 MHz, $CDCl_3$): δ 6.19 (br s, 1H), 5.68 (br t, J=5.4 Hz, 1H), 4.99 (s, 1H), 4.05 (dd, J=7.8, 4.2 Hz, 1H), 3.79 (s, 3H), 3.32-3.27 (m, 1H), 3.23-3.18 (m, 1H), 2.20-2.13 (m, 3H), 1.93 (t, J=3.0 Hz, 1H), 1.85-1.80 (m, 1H), 1.67-1.64 (m, 1H), 1.57-1.48 (m, 5H), 1.44-1.36 (m, 4H), 1.36-1.29 (m, 1H), 1.13 (d, J=7.2 Hz, 3H) ppm. $^{13}C$ NMR (150 MHz, $CDCl_3$): δ 178.4, 176.7, 174.6, 93.7, 84.6, 68.5, 58.5, 57.4, 41.7, 39.0, 33.9, 31.3, 29.5, 28.5, 26.8, 22.1, 18.5, 18.1 ppm. HRMS (ESI) m/z calcd for $C_{18}H_{28}N_2O_3$ [M+H]$^+$ 321.2173, found 321.2169.

Scheme 7. Synthesis of 4a.

1a

-continued

Doscadenamide S15 (4a)

To a solution of 1a (1.0 mg, 0.0022 mmol) in anhydrous THF (0.5 mL) was added pyridine (0.25 mL), Cu(OAc)2 (23.8 mg, 0.131 mmol) and CuI (6.3 mg, 0.033 mmol) sequentially. The reaction was stirred at room temperature overnight and the purification with preparative TLC to provide product 4a (0.8 mg, 80%).

Doscadenamide S15 (4a): $[\alpha]^{20}_D$ 14.0 (c 0.07, MeOH); $^1$H NMR (600 MHz, CDCl$_3$) δ ppm: 5.61 (br t, J=5.90 Hz, 1H), 5.06 (s, 1H), 4.69 (dd, J=5.8, 3.0 Hz, 1H), 3.90 (ddt, J=6.8, 5.0, 3.3 Hz, 1H), 3.86 (s, 3H), 3.28-3.19 (m, 2H), 2.31-2.24 (m, 4H), 2.19 (dqd, J=10.3, 6.7, 3.9, 1H), 2.10 (ddt, J=14.1, 10.9, 5.2, 1H), 1.90 (dddd, J=14.3, 11.5, 5.6, 3.2 Hz, 1H), 1.80 (dtd, J=13.5, 9.3, 5.2 Hz, 1H), 1.67-1.65 (m, 1H), 1.52-1.42 (m, 9H), 1.32-1.28 (m, 3H), 1.19-1.15 (m, 2H), 1.12 (d, J=6.8, 6H); $^{13}$C NMR (150 MHz, CDCl$_3$) δ ppm: 179.2, 176.9, 176.2, 170.1, 94.2, 77.7, 77.7, 66.1, 65.4, 59.1, 58.9, 41.7, 41.2, 39.6, 38.8, 34.0, 29.7, 29.5, 28.2, 27.1, 26.3, 26.1, 20.6, 19.4, 19.2, 18.6, 17.2; HRMS (ESI) m/z calcd for $C_{27}H_{38}N_2O_4(M+H)^+$ 455.2910, found 455.2899.

Quorum Sensing Signaling

Figure 15:
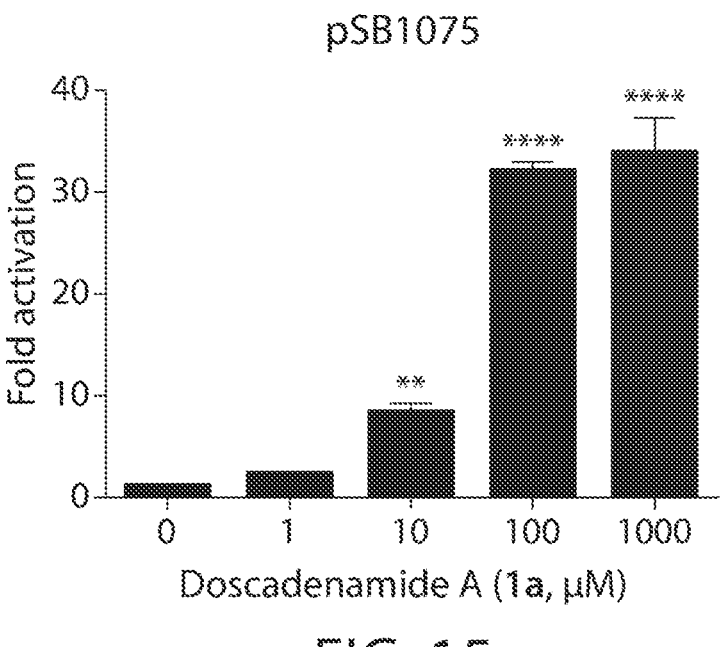
FIG. 15. depicts activating activity of doscadenamide A (1a) in pSB1075, the lasR-luxCDABE reporter constructs expressed in E. coli. The bacterial cultures were treated with 1a in a dose-response manner and solvent control at 37° C. for 6 h before fluorescence was measured. Results are expressed as fold activation compared to solvent control. Data are presented as mean±SD, P<0.01, **P<0.0001, compared to solvent control using one-way ANOVA (n=3).
Figure 16:
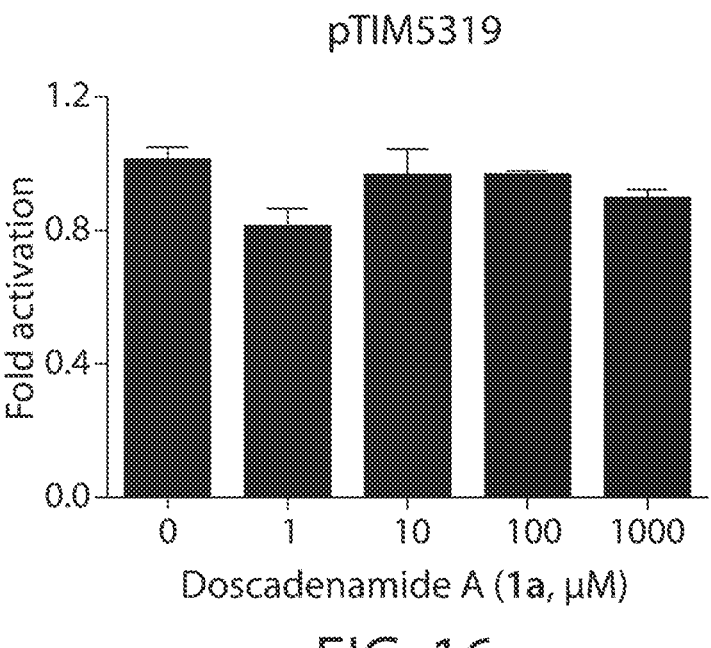
FIG. 16. depicts activating activity of doscadenamide A (1a) in related reporter pTIM5319, which lacks a functional AHL-binding domain. The bacterial cultures were treated with 1a in a dose-response manner and solvent control at 37° C. for 6 h before fluorescence was measured. Results are expressed as fold activation compared to solvent control.

Preliminary screening results indicated that 1a can activate the 3-oxo-C12-HSL-responsive reporter plasmid pSB1075, a plasmid encoding LasR and containing a light-producing luxCDABE cassette expressed in *E. coli* (FIG. 15) [Winson, M. K.; Swift, S.; Fish, L.; Throup, J. P.; Jørgensen, F.; Chhabra, S. R.; Bycroft, B. W.; Williams, P.; Stewart, G. S., *FEMS Microbiol. Lett.* 1998, 163 (2), 185-192]. However, 1a was not able to activate the related reporter pTIM5319, which is identical to pSB1075 but lacks the AHL-binding site LasR (FIG. 16), which suggests that 1a exerts the QS activating activity via the AHL-binding site [Kwan, J. C.; Meickle, T.; Ladwa, D.; Teplitski, M.; Paul, V.; Luesch, H., *Mol. Biosyst.* 2011, 7 (4), 1205-1216]. To validate the activating activity of 1a, its effect on wild-type *P. aeruginosa* was tested. As shown in FIG. 17, after treatment with 1a, the production and expression of the secreted QS pigment pyocyanin was elevated. For comparison, the other three diastereomers 1b, 1c and 1d were also included in the test. Such superagonists are expected to artificially regulate virulence factor production such as pyocyanin and activate QS at lower bacterial cell populations, thus to stimulate the host immune system to clear the infection when fewer bacterial cells are present [Galloway, W.; Hodgkinson, J.; Bovvden, S.; Welch, M.; Spring, D., *Trends Microbiol.* 2012, 20 (9), 449-458].

QS Modulation by Doscadenamides in *Pseudomonas aeruginosa* and LasR Molecular Interaction Studies Doscadenamide A (1a) activates QS, which was established using the 3-oxo-C12-HSL-responsive reporter plasmid pSB1075, a plasmid encoding LasR (the C12 HSL receptor in *Pseudomonas aeruginosa*) and containing a light-producing luxCDABE cassette expressed in *Escherichia coli*. The activity was abolished in a strain (pTIM5319) that lacked the AHL domain but was otherwise identical.

To follow up our previous study regarding the QS modulatory activity of doscadenamide A (1a) on wild-type *P. aeruginosa* and extend reporter gene assay studies, we examined the QS activation of different doscadenamides using a QS system deficient strain, PAO-JP1. PAO-JP1 is a *P. aeruginosa* mutant with a lasI deletion that cannot produce C12. To investigate the activating effect of doscadenamide A (1a) on *P. aeruginosa* without interference from the C12 produced by *P. aeruginosa* itself, we examined the pyocyanin production of *P. aeruginosa* mutant PAO-JP1 after treatment with doscadenamide A (1a) and selected structural analogues for 6 h at 10 μM.

Compounds selected for this bioassay possessed a different number of carboxylic acid chains (1a vs 2a vs 3a), different degrees of unsaturation (1a/f/k vs 3a-c). As shown in FIG. 3B, when normalized for cell number, these doscadenamides (FIG. 1) can all activate the pyocyanin production of PAO-JP1 but to a different extent at the concentration of 100 μM. Doscadenamide A (1a) induced 3-fold QS activation, similarly to the positive control C12. Compound 2a, which possesses only one chain (Moya1), exhibits minimal QS-activating effect, while 3a-c with acylation of the amide core showed the most potent activation, 3-fold, 4-fold and 5-fold, indicating that this chain is predominantly responsible for the QS agonist activity in *P. aeruginosa*. The degree of unsaturation appears to play a minor role in chain-dependent fashion as the trends for 1a/f/k vs 3a-c were opposite, possibly indicating the dependence of both chains to the overall net effect. The overall trend was the same even without normalization for bacterial cell count, except that 2a did not show any level of activation, further underscoring the usefulness of Moya2 (regardless of degree of saturation) for QS activation.

QS Modulation by Doscadenamides in Other Gram-Negative Bacteria: *Vibrio harveyi*

We then aimed to determine if doscadenamides modulate QS in other Gram-negative bacteria as well. To extend our investigation of doscadenamides on QS modulation, we adopted a bioluminescent marine bacterium, *Vibrio harveyi*, as our model system to examine the effect of doscadenamides on modulating the bioluminescence production by *V. harveyi*. *V. harveyi* has been reported to be responsive to bacterial QS activator N-(3-oxododecanoyl-L-homoserine lactone (C12) and thus a robust model for quorum sensing related research.

Most Gram-negative bacteria possess QS circuits similar to the marine symbiotic bioluminescent bacterium *Vibrio fischeri*, the QS system of which has been studied the most. As the *V. fischeri* population grows, it produces and releases autoinducer molecules to accumulate and thus eliciting bioluminescence. There are two proteins, LuxI and LuxR, in *V. fischeri* to regulate QS signaling pathway. LuxI regulates the production of the autoinducer, N-(3-oxohexanoyl)-homoserine lactone ($C_6$). LuxR binds to the autoinducer and activates the transcription of luciferase enzymes for bioluminescence production. In *P. aeruginosa*, two pairs of LuxI/LuxR homologues, namely LasI/LasR and RhlI/RhlR, exist to regulate the QS signaling pathway. For these two signaling systems, the RhlI/RhlR system is subordinate to the LasI/LasR system. Two acylhomoserine lactones (AHLs), C12 and N-butyryl-homoserine lactone (C4), are required to trigger the expression of RhlR and its downstream target genes including virulence factor production; while the expression of LasR is independent of the AHL-mediated QS signaling pathway, thus making LasR a representive target for QS inhibition. Compared to *V. fischeri* and *P. aeruginosa*, *V. harveyi* contains a more complex QS cascade involving three parallel regulating QS-signaling pathways and responds to three different autoinducers. Even though the homologous LuxI/LuxR system of *V. fischeri* has never been identified in *V. harveyi*, *V. harveyi* can produce and detect autoinducer 1 (AI-1), N-(3-hydroxybutanoyl) homoserine lactone, which shares significant similarity to C12 and C4. Tyr 56 and Asp73 are conserved in both LasR and LuxR systems. Therefore, we adopted *V. harveyi* as a practical model to understand and validate the QS modulating activity of doscadenamide A (1a) and its analogs (FIG. 1).

Almost all compounds activated QS in this biological context to a certain extent (FIG. 19C), with 1a and 3a activating across the concentration range tested (10-200 PM). However, 3c only had a minor activating trend and for 1f and 1j the activities at <100 μM were also reduced, suggesting that increased saturation of the terminal units decreases activity for both chains. Notably, 2a was not able to activate the bioluminescent response in *V. harveyi* but, instead, consistently inhibited QS signaling in *V. harveyi*, whereas the same compound was essentially inactive in *P. aeruginosa*. In both cases, 2a was not able to activate QS, providing common ground in the two Gram-negative bacteria. The same trend in *V. harveyi* was observed without normalization for cell number, indicating that the differential effect is not an artifact of normalization.

These results indicate that both acylations in doscadenamide A (1a) are involved in the QS modulating activity, with partially overlapping but also bacteria context-specific trends. Both chains contribute differently to the final biological activity output, even in opposing or interacting fashion, suggesting a more complex interaction between doscadenamide A (1a) and its molecular targets in various bacterial systems, potentially regulating their respective activity.

Synergy with TRAIL in MDA-MB-231 Breast Cancer Cells

TRAIL has been regarded as an attractive therapeutic anticancer agent; however, many cancer cells have developed resistance to TRAIL and impacted the treatment efficacy. Given that C12 was reported to exhibit synergistic effect on TRAIL-induced apoptosis in cancer cells, we examined the potential synergistic effect of doscadenamide A (1a) and its analogs on sensitizing cancer cells. First, we generated the dose response of TRAIL on MDA-MB-231 breast cancer cells, which were partially responsive to TRAIL, 50% cell viability remaining at 500 ng/mL (FIG. 20A), and selected 20 ng/mL as our test concentration, under which TRAIL would only induce a small fraction (approximately 20%) of cells to undergo apoptotic death. MDA-MB-231 cells were pretreated with C12, doscadenamides or solvent control for 3 h and then stimulated with TRAIL for 24 h (FIGS. 20B and 20C). We measured cell viability and calculated the A Bliss independence of each compound with TRAIL. Most analogs exhibited synergistic effect with TRAIL, except 2a (FIG. 1), and among all the analogs, the "saturated" analogs 1k and 3c (FIG. 1) behaved as the best agents to sensitize MDA-MB-231 cells (FIG. 20D). To further investigate the pro-apoptotic effect of doscadenamide A (1a), the PARP cleavage was also analyzed using Western blot (FIG. 20E) to indicate programmed cell death. There was a clear decrease in cell viability and an evident presence of cleaved PARP in cell extracts after co-treatment; therefore, the doscadenamide A (1a) and compounds of the disclosure can effectively improve TRAIL-induced apoptosis in MDA-MB-231 cells. Furthermore, our SAR study reveals that the less the unsaturation degree the compound possesses, the more effectively it acts on ameliorating TRAIL resistance and the one side chain Moya2 plays a useful role in exhibiting bioactivities, which generally correlated with our QS results, in that the side chain Moya2 was useful for activity since 2a showed no effect on cell viability (FIGS. 20B and 20C) or effect on PARP cleavage. Compound 3c showed even enhanced activity compared with the doubly acylated versions, including parent compound, doscadenamide A (1a). As expected, the cyclized version 4a was completely inactive in these assays. Interestingly, compared to doscadenamide A (1a), the analogs with less unsaturation (1f, 1k, 3b and 3c) exhibit improved cytoxicity.

Biological Experimental Procedures

Quorum Sensing Reporter Assays with Doscadenamide A (1a)

Doscadenamide A (1a) in a dose-response manner and EtOH control were added to the corresponding wells in a 96-well plate and the solvent was allowed to evaporate. Then 100 μL of an overnight culture of *E. coli* expressing plasmid wild-type pSB1075 (a luxCDABE reporter construct encoding LasR) or an overnight *E. coli* culture expressing reporter pSB1075 mutant (Y56F, W60F or D73N), was added to each well. The plate was incubated at 37° C. for 6 h before the measurement of luminescence.

Pyocyanin Quantification in *P. aeruginosa* Strain PAO-JP1

An overnight culture of *P. aeruginosa* strain PAO-JP1 was diluted 10-fold before transferred to another culture tube containing 890 μL LB broth and 10 μL testing compound (10 μM final concentration) or EtOH control and incubated at 37° C. with shaking for 6 h. The culture was then spun down for 10 min at the maximum speed, and the supernatant was collected and filtered using 0. μM Eppendorf filters. 500 μL of the sterile supernatant were added to 500 μL CHCl₃ in an Eppendorf tube. Tube shaking allowed for the extraction of pyocyanin in the CHCl₃ layer. This layer was then added to 150 μL of 0.2 N HCl in another Eppendorf tube. After shaking, the aqueous layer and the organic layer were separated. 100 μL of the aqueous layer were transferred to a clear bottomed 384-well plate and the absorbance was measured at 385 nm to quantify the pyocyanin production. Data was analyzed using GraphPad Prism 5 software.

Bioluminescence Modulation in *V. harveyi*

Bioluminescent *V. harveyi* BB120 strain (wild-ype) was cultivated in AB media overnight (15-16 h) at 30° C. (OD600 is about 2.0-2.5). The overnight cultivated strain 2 L was diluted to 10 mL by AB media (OD600<0.1). 100 μL the diluted BB120 strain was distributed to each well of 96-well white plate. The solution of each tested compound in DMSO (0.5 μL) at different concentration was added to BB120 cultures on plate. Triplicate was conducted for each compound and each concentration. After addition, bacterial cultures were incubated at 30° C. for 7 hours. Then the emitted luminescence and OD600 was measured by BioTek Synergy H1 plate reader. AI-1 and DMSO were used as positive control and negative control, respectively.

Synergistic Effect Evaluation of Doscadenamide Analogs with TRAIL

MDA-MB-231 cells were seeded in 12-well plates at a density of 100,000 cells per well. The next day, cells were pretreated with doscadenamide analogs (5 μM and 2 μM), positive controls (C12) or solvent control (DMSO) for 3 h. Then the cells were treated with TRAIL (20 ng/mL) for 24 h. The whole cell lysates were collected using PhosphoSafe Buffer (EMD Chemicals). Protein concentrations were measured with the BCA Protein Assay kit (Thermo Fisher Scientific). Lysates containing equal amounts of protein were separated by NuPAGE 4-12% Bis-Tris protein gels (Thermo Fisher Scientific), trans-ferred to polyvinylidene difluoride membranes, probed with primary and secondary antibodies. The membranes were visualized using Li-Cor imaging system. Anti-PARP and anti-actin antibodies were from Cell Signaling. Secondary anti-mouse and anti-rabbit antibodies were from Invitrogen.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A compound of Formula (IX):

(IX)

or a pharmaceutically acceptable salt, solvate, or hydrate thereof;

wherein $R_{13}$ is H, Boc, acetyl, Fmoc, each $R_{14}$ is independently H or $C_1$-$C_6$ alkyl;

$R_{15}$ is H or $C_1$-$C_6$ alkyl;

each $R_6$ is independently H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl, wherein the compound is not:

(doscadenamide A)

127
-continued

128
-continued (doscadenamide B)

(doscadenamide G)

(doscadenamide C)

(doscadenamide H)

(doscadenamide D)

(doscadenamide I)

(doscadenamide E)

(doscadenamide J)

2. The compound of claim 1, or pharmaceutically acceptable salt thereof, wherein the compound is a compound according to Formula (I):

(doscadenamide F)

(I)

or a pharmaceutically acceptable salt thereof;

wherein R₁ is H, Boc, acetyl, Fmoc, or

R₂ is H or C₁-C₆ alkyl;
R₃ is H;
R₄ is H or C₁-C₆ alkyl;
R₅ is H or C₁-C₆ alkyl;
R₆ is H, C₁-C₆ alkyl, C₂-C₆ alkenyl, or C₂-C₆ alkynyl; and
R₇ is H, C₁-C₆ alkyl, C₂-C₆ alkenyl, or C₂-C₆ alkynyl.

3. The compound of claim 2, or a pharmaceutically acceptable salt thereof, wherein the compound is a compound according to Formula (II):

(II)

or a pharmaceutically acceptable salt thereof.

4. The compound of claim 2, or a pharmaceutically acceptable salt thereof, according to Formula (III):

(III)

or a pharmaceutically acceptable salt thereof.

5. The compound of claim 2, or a pharmaceutically acceptable salt thereof, according to Formula (IV):

(IV)

or a pharmaceutically acceptable salt thereof.

6. The compound of claim 2, or a pharmaceutically acceptable salt thereof, wherein the compound is:

(doscadenamide S1)

(doscadenamide S2)

(doscadenamide S6)

(doscadenamide S5)

-continued (doscadenamide 11)

(doscadenamide 12)

or a pharmaceutically acceptable salt thereof.

7. The compound of claim 2, or a pharmaceutically acceptable salt thereof, wherein the compound is:

(doscadenamide S12)

or a pharmaceutically acceptable salt thereof.

8. The compound of claim 1, or pharmaceutically acceptable salt thereof, wherein the compound is a compound according to Formula (VIII):

(VIII)

or a pharmaceutically acceptable salt thereof;

wherein:

$R_{16}$ is H, $C_1$-$C_6$ alkyl, $C_2$-$C_6$ alkenyl, or $C_2$-$C_6$ alkynyl; and $R_{17}$ is H or $C_1$-$C_6$ alkyl; or $R_{16}$ is H or $C_1$-$C_6$ alkyl; and $R_{17}$ is H, $C_1$-$C_6$ alkyl, $C_2$-$C_6$ alkenyl, or $C_2$-$C_6$ alkynyl.

9. The compound of claim 8, or a pharmaceutically acceptable salt thereof, wherein the compound is:

(doscadenamide S4), or a pharmaceutically acceptable salt thereof.

10. The compound of claim 1, or pharmaceutically acceptable salt thereof, wherein the compound is a compound according to Formula (V):

(V)

or a pharmaceutically acceptable salt thereof;

wherein $R_4$ is H or $C_1$-$C_6$ alkyl;

$R_5$ is H or $C_1$-$C_6$ alkyl;

$R_6$ is H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl.

11. The compound of claim 10, or a pharmaceutically acceptable salt thereof, wherein the compound is:

(doscadenamide S13)

or a pharmaceutically acceptable salt thereof.

12. The compound of claim 11, or pharmaceutically acceptable salt thereof, wherein the compound is a compound according to Formula (VI):

(VI)

or a pharmaceutically acceptable salt thereof;

wherein $R_{12}$ is H, Boc, acetyl, Fmoc, or

134

$R_{11}$ is $C_1$-$C_6$ alkyl;

$R_6$ is H, $C_1$-$C_6$ alkyl, $C_2$-$C_6$ alkenyl, or $C_2$-$C_6$ alkynyl;

$R_8$ is H, Boc, acetyl, Fmoc, or $R_7$ is H, $C_1$-$C_6$ alkyl, $C_2$-$C_6$ alkenyl, or $C_2$-$C_6$ alkynyl;

$R_9$ is H or $C_1$-$C_6$ alkyl; and $R_{10}$ is H or $C_1$-$C_6$ alkyl.

13. The compound of claim 12, or a pharmaceutically acceptable salt thereof, wherein the compound is:

(doscadenamide S2)

(doscadenamide S3)

(doscadenamide S8)

or (doscadenamide S9)

or a pharmaceutically acceptable salt thereof.

14. A pharmaceutical composition comprising a compound of claim 1, or a pharmaceutically acceptable salt thereof, and a pharmaceutically acceptable carrier.

15. A method of activating quorum sensing signaling, the method comprising administering an effective amount of a compound of claim 1, or a pharmaceutically acceptable salt thereof.

16. A method of inhibiting bacterial growth, the method comprising administering an effective amount of a compound of claim 1, or a pharmaceutically acceptable salt thereof.

17. A method of treating a bacterial infection in a subject, the method comprising administering an effective amount of a compound of claim 1, or a pharmaceutically acceptable salt thereof.

18. A method of treating cancer in a subject, the method comprising administering an effective amount of a compound of claim 1, or a pharmaceutically acceptable salt thereof.

19. A method of increasing the effectiveness of anti-cancer therapy in a subject currently being administered one or more anti-cancer therapies, the method comprising administering an effective amount of a compound of claim 1, or a pharmaceutically acceptable salt thereof.

20. A method of increasing the effectiveness of anti-bacterial therapy in a subject currently being administered one or more anti-bacterial therapies, the method comprising administering an effective amount of a compound of claim 1, or a pharmaceutically acceptable salt thereof.

21. The method of claim 18, wherein the cancer is breast cancer.

22. The method of claim 21, wherein the cancer is triple negative breast cancer.

23. The method of claim 19, wherein the anti-cancer therapy is tumor necrosis factor-related apoptosis-inducing ligand (TRAIL) or a TRAIL receptor agonist.

\* \* \* \* \*